US012774456B2

(12) United States Patent
Chen et al.

(10) Patent No.: US 12,774,456 B2
(45) Date of Patent: *Oct. 27, 2026

(54) COMPOSITIONS AND METHODS FOR GENE EDITING

(71) Applicant: The Regents of the University of California, Oakland, CA (US)

(72) Inventors: Jin Chen, San Francisco, CA (US); Luke Gilbert, San Francisco, CA (US); James Nunez, San Francisco, CA (US); Jonathan Weissman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 598 days.

This patent is subject to a terminal disclaimer.

(21) Appl. No.: 17/816,369

(22) Filed: Jul. 29, 2022

(65) Prior Publication Data

US 2023/0124253 A1 Apr. 20, 2023

Related U.S. Application Data

(63) Continuation of application No. 17/726,290, filed on Apr. 21, 2022, which is a continuation of application (Continued)

(51) Int. Cl.

*C12N 15/62* (2006.01)
*C07K 14/47* (2006.01)

(Continued)

(52) U.S. Cl.

CPC .......... *C12N 15/62* (2013.01); *C07K 14/4702* (2013.01); *C12N 9/1007* (2013.01);

(Continued)

(58) Field of Classification Search

CPC ........ C12N 15/62; C12N 9/1007; C12N 9/22; C07K 2319/00; C07K 2319/09; C12Y 201/01072

See application file for complete search history.

(56) References Cited

U.S. PATENT DOCUMENTS 6,919,204 B2 7/2005 Wolffe et al.
8,658,393 B2 2/2014 Reik et al.

(Continued)

FOREIGN PATENT DOCUMENTS

WO WO-03/072788 A1 9/2003
WO WO-2013/141680 A1 9/2013

(Continued)

OTHER PUBLICATIONS

DeWitt, Mark A., et al. "Genome Editing via Delivery of Cas9 Ribonucleoprotein." Methods, vol. 121-122, May 2017, pp. 9-15, https://doi.org/10.1016/j.ymeth.2017.04.003. Accessed May 6, 2020. (Year: 2017).*

(Continued)

*Primary Examiner* — Kimberly Chong
*Assistant Examiner* — Africa M Mcleod
(74) *Attorney, Agent, or Firm* — Mintz Levin Cohn Ferris Glovsky and Popeo, P.C.

(57) ABSTRACT

Provided herein are, inter alia, compositions and methods for manipulation of genomes of living organisms. Provided herein also are fusion protein compositions that can turn off genes permanently and reversibly in mammalian cells using CRISPR-based epigenome editing. In addition, the methods provided herein include complexes including: (i) a fusion protein including, from N-terminus to C-terminus, a DNA methyltransferase domain, a nuclease deficient RNA-guided (Continued)

endonuclease enzyme, and a Krüppel associated box domain; and (ii) a polynucleotide including a DNA-targeting sequence.

14 Claims, 24 Drawing Sheets

Specification includes a Sequence Listing.

Related U.S. Application Data

No. 17/073,588, filed on Oct. 19, 2020, now Pat. No. 11,434,491, which is a continuation of application No. PCT/US2019/028377, filed on Apr. 19, 2019.

(60) Provisional application No. 62/660,023, filed on Apr. 19, 2018.

(51) Int. Cl.
*C12N 9/10* (2006.01)
*C12N 9/22* (2006.01)
*C12N 15/113* (2010.01)
*C12N 15/63* (2006.01)

(52) U.S. Cl.
CPC ............ *C12N 15/113* (2013.01); *C12N 15/63* (2013.01); *C07K 2319/00* (2013.01); *C07K 2319/09* (2013.01); *C07K 2319/33* (2013.01); *C12N 9/22* (2013.01); *C12N 2310/20* (2017.05); *C12Y 201/01072* (2013.01); *C12Y 301/00* (2013.01)

(56) References Cited

U.S. PATENT DOCUMENTS

| | | | |
|---|---|---|---|
| 8,697,359 | B1 | 4/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,993,233 | B2 | 3/2015 | Zhang et al. |
| 8,999,641 | B2 | 4/2015 | Zhang et al. |
| 9,139,628 | B2 | 9/2015 | Minczuk et al. |
| 9,267,135 | B2 | 2/2016 | Church et al. |
| 9,322,006 | B2 | 4/2016 | Liu et al. |
| 9,526,784 | B2 | 12/2016 | Liu et al. |
| 9,771,601 | B2 | 9/2017 | May et al. |
| 9,840,713 | B2 | 12/2017 | Zhang |
| 9,850,500 | B2 | 12/2017 | Yun et al. |
| 10,266,850 | B2 | 4/2019 | Doudna et al. |
| 10,323,073 | B2 | 6/2019 | Tremblay et al. |
| 10,329,587 | B2 | 6/2019 | Church et al. |
| 10,378,027 | B2 | 8/2019 | Joung et al. |
| 10,443,076 | B2 | 10/2019 | Doudna et al. |
| 10,525,082 | B2 | 1/2020 | Crane et al. |
| 10,526,589 | B2 | 1/2020 | Tsai et al. |
| 10,570,378 | B2 | 2/2020 | Ji et al. |
| 10,583,201 | B2 | 3/2020 | Chen et al. |
| 10,604,752 | B2 | 3/2020 | Chen et al. |
| 10,612,044 | B2 | 4/2020 | Hatada et al. |
| 10,676,726 | B2 | 6/2020 | Gersbach et al. |
| 10,676,735 | B2 | 6/2020 | Gersbach et al. |
| 10,704,060 | B2 | 7/2020 | Gersbach et al. |
| 10,760,064 | B2 | 9/2020 | Joung et al. |
| 11,072,782 | B2 | 7/2021 | Cathomen et al. |
| 11,434,491 | B2 | 9/2022 | Chen et al. |
| 2007/0192880 | A1 | 8/2007 | Muyan et al. |
| 2009/0023153 | A1 | 1/2009 | Wolffe et al. |
| 2012/0207744 | A1 | 8/2012 | Mendlein et al. |
| 2014/0377868 | A1 | 12/2014 | Joung et al. |
| 2015/0191744 | A1 | 7/2015 | Wolfe et al. |
| 2015/0232883 | A1 | 8/2015 | Dahlman et al. |
| 2015/0247150 | A1 | 9/2015 | Zhang et al. |
| 2016/0010076 | A1 | 1/2016 | Joung et al. |
| 2016/0153005 | A1 | 6/2016 | Zhang et al. |
| 2016/0168594 | A1 | 6/2016 | Zhang et al. |
| 2016/0201089 | A1 | 7/2016 | Gersbach et al. |
| 2016/0298135 | A1 | 10/2016 | Chen et al. |
| 2016/0304872 | A1 | 10/2016 | Elowitz et al. |
| 2016/0319281 | A1 | 11/2016 | Tsai et al. |
| 2017/0191082 | A1 | 7/2017 | Chen et al. |
| 2017/0204407 | A1 | 7/2017 | Gilbert et al. |
| 2017/0219596 | A1 | 8/2017 | Tanenbaum et al. |
| 2017/0233762 | A1 | 8/2017 | Zalatan et al. |
| 2018/0030425 | A1 | 2/2018 | Joung et al. |
| 2018/0059373 | A1 | 3/2018 | Chen et al. |
| 2018/0216104 | A1 | 8/2018 | Abul-Husn et al. |
| 2018/0273976 | A1 | 9/2018 | Umit et al. |
| 2019/0010481 | A1 | 1/2019 | Joung et al. |
| 2019/0024072 | A1 | 1/2019 | Cathomen et al. |
| 2019/0024090 | A1 | 1/2019 | Cathomen et al. |
| 2019/0032049 | A1 | 1/2019 | Naldini et al. |
| 2019/0062739 | A1 | 2/2019 | Church et al. |
| 2019/0100732 | A1 | 4/2019 | Hellman et al. |
| 2019/0127713 | A1 | 5/2019 | Gersbach et al. |
| 2019/0194633 | A1 | 6/2019 | Gersbach et al. |
| 2019/0218261 | A1 | 7/2019 | Cheng et al. |
| 2019/0300868 | A1 | 10/2019 | Gilbert et al. |
| 2019/0328732 | A1 | 10/2019 | Deutzmann et al. |
| 2019/0343865 | A1 | 11/2019 | Jones et al. |
| 2019/0350938 | A1 | 11/2019 | Hoch et al. |
| 2019/0351074 | A1 | 11/2019 | Ahituv et al. |
| 2019/0376090 | A1 | 12/2019 | Joung et al. |
| 2019/0382752 | A1 | 12/2019 | Zeisberg et al. |
| 2020/0002710 | A1 | 1/2020 | Khalil et al. |
| 2020/0003761 | A1 | 1/2020 | Studer et al. |
| 2020/0071730 | A1 | 3/2020 | Joung et al. |
| 2020/0109406 | A1 | 4/2020 | Miller et al. |

FOREIGN PATENT DOCUMENTS

| | | | |
|---|---|---|---|
| WO | WO-2013/176772 | A1 | 11/2013 |
| WO | WO-2014/065596 | A1 | 5/2014 |
| WO | WO-2014/089290 | A1 | 6/2014 |
| WO | WO-2014/099744 | A1 | 6/2014 |
| WO | WO-2016/011080 | A2 | 1/2016 |
| WO | WO-2016/011080 | A3 | 1/2016 |
| WO | WO-2016/063264 | A1 | 4/2016 |
| WO | WO-2018/031762 | A1 | 2/2018 |
| WO | WO-2018/053035 | A1 | 3/2018 |
| WO | WO-2018/195540 | A1 | 10/2018 |
| WO | WO-2019/092507 | A2 | 5/2019 |
| WO | WO-2019/092507 | A3 | 5/2019 |
| WO | WO-2019/109051 | A1 | 6/2019 |
| WO | WO-2019/113061 | A1 | 6/2019 |
| WO | WO-2019/117660 | A2 | 6/2019 |
| WO | WO-2019/117660 | A3 | 6/2019 |
| WO | WO-2019/117662 | A2 | 6/2019 |
| WO | WO-2019/117662 | A3 | 6/2019 |
| WO | WO-2019/126799 | A1 | 6/2019 |
| WO | WO-2019/168950 | A1 | 9/2019 |
| WO | WO-2019/204503 | A1 | 10/2019 |
| WO | WO-2019/204766 | A1 | 10/2019 |
| WO | WO-2019/209869 | A2 | 10/2019 |
| WO | WO-2019/209869 | A3 | 10/2019 |
| WO | WO-2019/210279 | A1 | 10/2019 |
| WO | WO-2019/222437 | A1 | 11/2019 |
| WO | WO-2019/232069 | A1 | 12/2019 |
| WO | WO-2020/041679 | A1 | 2/2020 |
| WO | WO-2020/041679 | A4 | 2/2020 |
| WO | WO-2020/041776 | A1 | 2/2020 |
| WO | WO-2020/101042 | A1 | 5/2020 |
| WO | WO-2020/101042 | A8 | 5/2020 |

OTHER PUBLICATIONS

Georgios Vlachogiannis, et al. "The Dnmt3L ADD Domain Controls Cytosine Methylation Establishment during Spermatogenesis."

(56) References Cited

OTHER PUBLICATIONS

Cell Reports, vol. 10, No. 6, Feb. 1, 2015, pp. 944-956, https://doi.org/10.1016/j.celrep.2015.01.021. Accessed Sep. 9, 2023. (Year: 2015).*

Gordana Apic, et al. "Multi-Domain Protein Families and Domain Pairs: Comparison with Known Structures and a Random Model of Domain Recombination." Journal of Structural and Functional Genomics, vol. 4, No. 2/3, Jan. 1, 2003, pp. 67-78, https://doi.org/10.1023/a:1026113408773. Accessed Jan. 16, 2025. (Year: 2003).*

Ley, Timothy J., et al. "DNMT3AMutations in Acute Myeloid Leukemia." New England Journal of Medicine, vol. 363, No. 25, Dec. 16, 2010, pp. 2424-2433, https://doi.org/10.1056/nejmoa1005143. (Year: 2010).*

Park, Jong-Jin, et al. "RNA-Guided Transcriptional Activation via CRISPR/DCas9 Mimics Overexpression Phenotypes in *Arabidopsis*." PLOS ONE, vol. 12, No. 6, Jun. 16, 2017, p. e0179410, https://doi.org/10.1371/journal.pone.0179410. (Year: 2017).*

Peng, Hongzhuang, et al. "Epigenetic Gene Silencing by the SRY Protein Is Mediated by a KRAB-O Protein That Recruits the KAP1 Co-Repressor Machinery." Journal of Biological Chemistry, vol. 284, No. 51, Dec. 2009, pp. 35670-35680, https://doi.org/10.1074/jbc.m109.032086. Accessed Jul. 20, 2021. (Year: 2009).*

Swarts, Daan C., et al. "Structural Basis for Guide RNA Processing and Seed-Dependent DNA Targeting by CRISPR-Cas12a." Molecular Cell, vol. 66, No. 2, Apr. 2017, pp. 221-233.e4, https://doi.org/10.1016/j.molcel.2017.03.016. (Year: 2017).*

Yamano, Takashi, et al. "Structural Basis for the Canonical and Non-Canonical PAM Recognition by CRISPR-Cpf1." Molecular Cell, vol. 67, No. 4, Aug. 2017, pp. 633-645.e3, https://doi.org/10.1016/j.molcel.2017.06.035. Accessed Apr. 17, 2021. (Year: 2017).*

Adamson, B. et al. (Dec. 15, 2016). "A Multiplexed Single-Cell CRISPR Screening Platform Enables Systematic Dissection of the Unfolded Protein Response," *Cell* 167(7):1867-1882.e21.

Amabile, A. et al. (Sep. 22, 2016). "Inheritable Silencing of Endogenous Genes by Hit-and-Run Targeted Epigenetic Editing," *Cell* 167(1):219-232.

Braun, C.J. et al. (Jul. 5, 2016, e-published Jun. 20, 2016). "Versatile in vivo regulation of tumor phenotypes by dCas9-mediated transcriptional perturbation," *PNAS USA* 113(27):E3892-E3900.

Chen, B. et al. (Dec. 19, 2013). "Dynamic imaging of genomic loci in living human cells by an optimized CRISPR/Cas system," *Cell* 155(7):1479-1491.

Choudhury, S.R. et al. (Jul. 19, 2016). "CRISPR-dCas9 mediated TET1 targeting for selective DNA demethylation at BRCA1 promoter," *Oncotarget* 7(29):46545-46556.

Deans, R.M. et al. (May 2016, e-published Mar. 28, 2016). "Parallel shRNA and CRISPR-Cas9 screens enable antiviral drug target identification," *Nat Chem Biol* 12(5):361-366.

Deuschle U. et al. (Apr. 1995). "Tetracycline-reversible silencing of eukaryotic promoters," *Mol Cell Biol.* 15(4):1907-1914.

Ecco, G. et al. (Aug. 1, 2017). "KRAB zinc finger proteins," *Development* 144(15):2719-2729.

Extended European Search Report dated Jan. 4, 2022, for EP Patent Application No. 19789200.3, 9 pages.

Gilbert, L.A. et al. (Jul. 18, 2013, e-published Jul. 11, 2013). "CRISPR-mediated modular RNA-guided regulation of transcription in eukaryotes," *Cell* 154(2):442-451.

Gilbert, L.A. et al. (Oct. 23, 2014, e-published Oct. 9, 2014). "Genome-Scale CRISPR-Mediated Control of Gene Repression and Activation," *Cell* 159(3):647-661.

Gowher, H. et al. (Apr. 8, 2005, e-published Jan. 24, 2005). "Mechanism of Stimulation of Catalytic Activity of Dnmt3A and Dnmt3B DNA-(Cytosine-C5)-methyltransferases by Dnmt3L", *The Journal of Biological Chemistry*, 280(14):13341-13348.

Guilinger, J.P. et al. (Apr. 25, 2014). "Fusion of catalytically inactive Cas9 to FokI nuclease improves the specificity of genome modification," *Nature Biotechnology* 32(6): 577-582.

Horlbeck, M.A. et al. (2016). "Compact and highly active next-generation libraries for CRISPR-mediated gene repression and activation," *eLife* 5:e19760.

Horlbeck, M.A. et al. (2016). "Nucleosomes impede Cas9 access to DNA in vivo and in vitro," *eLife* 5:e12677.

International Search Report mailed on Sep. 10, 2019, for PCT/US2019/028377, filed Apr. 19, 2019, 6 pages.

Kearns, N.A. et al. (Jan. 2014). "Cas9 effector-mediated regulation of transcription and differentiation in human pluripotent stem cells," *Development* 141(1):219-223.

Kocak, D. D. (2013). "Synthetic Transcription Factors and their Effects on Endogenous DNA Methylation in Human Cells," [Unpublished Master's Thesis]. Duke University. Located at https://dukespace.lib.duke.edu/dspace/bitstream/handle/10161/8802/Kocak_duke_0066N_12237.pdf?sequence=1, 35 pages.

Larson, M.H. et al. (Nov. 2013, e-published Oct. 17, 2013). "CRISPR interference (CRISPRi) for sequence-specific control of gene expression," *Nat Protoc* 8(11):2180-2196.

Li, H. et al. (Jul. 14, 2006, e-published May 8, 2006). "The Histone Methyltransferase SETDB1 and the DNA Methyltransferase DNMT3A Interact Directly and Localize to Promoters Silenced in Cancer Cells," *The Journal of Biological Chemistry* 281(28):19489-19500.

Lin, L. et al. (Mar. 1, 2018). "Genome-wide determination of on-target and off-target characteristics for RNA-guided DNA methylation by dCas9 methyltransferases," *Gigascience* 7(3):1-19.

Liu, X.S. et al. Sep. 22, 2016). "Editing DNA Methylation in the Mammalian Genome," *Cell* 167(1):233-247.e17.

Liu, S.J. et al. (Jan. 6, 2017, e-published Dec. 15, 2016). "CRISPRi-based genome-scale identification of functional long noncoding RNA loci in human cells," *Science* 355(6320):aah7111.

Mandegar, M.A. et al. (Apr. 7, 2016, e-published Mar. 10, 2016). "CRISPR Interference Efficiently Induces Specific and Reversible Gene Silencing in Human iPSCs," *Cell Stem Cell* 18(4):541-553.

Mlambo, T. et al. (May 18, 2018). "Designer epigenome modifiers enable robust and sustained gene silencing in clinically relevant human cells," *Nucleic Acids Res* 46(9):4456-4468.

Nemudryi, A.A. et al. (Jul. 2014). "TALEN and CRISPR/Cas Genome Editing Systems: Tools of Discovery," *Acta Naturae* 6(3):19-40.

Nguyen, D.P. et al. (Jul. 1, 2016). "Ligand-binding domains of nuclear receptors facilitate tight control of split CRISPR activity," *Nat Commun* 7:12009.

O'Geen, H. et al. (Sep. 29, 2017). "dCas9-based epigenome editing suggests acquisition of histone methylation is not sufficient for target gene repression," *Nucleic Acids Research* 45(17):9901-9916.

O'Geen, H. et al. (Apr. 8, 2022). "Determinants of heritable gene silencing for KRAB-dCas9 + DNMT3 and Ezh2-dCas9 + DNMT3 hit-and-run epigenome editing," *Nucleic Acids Res* 50(6):3239-3253.

Qi, L.S. et al. (Feb. 28, 2013). "Repurposing CRISPR as an RNA-guided platform for sequence-specific control of gene expression," *Cell* 152(5):1173-1183.

Rivenbark, A.G. et al. (Apr. 2012). "Epigenetic reprogramming of cancer cells via targeted DNA methylation," *Epigenetics* 7(4):350-360.

Schellenberger, V. et al. (Dec. 2009). "A recombinant polypeptide extends the in vivo half-life of peptides and proteins in a tunable manner," *Nature Biotechnology* 27(12):1186-1190.

Siddique, A.N. et al. (Feb. 8, 2013, e-published Dec. 4, 2012). "Targeted methylation and gene silencing of VEGF-A in human cells by using a designed Dnmt3a-Dnmt3L single-chain fusion protein with increased DNA methylation activity," *J Mol Biol* 425(3):479-491.

Stepper, P. et al. (Feb. 28, 2017, e-published Nov. 28, 2016). "Efficient targeted DNA methylation with chimeric dCas9-Dnmt3a-Dnmt3L methyltransferase," *Nucleic Acids Res* 45(4):1703-1713.

Vojta, A. et al. (Jul. 8, 2016, e-published Mar. 11, 2016). "Repurposing the CRISPR-Cas9 system for targeted DNA methylation," *Nucleic Acids Research* 44(12):5615-5628.

Wilson, R.C. et al. (Feb. 16, 2018, e-published Oct. 19, 2017). "The Promise and Challenge of In Vivo Delivery for Genome Therapeutics," *ACS Chem Biol* 13(2):376-382.

(56) References Cited

OTHER PUBLICATIONS

Written Opinion mailed on Sep. 10, 2019, for PCT/US2019/028377, filed Apr. 19, 2019, 10 pages.
Zalatan, J.G. et al. (Jan. 15, 2015, e-published Dec. 18, 2014). "Engineering complex synthetic transcriptional programs with CRISPR RNA scaffolds," *Cell* 160(1-2):339-350.
Zhang Z. et al. (Aug. 15, 2013). "Dissecting the roles of miR-302/367 cluster in cellular reprogramming using TALE-based repressor and TALEN," *Stem Cell Reports* 1(3):218-225.
Jinek, M. et al. (Aug. 17, 2012). "A programmable dual-RNA-guided DNA endonuclease in adaptive bacterial immunity," *Science* 337(6096):816-821.
Lupo, A. et al. (Jun. 2013). "KRAB-Zinc Finger Proteins: A Repressor Family Displaying Multiple Biological Functions," *Curr Genomics* 4(4):268-278.
Petrossian, T. (Oct. 1, 2009). "Bioinformatic Identification of Novel Methyltransferases," *Epigenomics* 1(1):163-175.
Miao, C. et al. (Apr. 9, 2018). "Systematically investigating the key features of the nuclease deactivated Cpf1 for tunable multiplex genetic regulation," *bioRxiv* No. 297903; doi: doi.org/10.1101/297903.
Zetsche, B. et al. (Oct. 22, 2015). "Cpf1 is a single RNA-guided endonuclease of a class 2 CRISPR-Cas system," *Cell* 163(3):759-771.
Zhang, X. et al. (Jun. 6, 2017). "Multiplex gene regulation by CRISPR-ddCpf1," *Cell Discov* 3:17018.
Zhang, X. et al. (Apr. 2018). "Gene activation in human cells using CRISPR/Cpf1-p300 and CRISPR/Cpf1-SunTag systems," *Protein Cell* 9(4):380-383, and S1-S8.

* cited by examiner

FIG. 13B
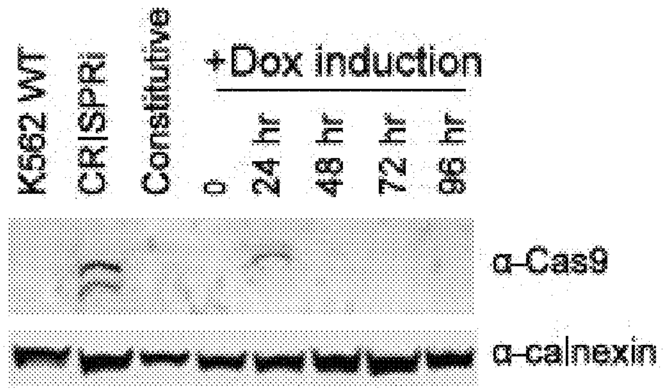
FIG. 13C
FIG. 13D
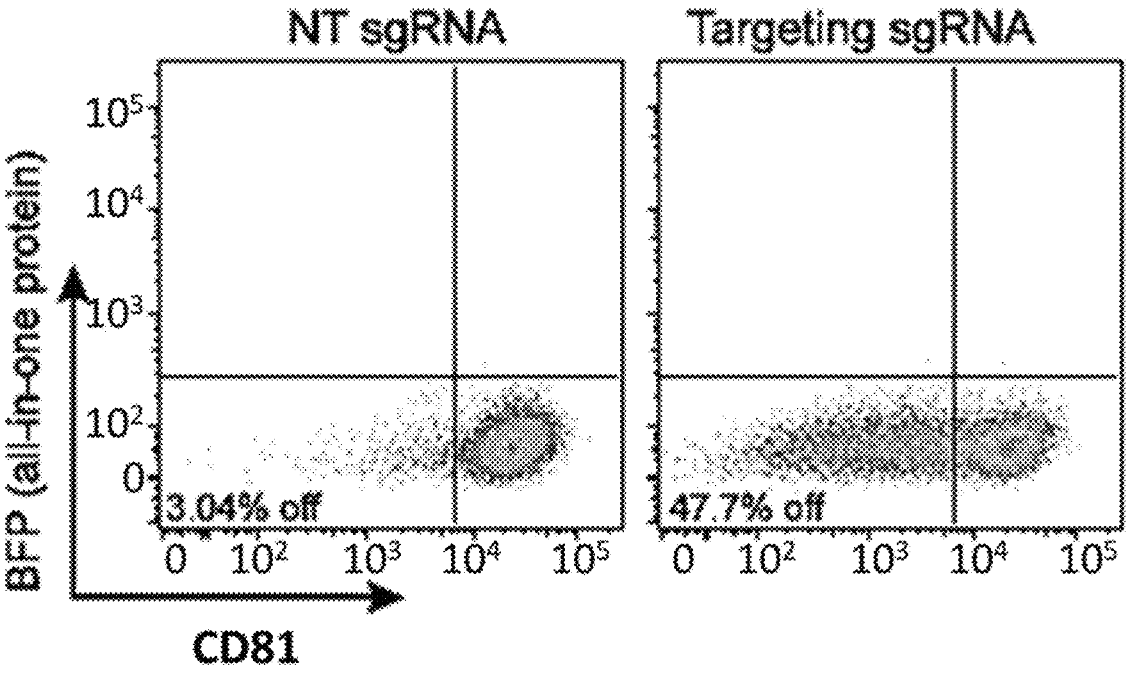

FIG. 13E
FIG. 13F
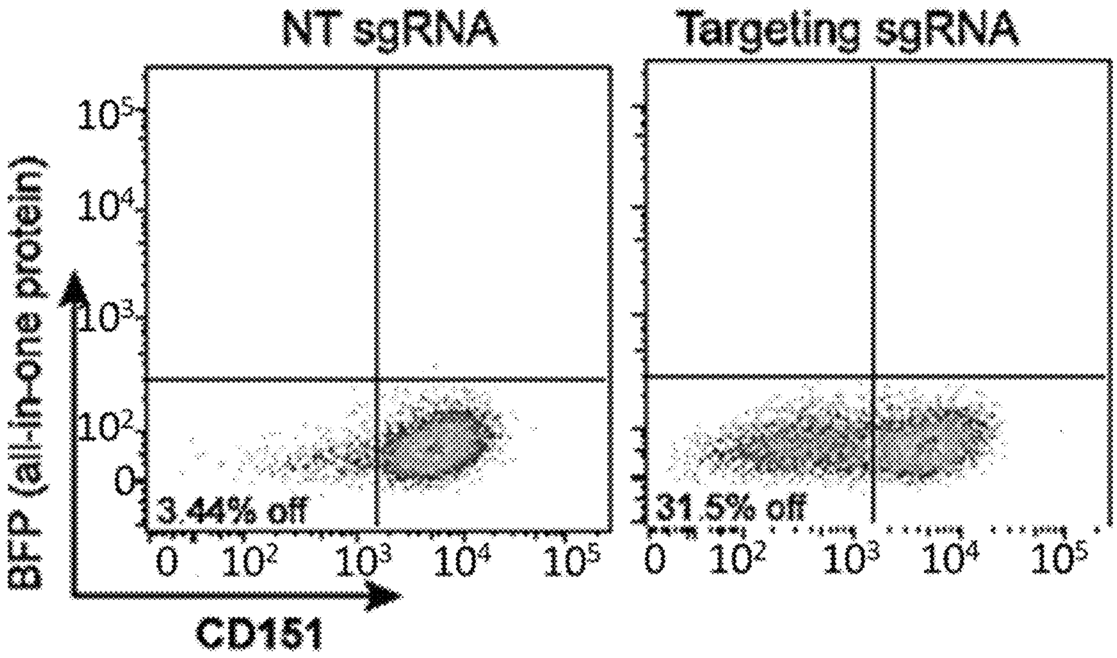
FIG. 13G
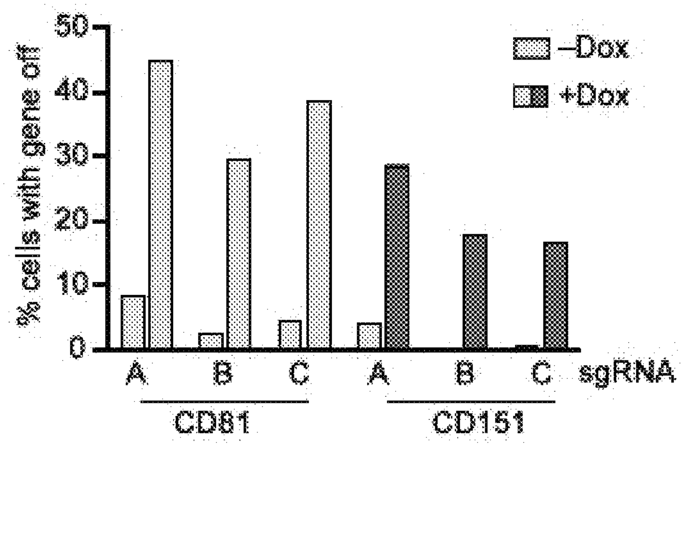

SEQUENCE LISTING

```
Sequence total quantity: 96
SEQ ID NO: 1          moltype = AA  length = 2294
FEATURE               Location/Qualifiers
REGION                1..2294
                      note = Synthetic polypeptide
source                1..2294
```

```
                        mol_type = protein
                        organism = synthetic construct
SEQUENCE: 1
DAKSLTAWSR TLVTFKDVFV DFTREEWKLL DTAQQIVYRN VMLENYKNLV SLGYQLTKPD  60
VILRLEKGEE PGGSGGGSMD KKYSIGLAIG TNSVGWAVIT DEYKVPSKKF KVLGNTDRHS  120
IKKNLIGALL FDSGETAEAT RLKRTARRRY TRRKNRICYL QEIFSNEMAK VDDSFFHRLE  180
ESFLVEEDKK HERHPIFGNI VDEVAYHEKY PTIYHLRKKL VDSTDKADLR LIYLALAHMI  240
KFRGHFLIEG DLNPDNSDVD KLFIQLVQTY NQLFEENPIN ASGVDAKAIL SARLSKSRRL  300
ENLIAQLPGE KKNGLFGNLI ALSLGLTPNF KSNFDLAEDA KLQLSKDTYD DDLDNLLAQI  360
GDQYADLFLA AKNLSDAILL SDILRVNTEI TKAPLSASMI KRYDEHHQDL TLLKALVRQQ  420
LPEKYKEIFF DQSKNGYAGY IDGGASQEEF YKFIKPILEK MDGTEELLVK LNREDLLRKQ  480
RTFDNGSIPH QIHLGELHAI LRRQEDFYPF LKDNREKIEK ILTFRIPYYV GPLARGNSRF  540
AWMTRKSEET ITPWNFEEVV DKGASAQSFI ERMTNFDKNL PNEKVLPKHS LLYEYFTVYN  600
ELTKVKYVTE GMRKPAFLSG EQKKAIVDLL FKTNRKVTVK QLKEDYFKKI ECFDSVEISG  660
VEDRFNASLG TYHDLLKIIK DKDFLDNEEN EDILEDIVLT LTLFEDREMI EERLKTYAHL  720
FDDKVMKQLK RRRYTGWGRL SRKLINGIRD KQSGKTILDF LKSDGFANRN FMQLIHDDSL  780
TFKEDIQKAQ VSGQGDSLHE HIANLAGSPA IKKGILQTVK VVDELVKVMG RHKPENIVIE  840
MARENQTTQK GQKNSRERMK RIEEGIKELG SQILKEHPVE NTQLQNEKLY LYYLQNGRDM  900
YVDQELDINR LSDYDVDAIV PQSFLKDDSI DNKVLTRSDK NRGKSDNVPS EEVVKKMKNY  960
WRQLLNAKLI TQRKFDNLTK AERGGLSELD KAGFIKRQLV ETRQITKHVA QILDSRMNTK  1020
YDENDKLIRE VKVITLKSKL VSDFRKDFQF YKVREINNYH HAHDAYLNAV VGTALIKKYP  1080
KLESEFVYGD YKVYDVRKMI AKSEQEIGKA TAKYFFYSNI MNFFKTEITL ANGEIRKRPL  1140
IETNGETGEI VWDKGRDFAT VRKVLSMPQV NIVKKTEVQT GGFSKESILP KRNSDKLIAR  1200
KKDWDPKKYG GFDSPTVAYS VLVVAKVEKG KSKKLKSVKE LLGITIMERS SFEKNPIDFL  1260
EAKGYKEVKK DLIIKLPKYS LFELENGRKR MLASAGELQK GNELALPSKY VNFLYLASHY  1320
EKLKGSPEDN EQKQLFVEQH KHYLDEIIEQ ISEFSKRVIL ADANLDKVLS AYNKHRDKPI  1380
REQAENIIHL FTLTNLGAPA AFKYFDTTID RKRYTSTKEV LDATLIHQSI TGLYETRIDL  1440
SQLGGDSRAD YPYDVPDYAS GSPKKKRKVE ASGSGRASPG IPGSTRNHDQ EFDPPKVYPP  1500
VPAEKRKPIR VLSLFDGIAT GLLVLKDLGI QVDRYIASEV CEDSITVGMV RHQGKIMYVG  1560
DVRSVTQKHI QEWGPFDLVI GGSPCNDLSI VNPARKGLYE GTGRLFFEFY RLLHDARPKE  1620
GDDRPFFWLF ENVVAMGVSD KRDISRFLES NPVMIDAKEV SAAHRARYFW GNLPGMNRPL  1680
ASTVNDKLEL QECLEHGRIA KFSKVRTITT RSNSIKQGKD QHFPVFMNEK EDILWCTEME  1740
RVFGFPVHYT DVSNMSRLAR QRLLGRSWSV PVIRHLFAPL KEYFACVSSG NSNANSRGPS  1800
FSSGLVPLSL RGSHMGPMEI YKTVSAWKRQ PVRVLSLFRN IDKVLKSLGF LESGSGSGGG  1860
TLKYVEDVTN VVRRDVEKWG PFDLVYGSTQ PLGSSCDRCP GWYMFQFHRI LQYALPRQES  1920
QRPFFWIFMD NLLLTEDDQE TTTRFLQTEA VTLQDVRGRD YQNAMRVWSN IPGLKSKHAP  1980
LTPKEEEYLQ AQVRSRSKLD APKVDLLVKN CLLPLREYFK YFSQNSLPLS RADPKKKRKV  2040
GSGATNFSLL KQAGDVEENP GPSELIKENM HMKLYMEGTV DNHHFKCTSE GEGKPYEGTQ  2100
TMRIKVVEGG PLPFAFDILA TSFLYGSKTF INHTQGIPDF FKQSFPEGFT WERVTTYEDG  2160
GVLTATQDTS LQDGCLIYNV KIRGVNFTSN GPVMQKKTLG WEAFTETLYP ADGGLEGRND  2220
MALKLVGGSH LIANIKTTYR SKKPAKNLKM PGVYYVDYRL ERIKEANNET YVEQHEVAVA  2280
RYCDLPSKLG HKLN                                                   2294

SEQ ID NO: 2            moltype = AA  length = 2296
FEATURE                 Location/Qualifiers
REGION                  1..2296
                        note = Synthetic polypeptide
source                  1..2296
                        mol_type = protein
                        organism = synthetic construct
SEQUENCE: 2
DAKSLTAWSR TLVTFKDVFV DFTREEWKLL DTAQQIVYRN VMLENYKNLV SLGYQLTKPD  60
VILRLEKGEE PGGSGGGSMD KKYSIGLAIG TNSVGWAVIT DEYKVPSKKF KVLGNTDRHS  120
IKKNLIGALL FDSGETAEAT RLKRTARRRY TRRKNRICYL QEIFSNEMAK VDDSFFHRLE  180
ESFLVEEDKK HERHPIFGNI VDEVAYHEKY PTIYHLRKKL VDSTDKADLR LIYLALAHMI  240
KFRGHFLIEG DLNPDNSDVD KLFIQLVQTY NQLFEENPIN ASGVDAKAIL SARLSKSRRL  300
ENLIAQLPGE KKNGLFGNLI ALSLGLTPNF KSNFDLAEDA KLQLSKDTYD DDLDNLLAQI  360
GDQYADLFLA AKNLSDAILL SDILRVNTEI TKAPLSASMI KRYDEHHQDL TLLKALVRQQ  420
LPEKYKEIFF DQSKNGYAGY IDGGASQEEF YKFIKPILEK MDGTEELLVK LNREDLLRKQ  480
RTFDNGSIPH QIHLGELHAI LRRQEDFYPF LKDNREKIEK ILTFRIPYYV GPLARGNSRF  540
AWMTRKSEET ITPWNFEEVV DKGASAQSFI ERMTNFDKNL PNEKVLPKHS LLYEYFTVYN  600
ELTKVKYVTE GMRKPAFLSG EQKKAIVDLL FKTNRKVTVK QLKEDYFKKI ECFDSVEISG  660
VEDRFNASLG TYHDLLKIIK DKDFLDNEEN EDILEDIVLT LTLFEDREMI EERLKTYAHL  720
FDDKVMKQLK RRRYTGWGRL SRKLINGIRD KQSGKTILDF LKSDGFANRN FMQLIHDDSL  780
TFKEDIQKAQ VSGQGDSLHE HIANLAGSPA IKKGILQTVK VVDELVKVMG RHKPENIVIE  840
MARENQTTQK GQKNSRERMK RIEEGIKELG SQILKEHPVE NTQLQNEKLY LYYLQNGRDM  900
YVDQELDINR LSDYDVDAIV PQSFLKDDSI DNKVLTRSDK NRGKSDNVPS EEVVKKMKNY  960
WRQLLNAKLI TQRKFDNLTK AERGGLSELD KAGFIKRQLV ETRQITKHVA QILDSRMNTK  1020
YDENDKLIRE VKVITLKSKL VSDFRKDFQF YKVREINNYH HAHDAYLNAV VGTALIKKYP  1080
KLESEFVYGD YKVYDVRKMI AKSEQEIGKA TAKYFFYSNI MNFFKTEITL ANGEIRKRPL  1140
IETNGETGEI VWDKGRDFAT VRKVLSMPQV NIVKKTEVQT GGFSKESILP KRNSDKLIAR  1200
KKDWDPKKYG GFDSPTVAYS VLVVAKVEKG KSKKLKSVKE LLGITIMERS SFEKNPIDFL  1260
EAKGYKEVKK DLIIKLPKYS LFELENGRKR MLASAGELQK GNELALPSKY VNFLYLASHY  1320
EKLKGSPEDN EQKQLFVEQH KHYLDEIIEQ ISEFSKRVIL ADANLDKVLS AYNKHRDKPI  1380
REQAENIIHL FTLTNLGAPA AFKYFDTTID RKRYTSTKEV LDATLIHQSI TGLYETRIDL  1440
SQLGGDSRAD YPYDVPDYAS GSPKKKRKVS PGSGSETPGT SESATPESNH DQEFDPPKVY  1500
PPVPAEKRKP IRVLSLFDGI ATGLLVLKDL GIQVDRYIAS EVCEDSITVG MVRHQGKIMY  1560
VGDVRSVTQK HIQEWGPFDL VIGGSPCNDL SIVNPARKGL YEGTGRLFFE FYRLLHDARP  1620
KEGDDRPFFW LFENVVAMGV SDKRDISRFL ESNPVMIDAK EVSAAHRARY FWGNLPGMNR  1680
```

```
PLASTVNDKL ELQECLEHGR IAKFSKVRTI TTRSNSIKQG KDQHFPVFMN EKEDILWCTE  1740
MERVFGFPVH YTDVSNMSRL ARQRLLGRSW SVPVIRHLFA PLKEYFACVS SGNSNANSRG  1800
PSFSSGLVPL SLRGSHMGPM EIYKTVSAWK RQPVRVLSLF RNIDKVLKSL GFLESGSGSG  1860
GGTLKYVEDV TNVVRRDVEK WGPFDLVYGS TQPLGSSCDR CPGWYMFQFH RILQYALPRQ  1920
ESQRPFFWIF MDNLLLTEDD QETTTRFLQT EAVTLQDVRG RDYQNAMRVW SNIPGLKSKH  1980
APLTPKEEEY LQAQVRSRSK LDAPKVDLLV KNCLLPLREY FKYFSQNSLP LSRADPKKKR  2040
KVGSGATNFS LLKQAGDVEE NPGPSELIKE NMHMKLYMEG TVDNHHFKCT SEGEGKPYEG  2100
TQTMRIKVVE GGPLPFAFDI LATSFLYGSK TFINHTQGIP DFFKQSFPEG FTWERVTTYE  2160
DGGVLTATQD TSLQDGCLIY NVKIRGVNFT SNGPVMQKKT LGWEAFTETL YPADGGLEGR  2220
NDMALKLVGG SHLIANIKTT YRSKKPAKNL KMPGVYYVDY RLERIKEANN ETYVEQHEVA  2280
VARYCDLPSK LGHKLN                                                 2296

SEQ ID NO: 3            moltype = AA  length = 2316
FEATURE                 Location/Qualifiers
REGION                  1..2316
                        note = Synthetic polypeptide
source                  1..2316
                        mol_type = protein
                        organism = synthetic construct
SEQUENCE: 3
DAKSLTAWSR TLVTFKDVFV DFTREEWKLL DTAQQIVYRN VMLENYKNLV SLGYQLTKPD  60
VILRLEKGEE PGGSGGGSMD KKYSIGLAIG TNSVGWAVIT DEYKVPSKKF KVLGNTDRHS  120
IKKNLIGALL FDSGETAEAT RLKRTARRRY TRRKNRICYL QEIFSNEMAK VDDSFFHRLE  180
ESFLVEEDKK HERHPIFGNI VDEVAYHEKY PTIYHLRKKL VDSTDKADLR LIYLALAHMI  240
KFRGHFLIEG DLNPDNSDVD KLFIQLVQTY NQLFEENPIN ASGVDAKAIL SARLSKSRRL  300
ENLIAQLPGE KKNGLFGNLI ALSLGLTPNF KSNFDLAEDA KLQLSKDTYD DDLDNLLAQI  360
GDQYADLFLA AKNLSDAILL SDILRVNTEI TKAPLSASMI KRYDEHHQDL TLLKALVRQQ  420
LPEKYKEIFF DQSKNGYAGY IDGGASQEEF YKFIKPILEK MDGTEELLVK LNREDLLRKQ  480
RTFDNGSIPH QIHLGELHAI LRRQEDFYPF LKDNREKIEK ILTFRIPYYV GPLARGNSRF  540
AWMTRKSEET ITPWNFEEVV DKGASAQSFI ERMTNFDKNL PNEKVLPKHS LLYEYFTVYN  600
ELTKVKYVTE GMRKPAFLSG EQKKAIVDLL FKTNRKVTVK QLKEDYFKKI ECFDSVEISG  660
VEDRFNASLG TYHDLLKIIK DKDFLDNEEN EDILEDIVLT LTLFEDREMI EERLKTYAHL  720
FDDKVMKQLK RRRYTGWGRL SRKLINGIRD KQSGKTILDF LKSDGFANRN FMQLIHDDSL  780
TFKEDIQKAQ VSGQGDSLHE HIANLAGSPA IKKGILQTVK VVDELVKVMG RHKPENIVIE  840
MARENQTTQK GQKNSRERMK RIEEGIKELG SQILKEHPVE NTQLQNEKLY LYYLQNGRDM  900
YVDQELDINR LSDYDVDAIV PQSFLKDDSI DNKVLTRSDK NRGKSDNVPS EEVVKKMKNY  960
WRQLLNAKLI TQRKFDNLTK AERGGLSELD KAGFIKRQLV ETRQITKHVA QILDSRMNTK  1020
YDENDKLIRE VKVITLKSKL VSDFRKDFQF YKVREINNYH HAHDAYLNAV VGTALIKKYP  1080
KLESEFVYGD YKVYDVRKMI AKSEQEIGKA TAKYFFYSNI MNFFKTEITL ANGEIRKRPL  1140
IETNGETGEI VWDKGRDFAT VRKVLSMPQV NIVKKTEVQT GGFSKESILP KRNSDKLIAR  1200
KKDWDPKKYG GFDSPTVAYS VLVVAKVEKG KSKKLKSVKE LLGITIMERS SFEKNPIDFL  1260
EAKGYKEVKK DLIIKLPKYS LFELENGRKR MLASAGELQK GNELALPSKY VNFLYLASHY  1320
EKLKGSPEDN EQKQLFVEQH KHYLDEIIEQ ISEFSKRVIL ADANLDKVLS AYNKHRDKPI  1380
REQAENIIHL FTLTNLGAPA AFKYFDTTID RKRYTSTKEV LDATLIHQSI TGLYETRIDL  1440
SQLGGDSRAD YPYDVPDYAS GSPKKKRKVE ASGSGRASPG IPGSTRNHDQ EFDPPKVYPP  1500
VPAEKRKPIR VLSLFDGIAT GLLVLKDLGI QVDRYIASEV CEDSITVGMV RHQGKIMYVG  1560
DVRSVTQKHI QEWGPFDLVI GGSPCNDLSI VNPARKGLYE GTGRLFFEFY RLLHDARPKE  1620
GDDRPFFWLF ENVVAMGVSD KRDISRFLES NPVMIDAKEV SAAHRARYFW GNLPGMNRPL  1680
ASTVNDKLEL QECLEHGRIA KFSKVRTITT RSNSIKQGKD QHFPVFMNEK EDILWCTEME  1740
RVFGFPVHYT DVSNMSRLAR QRLLGRSWSV PVIRHLFAPL KEYFACVSSG NSNANSRGPS  1800
FSSGLVPLSL RGSHMGPMEI YKTVSAWKRQ PVRVLSLFRN IDKVLKSLGF LESGSGSGGG  1860
TLKYVEDVTN VVRRDVEKWG PFDLVYGSTQ PLGSSCDRCP GWYMFQFHRI LQYALPRQES  1920
QRPFFWIFMD NLLLTEDDQE TTTRFLQTEA VTLQDVRGRD YQNAMRVWSN IPGLKSKHAP  1980
LTPKEEEYLQ AQVRSRSKLD APKVDLLVKN CLLPLREYFK YFSQNSLPLS RADPKKKRKV  2040
GSGATNFSLL KQAGDVEENP GPGSGATNFS LLKQAGDVEE NPGPSELIKE NMHMKLYMEG  2100
TVDNHHFKCT SEGEGKPYEG TQTMRIKVVE GGPLPFAFDI LATSFLYGSK TFINHTQGIP  2160
DFFKQSFPEG FTWERVTTYE DGGVLTATQD TSLQDGCLIY NVKIRGVNFT SNGPVMQKKT  2220
LGWEAFTETL YPADGGLEGR NDMALKLVGG SHLIANIKTT YRSKKPAKNL KMPGVYYVDY  2280
RLERIKEANN ETYVEQHEVA VARYCDLPSK LGHKLN                           2316

SEQ ID NO: 4            moltype = AA  length = 2318
FEATURE                 Location/Qualifiers
REGION                  1..2318
                        note = Synthetic polypeptide
source                  1..2318
                        mol_type = protein
                        organism = synthetic construct
SEQUENCE: 4
DAKSLTAWSR TLVTFKDVFV DFTREEWKLL DTAQQIVYRN VMLENYKNLV SLGYQLTKPD  60
VILRLEKGEE PGGSGGGSMD KKYSIGLAIG TNSVGWAVIT DEYKVPSKKF KVLGNTDRHS  120
IKKNLIGALL FDSGETAEAT RLKRTARRRY TRRKNRICYL QEIFSNEMAK VDDSFFHRLE  180
ESFLVEEDKK HERHPIFGNI VDEVAYHEKY PTIYHLRKKL VDSTDKADLR LIYLALAHMI  240
KFRGHFLIEG DLNPDNSDVD KLFIQLVQTY NQLFEENPIN ASGVDAKAIL SARLSKSRRL  300
ENLIAQLPGE KKNGLFGNLI ALSLGLTPNF KSNFDLAEDA KLQLSKDTYD DDLDNLLAQI  360
GDQYADLFLA AKNLSDAILL SDILRVNTEI TKAPLSASMI KRYDEHHQDL TLLKALVRQQ  420
LPEKYKEIFF DQSKNGYAGY IDGGASQEEF YKFIKPILEK MDGTEELLVK LNREDLLRKQ  480
RTFDNGSIPH QIHLGELHAI LRRQEDFYPF LKDNREKIEK ILTFRIPYYV GPLARGNSRF  540
AWMTRKSEET ITPWNFEEVV DKGASAQSFI ERMTNFDKNL PNEKVLPKHS LLYEYFTVYN  600
ELTKVKYVTE GMRKPAFLSG EQKKAIVDLL FKTNRKVTVK QLKEDYFKKI ECFDSVEISG  660
```

-continued

```
VEDRFNASLG TYHDLLKIIK DKDFLDNEEN EDILEDIVLT LTLFEDREMI EERLKTYAHL  720
FDDKVMKQLK RRRYTGWGRL SRKLINGIRD KQSGKTILDF LKSDGFANRN FMQLIHDDSL  780
TFKEDIQKAQ VSGQGDSLHE HIANLAGSPA IKKGILQTVK VVDELVKVMG RHKPENIVIE  840
MARENQTTQK GQKNSRERMK RIEEGIKELG SQILKEHPVE NTQLQNEKLY LYYLQNGRDM  900
YVDQELDINR LSDYDVDAIV PQSFLKDDSI DNKVLTRSDK NRGKSDNVPS EEVVKKMKNY  960
WRQLLNAKLI TQRKFDNLTK AERGGLSELD KAGFIKRQLV ETRQITKHVA QILDSRMNTK  1020
YDENDKLIRE VKVITLKSKL VSDFRKDFQF YKVREINNYH HAHDAYLNAV VGTALIKKYP  1080
KLESEFVYGD YKVYDVRKMI AKSEQEIGKA TAKYFFYSNI MNFFKTEITL ANGEIRKRPL  1140
IETNGETGEI VWDKGRDFAT VRKVLSMPQV NIVKKTEVQT GGFSKESILP KRNSDKLIAR  1200
KKDWDPKKYG GFDSPTVAYS VLVVAKVEKG KSKKLKSVKE LLGITIMERS SFEKNPIDFL  1260
EAKGYKEVKK DLIIKLPKYS LFELENGRKR MLASAGELQK GNELALPSKY VNFLYLASHY  1320
EKLKGSPEDN EQKQLFVEQH KHYLDEIIEQ ISEFSKRVIL ADANLDKVLS AYNKHRDKPI  1380
REQAENIIHL FTLTNLGAPA AFKYFDTTID RKRYTSTKEV LDATLIHQSI TGLYETRIDL  1440
SQLGGDSRAD YPYDVPDYAS GSPKKKRKVS PGSGSETPGT SESATPESNH DQEFDPPKVY  1500
PPVPAEKRKP IRVLSLFDGI ATGLLVLKDL GIQVDRYIAS EVCEDSITVG MVRHQGKIMY  1560
VGDVRSVTQK HIQEWGPFDL VIGGSPCNDL SIVNPARKGL YEGTGRLFFE FYRLLHDARP  1620
KEGDDRPFFW LFENVVAMGV SDKRDISRFL ESNPVMIDAK EVSAAHRARY FWGNLPGMNR  1680
PLASTVNDKL ELQECLEHGR IAKFSKVRTI TTRSNSIKQG KDQHFPVFMN EKEDILWCTE  1740
MERVFGFPVH YTDVSNMSRL ARQRLLGRSW SVPVIRHLFA PLKEYFACVS SGNSNANSRG  1800
PSFSSGLVPL SLRGSHMGPM EIYKTVSAWK RQPVRVLSLF RNIDKVLKSL GFLESGSGSG  1860
GGTLKYVEDV TNVVRRDVEK WGPFDLVYGS TQPLGSSCDR CPGWYMFQFH RILQYALPRQ  1920
ESQRPFFWIF MDNLLLTEDD QETTTRFLQT EAVTLQDVRG RDYQNAMRVW SNIPGLKSKH  1980
APLTPKEEEY LQAQVRSRSK LDAPKVDLLV KNCLLPLREY FKYFSQNSLP LSRADPKKKR  2040
KVGSGATNFS LLKQAGDVEE NPGPGSGATN FSLLKQAGDV EENPGPSELI KENMHMKLYM  2100
EGTVDNHHFK CTSEGEGKPY EGTQTMRIKV VEGGPLPFAF DILATSFLYG SKTFINHTQG  2160
IPDFFKQSFP EGFTWERVTT YEDGGVLTAT QDTSLQDGCL IYNVKIRGVN FTSNGPVMQK  2220
KTLGWEAFTE TLYPADGGLE GRNDMALKLV GGSHLIANIK TTYRSKKPAK NLKMPGVYYV  2280
DYRLERIKEA NNETYVEQHE VAVARYCDLP SKLGHKLN                        2318

SEQ ID NO: 5           moltype = AA  length = 2360
FEATURE                Location/Qualifiers
REGION                 1..2360
                       note = Synthetic polypeptide
source                 1..2360
                       mol_type = protein
                       organism = synthetic construct
SEQUENCE: 5
DAKSLTAWSR TLVTFKDVFV DFTREEWKLL DTAQQIVYRN VMLENYKNLV SLGYQLTKPD  60
VILRLEKGEE PGGSGGGSMD KKYSIGLAIG TNSVGWAVIT DEYKVPSKKF KVLGNTDRHS  120
IKKNLIGALL FDSGETAEAT RLKRTARRRY TRRKNRICYL QEIFSNEMAK VDDSFFHRLE  180
ESFLVEEDKK HERHPIFGNI VDEVAYHEKY PTIYHLRKKL VDSTDKADLR LIYLALAHMI  240
KFRGHFLIEG DLNPDNSDVD KLFIQLVQTY NQLFEENPIN ASGVDAKAIL SARLSKSRRL  300
ENLIAQLPGE KKNGLFGNLI ALSLGLTPNF KSNFDLAEDA KLQLSKDTYD DDLDNLLAQI  360
GDQYADLFLA AKNLSDAILL SDILRVNTEI TKAPLSASMI KRYDEHHQDL TLLKALVRQQ  420
LPEKYKEIFF DQSKNGYAGY IDGGASQEEF YKFIKPILEK MDGTEELLVK LNREDLLRKQ  480
RTFDNGSIPH QIHLGELHAI LRRQEDFYPF LKDNREKIEK ILTFRIPYYV GPLARGNSRF  540
AWMTRKSEET ITPWNFEEVV DKGASAQSFI ERMTNFDKNL PNEKVLPKHS LLYEYFTVYN  600
ELTKVKYVTE GMRKPAFLSG EQKKAIVDLL FKTNRKVTVK QLKEDYFKKI ECFDSVEISG  660
VEDRFNASLG TYHDLLKIIK DKDFLDNEEN EDILEDIVLT LTLFEDREMI EERLKTYAHL  720
FDDKVMKQLK RRRYTGWGRL SRKLINGIRD KQSGKTILDF LKSDGFANRN FMQLIHDDSL  780
TFKEDIQKAQ VSGQGDSLHE HIANLAGSPA IKKGILQTVK VVDELVKVMG RHKPENIVIE  840
MARENQTTQK GQKNSRERMK RIEEGIKELG SQILKEHPVE NTQLQNEKLY LYYLQNGRDM  900
YVDQELDINR LSDYDVDAIV PQSFLKDDSI DNKVLTRSDK NRGKSDNVPS EEVVKKMKNY  960
WRQLLNAKLI TQRKFDNLTK AERGGLSELD KAGFIKRQLV ETRQITKHVA QILDSRMNTK  1020
YDENDKLIRE VKVITLKSKL VSDFRKDFQF YKVREINNYH HAHDAYLNAV VGTALIKKYP  1080
KLESEFVYGD YKVYDVRKMI AKSEQEIGKA TAKYFFYSNI MNFFKTEITL ANGEIRKRPL  1140
IETNGETGEI VWDKGRDFAT VRKVLSMPQV NIVKKTEVQT GGFSKESILP KRNSDKLIAR  1200
KKDWDPKKYG GFDSPTVAYS VLVVAKVEKG KSKKLKSVKE LLGITIMERS SFEKNPIDFL  1260
EAKGYKEVKK DLIIKLPKYS LFELENGRKR MLASAGELQK GNELALPSKY VNFLYLASHY  1320
EKLKGSPEDN EQKQLFVEQH KHYLDEIIEQ ISEFSKRVIL ADANLDKVLS AYNKHRDKPI  1380
REQAENIIHL FTLTNLGAPA AFKYFDTTID RKRYTSTKEV LDATLIHQSI TGLYETRIDL  1440
SQLGGDSRAD YPYDVPDYAS GSPKKKRKVS PGGGPSSGAP PPSGGSPAGS PTSTEEGTSE  1500
SATPESGPGT STEPSEGSAP GSPAGSPTST EEGTSTEPSE GSAPGTSTEP SENHDQEFDP  1560
PKVYPPVPAE KRKPIRVLSL FDGIATGLLV LKDLGIQVDR YIASEVCEDS ITVGMVRHQG  1620
KIMYVGDVRS VTQKHIQEWG PFDLVIGGSP CNDLSIVNPA RKGLYEGTGR LFFEFYRLLH  1680
DARPKEGDDR PFFWLFENVV AMGVSDKRDI SRFLESNPVM IDAKEVSAAH RARYFWGNLP  1740
GMNRPLASTV NDKLELQECL EHGRIAKFSK VRTITTRSNS IKQGKDQHFP VFMNEKEDIL  1800
WCTEMERVFG FPVHYTDVSN MSRLARQRLL GRSWSVPVIR HLFAPLKEYF ACVSSGNSNA  1860
NSRGPSFSSG LVPLSLRGSH MGPMEIYKTV SAWKRQPVRV LSLFRNIDKV LKSLGFLESG  1920
SGSGGGTLKY VEDVTNVVRR DVEKWGPFDL VYGSTQPLGS SCDRCPGWYM FQFHRILQYA  1980
LPRQESQRPF FWIFMDNLLL TEDDQETTTR FLQTEAVTLQ DVRGRDYQNA MRVWSNIPGL  2040
KSKHAPLTPK EEEYLQAQVR SRSKLDAPKV DLLVKNCLLP LREYFKYFSQ NSLPLSRADP  2100
KKKRKVGSGA TNFSLLKQAG DVEENPGPSE LIKENMHMKL YMEGTVDNHH FKCTSEGEGK  2160
PYEGTQTMRI KVVEGGPLPF AFDILATSFL YGSKTFINHT QGIPDFFKQS FPEGFTWERV  2220
TTYEDGGVLT ATQDTSLQDG CLIYNVKIRG VNFTSNGPVM QKKTLGWEAF TETLYPADGG  2280
LEGRNDMALK LVGGSHLIAN IKTTYRSKKP AKNLKMPGVY YVDYRLERIK EANNETYVEQ  2340
HEVAVARYCD LPSKLGHKLN                                            2360

SEQ ID NO: 6           moltype = AA  length = 2382
```

```
FEATURE                Location/Qualifiers
REGION                 1..2382
                       note = Synthetic polypeptide
source                 1..2382
                       mol_type = protein
                       organism = synthetic construct
SEQUENCE: 6
DAKSLTAWSR TLVTFKDVFV DFTREEWKLL DTAQQIVYRN VMLENYKNLV SLGYQLTKPD  60
VILRLEKGEE PGGSGGGSMD KKYSIGLAIG TNSVGWAVIT DEYKVPSKKF KVLGNTDRHS  120
IKKNLIGALL FDSGETAEAT RLKRTARRRY TRRKNRICYL QEIFSNEMAK VDDSFFHRLE  180
ESFLVEEDKK HERHPIFGNI VDEVAYHEKY PTIYHLRKKL VDSTDKADLR LIYLALAHMI  240
KFRGHFLIEG DLNPDNSDVD KLFIQLVQTY NQLFEENPIN ASGVDAKAIL SARLSKSRRL  300
ENLIAQLPGE KKNGLFGNLI ALSLGLTPNF KSNFDLAEDA KLQLSKDTYD DDLDNLLAQI  360
GDQYADLFLA AKNLSDAILL SDILRVNTEI TKAPLSASMI KRYDEHHQDL TLLKALVRQQ  420
LPEKYKEIFF DQSKNGYAGY IDGGASQEEF YKFIKPILEK MDGTEELLVK LNREDLLRKQ  480
RTFDNGSIPH QIHLGELHAI LRRQEDFYPF LKDNREKIEK ILTFRIPYYV GPLARGNSRF  540
AWMTRKSEET ITPWNFEEVV DKGASAQSFI ERMTNFDKNL PNEKVLPKHS LLYEYFTVYN  600
ELTKVKYVTE GMRKPAFLSG EQKKAIVDLL FKTNRKVTVK QLKEDYFKKI ECFDSVEISG  660
VEDRFNASLG TYHDLLKIIK DKDFLDNEEN EDILEDIVLT LTLFEDREMI EERLKTYAHL  720
FDDKVMKQLK RRRYTGWGRL SRKLINGIRD KQSGKTILDF LKSDGFANRN FMQLIHDDSL  780
TFKEDIQKAQ VSGQGDSLHE HIANLAGSPA IKKGILQTVK VVDELVKVMG RHKPENIVIE  840
MARENQTTQK GQKNSRERMK RIEEGIKELG SQILKEHPVE NTQLQNEKLY LYYLQNGRDM  900
YVDQELDINR LSDYDVDAIV PQSFLKDDSI DNKVLTRSDK NRGKSDNVPS EEVVKKMKNY  960
WRQLLNAKLI TQRKFDNLTK AERGGLSELD KAGFIKRQLV ETRQITKHVA QILDSRMNTK  1020
YDENDKLIRE VKVITLKSKL VSDFRKDFQF YKVREINNYH HAHDAYLNAV VGTALIKKYP  1080
KLESEFVYGD YKVYDVRKMI AKSEQEIGKA TAKYFFYSNI MNFFKTEITL ANGEIRKRPL  1140
IETNGETGEI VWDKGRDFAT VRKVLSMPQV NIVKKTEVQT GGFSKESILP KRNSDKLIAR  1200
KKDWDPKKYG GFDSPTVAYS VLVVAKVEKG KSKKLKSVKE LLGITIMERS SFEKNPIDFL  1260
EAKGYKEVKK DLIIKLPKYS LFELENGRKR MLASAGELQK GNELALPSKY VNFLYLASHY  1320
EKLKGSPEDN EQKQLFVEQH KHYLDEIIEQ ISEFSKRVIL ADANLDKVLS AYNKHRDKPI  1380
REQAENIIHL FTLTNLGAPA AFKYFDTTID RKRYTSTKEV LDATLIHQSI TGLYETRIDL  1440
SQLGGDSRAD YPYDVPDYAS GSPKKKRKVS PGGGPSSGAP PPSGGSPAGS PTSTEEGTSE  1500
SATPESGPGT STEPSEGSAP GSPAGSPTST EEGTSTEPSE GSAPGTSTEP SENHDQEFDP  1560
PKVYPPVPAE KRKPIRVLSL FDGIATGLLV LKDLGIQVDR YIASEVCEDS ITVGMVRHQG  1620
KIMYVGDVRS VTQKHIQEWG PFDLVIGGSP CNDLSIVNPA RKGLYEGTGR LFFEFYRLLH  1680
DARPKEGDDR PFFWLFENVV AMGVSDKRDI SRFLESNPVM IDAKEVSAAH RARYFWGNLP  1740
GMNRPLASTV NDKLELQECL EHGRIAKFSK VRTITTRSNS IKQGKDQHFP VFMNEKEDIL  1800
WCTEMERVFG FPVHYTDVSN MSRLARQRLL GRSWSVPVIR HLFAPLKEYF ACVSSGNSNA  1860
NSRGPSFSSG LVPLSLRGSH MGPMEIYKTV SAWKRQPVRV LSLFRNIDKV LKSLGFLESG  1920
SGSGGGTLKY VEDVTNVVRR DVEKWGPFDL VYGSTQPLGS SCDRCPGWYM FQFHRILQYA  1980
LPRQESQRPF FWIFMDNLLL TEDDQETTTR FLQTEAVTLQ DVRGRDYQNA MRVWSNIPGL  2040
KSKHAPLTPK EEEYLQAQVR SRSKLDAPKV DLLVKNCLLP LREYFKYFSQ NSLPLSRADP  2100
KKKRKVGSGA TNFSLLKQAG DVEENPGPGS GATNFSLLKQ AGDVEENPGP SELIKENMHM  2160
KLYMEGTVDN HHFKCTSEGE GKPYEGTQTM RIKVVEGGPL PFAFDILATS FLYGSKTFIN  2220
HTQGIPDFFK QSFPEGFTWE RVTTYEDGGV LTATQDTSLQ DGCLIYNVKI RGVNFTSNGP  2280
VMQKKTLGWE AFTETLYPAD GGLEGRNDMA LKLVGGSHLI ANIKTTYRSK KPAKNLKMPG  2340
VYYVDYRLER IKEANNETYV EQHEVAVARY CDLPSKLGHK LN                   2382

SEQ ID NO: 7           moltype = AA  length = 2303
FEATURE                Location/Qualifiers
REGION                 1..2303
                       note = Synthetic polypeptide
source                 1..2303
                       mol_type = protein
                       organism = synthetic construct
SEQUENCE: 7
DAKSLTAWSR TLVTFKDVFV DFTREEWKLL DTAQQIVYRN VMLENYKNLV SLGYQLTKPD  60
VILRLEKGEE PSGSETPGTS ESATPESMDK KYSIGLAIGT NSVGWAVITD EYKVPSKKFK  120
VLGNTDRHSI KKNLIGALLF DSGETAEATR LKRTARRRYT RRKNRICYLQ EIFSNEMAKV  180
DDSFFHRLEE SFLVEEDKKH ERHPIFGNIV DEVAYHEKYP TIYHLRKKLV DSTDKADLRL  240
IYLALAHMIK FRGHFLIEGD LNPDNSDVDK LFIQLVQTYN QLFEENPINA SGVDAKAILS  300
ARLSKSRRLE NLIAQLPGEK KNGLFGNLIA LSLGLTPNFK SNFDLAEDAK LQLSKDTYDD  360
DLDNLLAQIG DQYADLFLAA KNLSDAILLS DILRVNTEIT KAPLSASMIK RYDEHHQDLT  420
LLKALVRQQL PEKYKEIFFD QSKNGYAGYI DGGASQEEFY KFIKPILEKM DGTEELLVKL  480
NREDLLRKQR TFDNGSIPHQ IHLGELHAIL RRQEDFYPFL KDNREKIEKI LTFRIPYYVG  540
PLARGNSRFA WMTRKSEETI TPWNFEEVVD KGASAQSFIE RMTNFDKNLP NEKVLPKHSL  600
LYEYFTVYNE LTKVKYVTEG MRKPAFLSGE QKKAIVDLLF KTNRKVTVKQ LKEDYFKKIE  660
CFDSVEISGV EDRFNASLGT YHDLLKIIKD KDFLDNEENE DILEDIVLTL TLFEDREMIE  720
ERLKTYAHLF DDKVMKQLKR RRYTGWGRLS RKLINGIRDK QSGKTILDFL KSDGFANRNF  780
MQLIHDDSLT FKEDIQKAQV SGQGDSLHEH IANLAGSPAI KKGILQTVKV VDELVKVMGR  840
HKPENIVIEM ARENQTTQKG QKNSRERMKR IEEGIKELGS QILKEHPVEN TQLQNEKLYL  900
YYLQNGRDMY VDQELDINRL SDYDVDAIVP QSFLKDDSID NKVLTRSDKN RGKSDNVPSE  960
EVVKKMKNYW RQLLNAKLIT QRKFDNLTKA ERGGLSELDK AGFIKRQLVE TRQITKHVAQ  1020
ILDSRMNTKY DENDKLIREV KVITLKSKLV SDFRKDFQFY KVREINNYHH AHDAYLNAVV  1080
GTALIKKYPK LESEFVYGDY KVYDVRKMIA KSEQEIGKAT AKYFFYSNIM NFFKTEITLA  1140
NGEIRKRPLI ETNGETGEIV WDKGRDFATV RKVLSMPQVN IVKKTEVQTG GFSKESILPK  1200
RNSDKLIARK KDWDPKKYGG FDSPTVAYSV LVVAKVEKGK SKKLKSVKEL LGITIMERSS  1260
FEKNPIDFLE AKGYKEVKKD LIIKLPKYSL FELENGRKRM LASAGELQKG NELALPSKYV  1320
NFLYLASHYE KLKGSPEDNE QKQLFVEQHK HYLDEIIEQI SEFSKRVILA DANLDKVLSA  1380
```

-continued

```
YNKHRDKPIR EQAENIIHLF TLTNLGAPAA FKYFDTTIDR KRYTSTKEVL DATLIHQSIT  1440
GLYETRIDLS QLGGDSRADY PYDVPDYASG SPKKKRKVEA SGSGRASPGI PGSTRNHDQE  1500
FDPPKVYPPV PAEKRKPIRV LSLFDGIATG LLVLKDLGIQ VDRYIASEVC EDSITVGMVR  1560
HQGKIMYVGD VRSVTQKHIQ EWGPFDLVIG GSPCNDLSIV NPARKGLYEG TGRLFFEFYR  1620
LLHDARPKEG DDRPFFWLFE NVVAMGVSDK RDISRFLESN PVMIDAKEVS AAHRARYFWG  1680
NLPGMNRPLA STVNDKLELQ ECLEHGRIAK FSKVRTITTR SNSIKQGKDQ HFPVFMNEKE  1740
DILWCTEMER VFGFPVHYTD VSNMSRLARQ RLLGRSWSVP VIRHLFAPLK EYFACVSSGN  1800
SNANSRGPSF SSGLVPLSLR GSHMGPMEIY KTVSAWKRQP VRVLSLFRNI DKVLKSLGFL  1860
ESGSGSGGGT LKYVEDVTNV VRRDVEKWGP FDLVYGSTQP LGSSCDRCPG WYMFQFHRIL  1920
QYALPRQESQ RPFFWIFMDN LLLTEDDQET TTRFLQTEAV TLQDVRGRDY QNAMRVWSNI  1980
PGLKSKHAPL TPKEEEYLQA QVRSRSKLDA PKVDLLVKNC LLPLREYFKY FSQNSLPLSR  2040
ADPKKKRKVG SGATNFSLLK QAGDVEENPG PSELIKENMH MKLYMEGTVD NHHFKCTSEG  2100
EGKPYEGTQT MRIKVVEGGP LPFAFDILAT SFLYGSKTFI NHTQGIPDFF KQSFPEGFTW  2160
ERVTTYEDGG VLTATQDTSL QDGCLIYNVK IRGVNFTSNG PVMQKKTLGW EAFTETLYPA  2220
DGGLEGRNDM ALKLVGGSHL IANIKTTYRS KKPAKNLKMP GVYYVDYRLE RIKEANNETY  2280
VEQHEVAVAR YCDLPSKLGH KLN                                         2303

SEQ ID NO: 8            moltype = AA  length = 2325
FEATURE                 Location/Qualifiers
REGION                  1..2325
                        note = Synthetic polypeptide
source                  1..2325
                        mol_type = protein
                        organism = synthetic construct
SEQUENCE: 8
DAKSLTAWSR TLVTFKDVFV DFTREEWKLL DTAQQIVYRN VMLENYKNLV SLGYQLTKPD  60
VILRLEKGEE PSGSETPGTS ESATPESMDK KYSIGLAIGT NSVGWAVITD EYKVPSKKFK  120
VLGNTDRHSI KKNLIGALLF DSGETAEATR LKRTARRRYT RRKNRICYLQ EIFSNEMAKV  180
DDSFFHRLEE SFLVEEDKKH ERHPIFGNIV DEVAYHEKYP TIYHLRKKLV DSTDKADLRL  240
IYLALAHMIK FRGHFLIEGD LNPDNSDVDK LFIQLVQTYN QLFEENPINA SGVDAKAILS  300
ARLSKSRRLE NLIAQLPGEK KNGLFGNLIA LSLGLTPNFK SNFDLAEDAK LQLSKDTYDD  360
DLDNLLAQIG DQYADLFLAA KNLSDAILLS DILRVNTEIT KAPLSASMIK RYDEHHQDLT  420
LLKALVRQQL PEKYKEIFFD QSKNGYAGYI DGGASQEEFY KFIKPILEKM DGTEELLVKL  480
NREDLLRKQR TFDNGSIPHQ IHLGELHAIL RRQEDFYPFL KDNREKIEKI LTFRIPYYVG  540
PLARGNSRFA WMTRKSEETI TPWNFEEVVD KGASAQSFIE RMTNFDKNLP NEKVLPKHSL  600
LYEYFTVYNE LTKVKYVTEG MRKPAFLSGE QKKAIVDLLF KTNRKVTVKQ LKEDYFKKIE  660
CFDSVEISGV EDRFNASLGT YHDLLKIIKD KDFLDNEENE DILEDIVLTL TLFEDREMIE  720
ERLKTYAHLF DDKVMKQLKR RRYTGWGRLS RKLINGIRDK QSGKTILDFL KSDGFANRNF  780
MQLIHDDSLT FKEDIQKAQV SGQGDSLHEH IANLAGSPAI KKGILQTVKV VDELVKVMGR  840
HKPENIVIEM ARENQTTQKG QKNSRERMKR IEEGIKELGS QILKEHPVEN TQLQNEKLYL  900
YYLQNGRDMY VDQELDINRL SDYDVDAIVP QSFLKDDSID NKVLTRSDKN RGKSDNVPSE  960
EVVKKMKNYW RQLLNAKLIT QRKFDNLTKA ERGGLSELDK AGFIKRQLVE TRQITKHVAQ  1020
ILDSRMNTKY DENDKLIREV KVITLKSKLV SDFRKDFQFY KVREINNYHH AHDAYLNAVV  1080
GTALIKKYPK LESEFVYGDY KVYDVRKMIA KSEQEIGKAT AKYFFYSNIM NFFKTEITLA  1140
NGEIRKRPLI ETNGETGEIV WDKGRDFATV RKVLSMPQVN IVKKTEVQTG GFSKESILPK  1200
RNSDKLIARK KDWDPKKYGG FDSPTVAYSV LVVAKVEKGK SKKLKSVKEL LGITIMERSS  1260
FEKNPIDFLE AKGYKEVKKD LIIKLPKYSL FELENGRKRM LASAGELQKG NELALPSKYV  1320
NFLYLASHYE KLKGSPEDNE QKQLFVEQHK HYLDEIIEQI SEFSKRVILA DANLDKVLSA  1380
YNKHRDKPIR EQAENIIHLF TLTNLGAPAA FKYFDTTIDR KRYTSTKEVL DATLIHQSIT  1440
GLYETRIDLS QLGGDSRADY PYDVPDYASG SPKKKRKVEA SGSGRASPGI PGSTRNHDQE  1500
FDPPKVYPPV PAEKRKPIRV LSLFDGIATG LLVLKDLGIQ VDRYIASEVC EDSITVGMVR  1560
HQGKIMYVGD VRSVTQKHIQ EWGPFDLVIG GSPCNDLSIV NPARKGLYEG TGRLFFEFYR  1620
LLHDARPKEG DDRPFFWLFE NVVAMGVSDK RDISRFLESN PVMIDAKEVS AAHRARYFWG  1680
NLPGMNRPLA STVNDKLELQ ECLEHGRIAK FSKVRTITTR SNSIKQGKDQ HFPVFMNEKE  1740
DILWCTEMER VFGFPVHYTD VSNMSRLARQ RLLGRSWSVP VIRHLFAPLK EYFACVSSGN  1800
SNANSRGPSF SSGLVPLSLR GSHMGPMEIY KTVSAWKRQP VRVLSLFRNI DKVLKSLGFL  1860
ESGSGSGGGT LKYVEDVTNV VRRDVEKWGP FDLVYGSTQP LGSSCDRCPG WYMFQFHRIL  1920
QYALPRQESQ RPFFWIFMDN LLLTEDDQET TTRFLQTEAV TLQDVRGRDY QNAMRVWSNI  1980
PGLKSKHAPL TPKEEEYLQA QVRSRSKLDA PKVDLLVKNC LLPLREYFKY FSQNSLPLSR  2040
ADPKKKRKVG SGATNFSLLK QAGDVEENPG PGSGATNFSL LKQAGDVEEN PGPSELIKEN  2100
MHMKLYMEGT VDNHHFKCTS EGEGKPYEGT QTMRIKVVEG GPLPFAFDIL ATSFLYGSKT  2160
FINHTQGIPD FFKQSFPEGF TWERVTTYED GGVLTATQDT SLQDGCLIYN VKIRGVNFTS  2220
NGPVMQKKTL GWEAFTETLY PADGGLEGRN DMALKLVGGS HLIANIKTTY RSKKPAKNLK  2280
MPGVYYVDYR LERIKEANNE TYVEQHEVAV ARYCDLPSKL GHKLN                 2325

SEQ ID NO: 9            moltype = AA  length = 2367
FEATURE                 Location/Qualifiers
REGION                  1..2367
                        note = Synthetic polypeptide
source                  1..2367
                        mol_type = protein
                        organism = synthetic construct
SEQUENCE: 9
DAKSLTAWSR TLVTFKDVFV DFTREEWKLL DTAQQIVYRN VMLENYKNLV SLGYQLTKPD  60
VILRLEKGEE PGGPSSGAPP PSGGSPAGSP TSTEEGTSES ATPESGPGTS TEPSEGSAPG  120
SPAGSPTSTE EGTSTEPSEG SAPGTSTEPS EMDKKYSIGL AIGTNSVGWA VITDEYKVPS  180
KKFKVLGNTD RHSIKKNLIG ALLFDSGETA EATRLKRTAR RRYTRRKNRI CYLQEIFSNE  240
MAKVDDSFFH RLEESFLVEE DKKHERHPIF GNIVDEVAYH EKYPTIYHLR KKLVDSTDKA  300
DLRLIYLALA HMIKFRGHFL IEGDLNPDNS DVDKLFIQLV QTYNQLFEEN PINASGVDAK  360
```

-continued

```
AILSARLSKS RRLENLIAQL PGEKKNGLFG NLIALSLGLT PNFKSNFDLA EDAKLQLSKD  420
TYDDDLDNLL AQIGDQYADL FLAAKNLSDA ILLSDILRVN TEITKAPLSA SMIKRYDEHH  480
QDLTLLKALV RQQLPEKYKE IFFDQSKNGY AGYIDGGASQ EEFYKFIKPI LEKMDGTEEL  540
LVKLNREDLL RKQRTFDNGS IPHQIHLGEL HAILRRQEDF YPFLKDNREK IEKILTFRIP  600
YYVGPLARGN SRFAWMTRKS EETITPWNFE EVVDKGASAQ SFIERMTNFD KNLPNEKVLP  660
KHSLLYEYFT VYNELTKVKY VTEGMRKPAF LSGEQKKAIV DLLFKTNRKV TVKQLKEDYF  720
KKIECFDSVE ISGVEDRFNA SLGTYHDLLK IIKDKDFLDN EENEDILEDI VLTLTLFEDR  780
EMIEERLKTY AHLFDDKVMK QLKRRRYTGW GRLSRKLING IRDKQSGKTI LDFLKSDGFA  840
NRNFMQLIHD DSLTFKEDIQ KAQVSGQGDS LHEHIANLAG SPAIKKGILQ TVKVVDELVK  900
VMGRHKPENI VIEMARENQT TQKGQKNSRE RMKRIEEGIK ELGSQILKEH PVENTQLQNE  960
KLYLYYLQNG RDMYVDQELD INRLSDYDVD AIVPQSFLKD DSIDNKVLTR SDKNRGKSDN  1020
VPSEEVVKKM KNYWRQLLNA KLITQRKFDN LTKAERGGLS ELDKAGFIKR QLVETRQITK  1080
HVAQILDSRM NTKYDENDKL IREVKVITLK SKLVSDFRKD FQFYKVREIN NYHHAHDAYL  1140
NAVVGTALIK KYPKLESEFV YGDYKVYDVR KMIAKSEQEI GKATAKYFFY SNIMNFFKTE  1200
ITLANGEIRK RPLIETNGET GEIVWDKGRD FATVRKVLSM PQVNIVKKTE VQTGGFSKES  1260
ILPKRNSDKL IARKKDWDPK KYGGFDSPTV AYSVLVVAKV EKGKSKKLKS VKELLGITIM  1320
ERSSFEKNPI DFLEAKGYKE VKKDLIIKLP KYSLFELENG RKRMLASAGE LQKGNELALP  1380
SKYVNFLYLA SHYEKLKGSP EDNEQKQLFV EQHKHYLDEI IEQISEFSKR VILADANLDK  1440
VLSAYNKHRD KPIREQAENI IHLFTLTNLG APAAFKYFDT TIDRKRYTST KEVLDATLIH  1500
QSITGLYETR IDLSQLGGDS RADYPYDVPD YASGSPKKKR KVEASGSGRA SPGIPGSTRN  1560
HDQEFDPPKV YPPVPAEKRK PIRVLSLFDG IATGLLVLKD LGIQVDRYIA SEVCEDSITV  1620
GMVRHQGKIM YVGDVRSVTQ KHIQEWGPFD LVIGGSPCND LSIVNPARKG LYEGTGRLFF  1680
EFYRLLHDAR PKEGDDRPFF WLFENVVAMG VSDKRDISRF LESNPVMIDA KEVSAAHRAR  1740
YFWGNLPGMN RPLASTVNDK LELQECLEHG RIAKFSKVRT ITTRSNSIKQ GKDQHFPVFM  1800
NEKEDILWCT EMERVFGFPV HYTDVSNMSR LARQRLLGRS WSVPVIRHLF APLKEYFACV  1860
SSGNSNANSR GPSFSSGLVP LSLRGSHMGP MEIYKTVSAW KRQPVRVLSL FRNIDKVLKS  1920
LGFLESGSGS GGGTLKYVED VTNVVRRDVE KWGPFDLVYG STQPLGSSCD RCPGWYMFQF  1980
HRILQYALPR QESQRPFFWI FMDNLLLTED DQETTTRFLQ TEAVTLQDVR GRDYQNAMRV  2040
WSNIPGLKSK HAPLTPKEEE YLQAQVRSRS KLDAPKVDLL VKNCLLPLRE YFKYFSQNSL  2100
PLSRADPKKK RKVGSGATNF SLLKQAGDVE ENPGPSELIK ENMHMKLYME GTVDNHHFKC  2160
TSEGEGKPYE GTQTMRIKVV EGGPLPFAFD ILATSFLYGS KTFINHTQGI PDFFKQSFPE  2220
GFTWERVTTY EDGGVLTATQ DTSLQDGCLI YNVKIRGVNF TSNGPVMQKK TLGWEAFTET  2280
LYPADGGLEG RNDMALKLVG GSHLIANIKT TYRSKKPAKN LKMPGVYYVD YRLERIKEAN  2340
NETYVEQHEV AVARYCDLPS KLGHKLN                                     2367

SEQ ID NO: 10           moltype = AA  length = 2389
FEATURE                 Location/Qualifiers
REGION                  1..2389
                        note = Synthetic polypeptide
source                  1..2389
                        mol_type = protein
                        organism = synthetic construct
SEQUENCE: 10
DAKSLTAWSR TLVTFKDVFV DFTREEWKLL DTAQQIVYRN VMLENYKNLV SLGYQLTKPD  60
VILRLEKGEE PGGPSSGAPP PSGGSPAGSP TSTEEGTSES ATPESGPGTS TEPSEGSAPG  120
SPAGSPTSTE EGTSTEPSEG SAPGTSTEPS EMDKKYSIGL AIGTNSVGWA VITDEYKVPS  180
KKFKVLGNTD RHSIKKNLIG ALLFDSGETA EATRLKRTAR RRYTRRKNRI CYLQEIFSNE  240
MAKVDDSFFH RLEESFLVEE DKKHERHPIF GNIVDEVAYH EKYPTIYHLR KKLVDSTDKA  300
DLRLIYLALA HMIKFRGHFL IEGDLNPDNS DVDKLFIQLV QTYNQLFEEN PINASGVDAK  360
AILSARLSKS RRLENLIAQL PGEKKNGLFG NLIALSLGLT PNFKSNFDLA EDAKLQLSKD  420
TYDDDLDNLL AQIGDQYADL FLAAKNLSDA ILLSDILRVN TEITKAPLSA SMIKRYDEHH  480
QDLTLLKALV RQQLPEKYKE IFFDQSKNGY AGYIDGGASQ EEFYKFIKPI LEKMDGTEEL  540
LVKLNREDLL RKQRTFDNGS IPHQIHLGEL HAILRRQEDF YPFLKDNREK IEKILTFRIP  600
YYVGPLARGN SRFAWMTRKS EETITPWNFE EVVDKGASAQ SFIERMTNFD KNLPNEKVLP  660
KHSLLYEYFT VYNELTKVKY VTEGMRKPAF LSGEQKKAIV DLLFKTNRKV TVKQLKEDYF  720
KKIECFDSVE ISGVEDRFNA SLGTYHDLLK IIKDKDFLDN EENEDILEDI VLTLTLFEDR  780
EMIEERLKTY AHLFDDKVMK QLKRRRYTGW GRLSRKLING IRDKQSGKTI LDFLKSDGFA  840
NRNFMQLIHD DSLTFKEDIQ KAQVSGQGDS LHEHIANLAG SPAIKKGILQ TVKVVDELVK  900
VMGRHKPENI VIEMARENQT TQKGQKNSRE RMKRIEEGIK ELGSQILKEH PVENTQLQNE  960
KLYLYYLQNG RDMYVDQELD INRLSDYDVD AIVPQSFLKD DSIDNKVLTR SDKNRGKSDN  1020
VPSEEVVKKM KNYWRQLLNA KLITQRKFDN LTKAERGGLS ELDKAGFIKR QLVETRQITK  1080
HVAQILDSRM NTKYDENDKL IREVKVITLK SKLVSDFRKD FQFYKVREIN NYHHAHDAYL  1140
NAVVGTALIK KYPKLESEFV YGDYKVYDVR KMIAKSEQEI GKATAKYFFY SNIMNFFKTE  1200
ITLANGEIRK RPLIETNGET GEIVWDKGRD FATVRKVLSM PQVNIVKKTE VQTGGFSKES  1260
ILPKRNSDKL IARKKDWDPK KYGGFDSPTV AYSVLVVAKV EKGKSKKLKS VKELLGITIM  1320
ERSSFEKNPI DFLEAKGYKE VKKDLIIKLP KYSLFELENG RKRMLASAGE LQKGNELALP  1380
SKYVNFLYLA SHYEKLKGSP EDNEQKQLFV EQHKHYLDEI IEQISEFSKR VILADANLDK  1440
VLSAYNKHRD KPIREQAENI IHLFTLTNLG APAAFKYFDT TIDRKRYTST KEVLDATLIH  1500
QSITGLYETR IDLSQLGGDS RADYPYDVPD YASGSPKKKR KVEASGSGRA SPGIPGSTRN  1560
HDQEFDPPKV YPPVPAEKRK PIRVLSLFDG IATGLLVLKD LGIQVDRYIA SEVCEDSITV  1620
GMVRHQGKIM YVGDVRSVTQ KHIQEWGPFD LVIGGSPCND LSIVNPARKG LYEGTGRLFF  1680
EFYRLLHDAR PKEGDDRPFF WLFENVVAMG VSDKRDISRF LESNPVMIDA KEVSAAHRAR  1740
YFWGNLPGMN RPLASTVNDK LELQECLEHG RIAKFSKVRT ITTRSNSIKQ GKDQHFPVFM  1800
NEKEDILWCT EMERVFGFPV HYTDVSNMSR LARQRLLGRS WSVPVIRHLF APLKEYFACV  1860
SSGNSNANSR GPSFSSGLVP LSLRGSHMGP MEIYKTVSAW KRQPVRVLSL FRNIDKVLKS  1920
LGFLESGSGS GGGTLKYVED VTNVVRRDVE KWGPFDLVYG STQPLGSSCD RCPGWYMFQF  1980
HRILQYALPR QESQRPFFWI FMDNLLLTED DQETTTRFLQ TEAVTLQDVR GRDYQNAMRV  2040
WSNIPGLKSK HAPLTPKEEE YLQAQVRSRS KLDAPKVDLL VKNCLLPLRE YFKYFSQNSL  2100
PLSRADPKKK RKVGSGATNF SLLKQAGDVE ENPGPGSGAT NFSLLKQAGD VEENPGPSEL  2160
```

```
IKENMHMKLY MEGTVDNHHF KCTSEGEGKP YEGTQTMRIK VVEGGPLPFA FDILATSFLY  2220
GSKTFINHTQ GIPDFFKQSF PEGFTWERVT TYEDGGVLTA TQDTSLQDGC LIYNVKIRGV  2280
NFTSNGPVMQ KKTLGWEAFT ETLYPADGGL EGRNDMALKL VGGSHLIANI KTTYRSKKPA  2340
KNLKMPGVYY VDYRLERIKE ANNETYVEQH EVAVARYCDL PSKLGHKLN              2389

SEQ ID NO: 11           moltype = AA  length = 2369
FEATURE                 Location/Qualifiers
REGION                  1..2369
                        note = Synthetic polypeptide
source                  1..2369
                        mol_type = protein
                        organism = synthetic construct
SEQUENCE: 11
DAKSLTAWSR TLVTFKDVFV DFTREEWKLL DTAQQIVYRN VMLENYKNLV SLGYQLTKPD  60
VILRLEKGEE PSGSETPGTS ESATPESMDK KYSIGLAIGT NSVGWAVITD EYKVPSKKFK  120
VLGNTDRHSI KKNLIGALLF DSGETAEATR LKRTARRRYT RRKNRICYLQ EIFSNEMAKV  180
DDSFFHRLEE SFLVEEDKKH ERHPIFGNIV DEVAYHEKYP TIYHLRKKLV DSTDKADLRL  240
IYLALAHMIK FRGHFLIEGD LNPDNSDVDK LFIQLVQTYN QLFEENPINA SGVDAKAILS  300
ARLSKSRRLE NLIAQLPGEK KNGLFGNLIA LSLGLTPNFK SNFDLAEDAK LQLSKDTYDD  360
DLDNLLAQIG DQYADLFLAA KNLSDAILLS DILRVNTEIT KAPLSASMIK RYDEHHQDLT  420
LLKALVRQQL PEKYKEIFFD QSKNGYAGYI DGGASQEEFY KFIKPILEKM DGTEELLVKL  480
NREDLLRKQR TFDNGSIPHQ IHLGELHAIL RRQEDFYPFL KDNREKIEKI LTFRIPYYVG  540
PLARGNSRFA WMTRKSEETI TPWNFEEVVD KGASAQSFIE RMTNFDKNLP NEKVLPKHSL  600
LYEYFTVYNE LTKVKYVTEG MRKPAFLSGE QKKAIVDLLF KTNRKVTVKQ LKEDYFKKIE  660
CFDSVEISGV EDRFNASLGT YHDLLKIIKD KDFLDNEENE DILEDIVLTL TLFEDREMIE  720
ERLKTYAHLF DDKVMKQLKR RRYTGWGRLS RKLINGIRDK QSGKTILDFL KSDGFANRNF  780
MQLIHDDSLT FKEDIQKAQV SGQGDSLHEH IANLAGSPAI KKGILQTVKV VDELVKVMGR  840
HKPENIVIEM ARENQTTQKG QKNSRERMKR IEEGIKELGS QILKEHPVEN TQLQNEKLYL  900
YYLQNGRDMY VDQELDINRL SDYDVDAIVP QSFLKDDSID NKVLTRSDKN RGKSDNVPSE  960
EVVKKMKNYW RQLLNAKLIT QRKFDNLTKA ERGGLSELDK AGFIKRQLVE TRQITKHVAQ  1020
ILDSRMNTKY DENDKLIREV KVITLKSKLV SDFRKDFQFY KVREINNYHH AHDAYLNAVV  1080
GTALIKKYPK LESEFVYGDY KVYDVRKMIA KSEQEIGKAT AKYFFYSNIM NFFKTEITLA  1140
NGEIRKRPLI ETNGETGEIV WDKGRDFATV RKVLSMPQVN IVKKTEVQTG GFSKESILPK  1200
RNSDKLIARK KDWDPKKYGG FDSPTVAYSV LVVAKVEKGK SKKLKSVKEL LGITIMERSS  1260
FEKNPIDFLE AKGYKEVKKD LIIKLPKYSL FELENGRKRM LASAGELQKG NELALPSKYV  1320
NFLYLASHYE KLKGSPEDNE QKQLFVEQHK HYLDEIIEQI SEFSKRVILA DANLDKVLSA  1380
YNKHRDKPIR EQAENIIHLF TLTNLGAPAA FKYFDTTIDR KRYTSTKEVL DATLIHQSIT  1440
GLYETRIDLS QLGGDSRADY PYDVPDYASG SPKKKRKVSP GGGPSSGAPP PSGGSPAGSP  1500
TSTEEGTSES ATPESGPGTS TEPSEGSAPG SPAGSPTSTE EGTSTEPSEG SAPGTSTEPS  1560
ENHDQEFDPP KVYPPVPAEK RKPIRVLSLF DGIATGLLVL KDLGIQVDRY IASEVCEDSI  1620
TVGMVRHQGK IMYVGDVRSV TQKHIQEWGP FDLVIGGSPC NDLSIVNPAR KGLYEGTGRL  1680
FFEFYRLLHD ARPKEGDDRP FFWLFENVVA MGVSDKRDIS RFLESNPVMI DAKEVSAAHR  1740
ARYFWGNLPG MNRPLASTVN DKLELQECLE HGRIAKFSKV RTITTRSNSI KQGKDQHFPV  1800
FMNEKEDILW CTEMERVFGF PVHYTDVSNM SRLARQRLLG RSWSVPVIRH LFAPLKEYFA  1860
CVSSGNSNAN SRGPSFSSGL VPLSLRGSHM GPMEIYKTVS AWKRQPVRVL SLFRNIDKVL  1920
KSLGFLESGS GSGGGTLKYV EDVTNVVRRD VEKWGPFDLV YGSTQPLGSS CDRCPGWYMF  1980
QFHRILQYAL PRQESQRPFF WIFMDNLLLT EDDQETTTRF LQTEAVTLQD VRGRDYQNAM  2040
RVWSNIPGLK SKHAPLTPKE EEYLQAQVRS RSKLDAPKVD LLVKNCLLPL REYFKYFSQN  2100
SLPLSRADPK KKRKVGSGAT NFSLLKQAGD VEENPGPSEL IKENMHMKLY MEGTVDNHHF  2160
KCTSEGEGKP YEGTQTMRIK VVEGGPLPFA FDILATSFLY GSKTFINHTQ GIPDFFKQSF  2220
PEGFTWERVT TYEDGGVLTA TQDTSLQDGC LIYNVKIRGV NFTSNGPVMQ KKTLGWEAFT  2280
ETLYPADGGL EGRNDMALKL VGGSHLIANI KTTYRSKKPA KNLKMPGVYY VDYRLERIKE  2340
ANNETYVEQH EVAVARYCDL PSKLGHKLN                                    2369

SEQ ID NO: 12           moltype = AA  length = 2391
FEATURE                 Location/Qualifiers
REGION                  1..2391
                        note = Synthetic polypeptide
source                  1..2391
                        mol_type = protein
                        organism = synthetic construct
SEQUENCE: 12
DAKSLTAWSR TLVTFKDVFV DFTREEWKLL DTAQQIVYRN VMLENYKNLV SLGYQLTKPD  60
VILRLEKGEE PSGSETPGTS ESATPESMDK KYSIGLAIGT NSVGWAVITD EYKVPSKKFK  120
VLGNTDRHSI KKNLIGALLF DSGETAEATR LKRTARRRYT RRKNRICYLQ EIFSNEMAKV  180
DDSFFHRLEE SFLVEEDKKH ERHPIFGNIV DEVAYHEKYP TIYHLRKKLV DSTDKADLRL  240
IYLALAHMIK FRGHFLIEGD LNPDNSDVDK LFIQLVQTYN QLFEENPINA SGVDAKAILS  300
ARLSKSRRLE NLIAQLPGEK KNGLFGNLIA LSLGLTPNFK SNFDLAEDAK LQLSKDTYDD  360
DLDNLLAQIG DQYADLFLAA KNLSDAILLS DILRVNTEIT KAPLSASMIK RYDEHHQDLT  420
LLKALVRQQL PEKYKEIFFD QSKNGYAGYI DGGASQEEFY KFIKPILEKM DGTEELLVKL  480
NREDLLRKQR TFDNGSIPHQ IHLGELHAIL RRQEDFYPFL KDNREKIEKI LTFRIPYYVG  540
PLARGNSRFA WMTRKSEETI TPWNFEEVVD KGASAQSFIE RMTNFDKNLP NEKVLPKHSL  600
LYEYFTVYNE LTKVKYVTEG MRKPAFLSGE QKKAIVDLLF KTNRKVTVKQ LKEDYFKKIE  660
CFDSVEISGV EDRFNASLGT YHDLLKIIKD KDFLDNEENE DILEDIVLTL TLFEDREMIE  720
ERLKTYAHLF DDKVMKQLKR RRYTGWGRLS RKLINGIRDK QSGKTILDFL KSDGFANRNF  780
MQLIHDDSLT FKEDIQKAQV SGQGDSLHEH IANLAGSPAI KKGILQTVKV VDELVKVMGR  840
HKPENIVIEM ARENQTTQKG QKNSRERMKR IEEGIKELGS QILKEHPVEN TQLQNEKLYL  900
YYLQNGRDMY VDQELDINRL SDYDVDAIVP QSFLKDDSID NKVLTRSDKN RGKSDNVPSE  960
EVVKKMKNYW RQLLNAKLIT QRKFDNLTKA ERGGLSELDK AGFIKRQLVE TRQITKHVAQ  1020
```

```
ILDSRMNTKY DENDKLIREV KVITLKSKLV SDFRKDFQFY KVREINNYHH AHDAYLNAVV  1080
GTALIKKYPK LESEFVYGDY KVYDVRKMIA KSEQEIGKAT AKYFFYSNIM NFFKTEITLA  1140
NGEIRKRPLI ETNGETGEIV WDKGRDFATV RKVLSMPQVN IVKKTEVQTG GFSKESILPK  1200
RNSDKLIARK KDWDPKKYGG FDSPTVAYSV LVVAKVEKGK SKKLKSVKEL LGITIMERSS  1260
FEKNPIDFLE AKGYKEVKKD LIIKLPKYSL FELENGRKRM LASAGELQKG NELALPSKYV  1320
NFLYLASHYE KLKGSPEDNE QKQLFVEQHK HYLDEIIEQI SEFSKRVILA DANLDKVLSA  1380
YNKHRDKPIR EQAENIIHLF TLTNLGAPAA FKYFDTTIDR KRYTSTKEVL DATLIHQSIT  1440
GLYETRIDLS QLGGDSRADY PYDVPDYASG SPKKKRKVSP GGGPSSGAPP PSGGSPAGSP  1500
TSTEEGTSES ATPESGPGTS TEPSEGSAPG SPAGSPTSTE EGTSTEPSEG SAPGTSTEPS  1560
ENHDQEFDPP KVYPPVPAEK RKPIRVLSLF DGIATGLLVL KDLGIQVDRY IASEVCEDSI  1620
TVGMVRHQGK IMYVGDVRSV TQKHIQEWGP FDLVIGGSPC NDLSIVNPAR KGLYEGTGRL  1680
FFEFYRLLHD ARPKEGDDRP FFWLFENVVA MGVSDKRDIS RFLESNPVMI DAKEVSAAHR  1740
ARYFWGNLPG MNRPLASTVN DKLELQECLE HGRIAKFSKV RTITTRSNSI KQGKDQHFPV  1800
FMNEKEDILW CTEMERVFGF PVHYTDVSNM SRLARQRLLG RSWSVPVIRH LFAPLKEYFA  1860
CVSSGNSNAN SRGPSFSSGL VPLSLRGSHM GPMEIYKTVS AWKRQPVRVL SLFRNIDKVL  1920
KSLGFLESGS GSGGGTLKYV EDVTNVVRRD VEKWGPFDLV YGSTQPLGSS CDRCPGWYMF  1980
QFHRILQYAL PRQESQRPFF WIFMDNLLLT EDDQETTTRF LQTEAVTLQD VRGRDYQNAM  2040
RVWSNIPGLK SKHAPLTPKE EEYLQAQVRS RSKLDAPKVD LLVKNCLLPL REYFKYFSQN  2100
SLPLSRADPK KKRKVGSGAT NFSLLKQAGD VEENPGPGSG ATNFSLLKQA GDVEENPGPS  2160
ELIKENMHMK LYMEGTVDNH HFKCTSEGEG KPYEGTQTMR IKVVEGGPLP FAFDILATSF  2220
LYGSKTFINH TQGIPDFFKQ SFPEGFTWER VTTYEDGGVL TATQDTSLQD GCLIYNVKIR  2280
GVNFTSNGPV MQKKTLGWEA FTETLYPADG GLEGRNDMAL KLVGGSHLIA NIKTTYRSKK  2340
PAKNLKMPGV YYVDYRLERI KEANNETYVE QHEVAVARYC DLPSKLGHKL N           2391

SEQ ID NO: 13           moltype = AA  length = 2369
FEATURE                 Location/Qualifiers
REGION                  1..2369
                        note = Synthetic polypeptide
source                  1..2369
                        mol_type = protein
                        organism = synthetic construct
SEQUENCE: 13
DAKSLTAWSR TLVTFKDVFV DFTREEWKLL DTAQQIVYRN VMLENYKNLV SLGYQLTKPD  60
VILRLEKGEE PGGPSSGAPP PSGGSPAGSP TSTEEGTSES ATPESGPGTS TEPSEGSAPG  120
SPAGSPTSTE EGTSTEPSEG SAPGTSTEPS EMDKKYSIGL AIGTNSVGWA VITDEYKVPS  180
KKFKVLGNTD RHSIKKNLIG ALLFDSGETA EATRLKRTAR RRYTRRKNRI CYLQEIFSNE  240
MAKVDDSFFH RLEESFLVEE DKKHERHPIF GNIVDEVAYH EKYPTIYHLR KKLVDSTDKA  300
DLRLIYLALA HMIKFRGHFL IEGDLNPDNS DVDKLFIQLV QTYNQLFEEN PINASGVDAK  360
AILSARLSKS RRLENLIAQL PGEKKNGLFG NLIALSLGLT PNFKSNFDLA EDAKLQLSKD  420
TYDDDLDNLL AQIGDQYADL FLAAKNLSDA ILLSDILRVN TEITKAPLSA SMIKRYDEHH  480
QDLTLLKALV RQQLPEKYKE IFFDQSKNGY AGYIDGGASQ EEFYKFIKPI LEKMDGTEEL  540
LVKLNREDLL RKQRTFDNGS IPHQIHLGEL HAILRRQEDF YPFLKDNREK IEKILTFRIP  600
YYVGPLARGN SRFAWMTRKS EETITPWNFE EVVDKGASAQ SFIERMTNFD KNLPNEKVLP  660
KHSLLYEYFT VYNELTKVKY VTEGMRKPAF LSGEQKKAIV DLLFKTNRKV TVKQLKEDYF  720
KKIECFDSVE ISGVEDRFNA SLGTYHDLLK IIKDKDFLDN EENEDILEDI VLTLTLFEDR  780
EMIEERLKTY AHLFDDKVMK QLKRRRYTGW GRLSRKLING IRDKQSGKTI LDFLKSDGFA  840
NRNFMQLIHD DSLTFKEDIQ KAQVSGQGDS LHEHIANLAG SPAIKKGILQ TVKVVDELVK  900
VMGRHKPENI VIEMARENQT TQKGQKNSRE RMKRIEEGIK ELGSQILKEH PVENTQLQNE  960
KLYLYYLQNG RDMYVDQELD INRLSDYDVD AIVPQSFLKD DSIDNKVLTR SDKNRGKSDN  1020
VPSEEVVKKM KNYWRQLLNA KLITQRKFDN LTKAERGGLS ELDKAGFIKR QLVETRQITK  1080
HVAQILDSRM NTKYDENDKL IREVKVITLK SKLVSDFRKD FQFYKVREIN NYHHAHDAYL  1140
NAVVGTALIK KYPKLESEFV YGDYKVYDVR KMIAKSEQEI GKATAKYFFY SNIMNFFKTE  1200
ITLANGEIRK RPLIETNGET GEIVWDKGRD FATVRKVLSM PQVNIVKKTE VQTGGFSKES  1260
ILPKRNSDKL IARKKDWDPK KYGGFDSPTV AYSVLVVAKV EKGKSKKLKS VKELLGITIM  1320
ERSSFEKNPI DFLEAKGYKE VKKDLIIKLP KYSLFELENG RKRMLASAGE LQKGNELALP  1380
SKYVNFLYLA SHYEKLKGSP EDNEQKQLFV EQHKHYLDEI IEQISEFSKR VILADANLDK  1440
VLSAYNKHRD KPIREQAENI IHLFTLTNLG APAAFKYFDT TIDRKRYTST KEVLDATLIH  1500
QSITGLYETR IDLSQLGGDS RADYPYDVPD YASGSPKKKR KVSPGSGSET PGTSESATPE  1560
SNHDQEFDPP KVYPPVPAEK RKPIRVLSLF DGIATGLLVL KDLGIQVDRY IASEVCEDSI  1620
TVGMVRHQGK IMYVGDVRSV TQKHIQEWGP FDLVIGGSPC NDLSIVNPAR KGLYEGTGRL  1680
FFEFYRLLHD ARPKEGDDRP FFWLFENVVA MGVSDKRDIS RFLESNPVMI DAKEVSAAHR  1740
ARYFWGNLPG MNRPLASTVN DKLELQECLE HGRIAKFSKV RTITTRSNSI KQGKDQHFPV  1800
FMNEKEDILW CTEMERVFGF PVHYTDVSNM SRLARQRLLG RSWSVPVIRH LFAPLKEYFA  1860
CVSSGNSNAN SRGPSFSSGL VPLSLRGSHM GPMEIYKTVS AWKRQPVRVL SLFRNIDKVL  1920
KSLGFLESGS GSGGGTLKYV EDVTNVVRRD VEKWGPFDLV YGSTQPLGSS CDRCPGWYMF  1980
QFHRILQYAL PRQESQRPFF WIFMDNLLLT EDDQETTTRF LQTEAVTLQD VRGRDYQNAM  2040
RVWSNIPGLK SKHAPLTPKE EEYLQAQVRS RSKLDAPKVD LLVKNCLLPL REYFKYFSQN  2100
SLPLSRADPK KKRKVGSGAT NFSLLKQAGD VEENPGPSEL IKENMHMKLY MEGTVDNHHF  2160
KCTSEGEGKP YEGTQTMRIK VVEGGPLPFA FDILATSFLY GSKTFINHTQ GIPDFFKQSF  2220
PEGFTWERVT TYEDGGVLTA TQDTSLQDGC LIYNVKIRGV NFTSNGPVMQ KKTLGWEAFT  2280
ETLYPADGGL EGRNDMALKL VGGSHLIANI KTTYRSKKPA KNLKMPGVYY VDYRLERIKE  2340
ANNETYVEQH EVAVARYCDL PSKLGHKLN                                   2369

SEQ ID NO: 14           moltype = AA  length = 2391
FEATURE                 Location/Qualifiers
REGION                  1..2391
                        note = Synthetic polypeptide
source                  1..2391
                        mol_type = protein
```

```
                       organism = synthetic construct
SEQUENCE: 14
DAKSLTAWSR TLVTFKDVFV DFTREEWKLL DTAQQIVYRN VMLENYKNLV SLGYQLTKPD  60
VILRLEKGEE PGGPSSGAPP PSGGSPAGSP TSTEEGTSES ATPESGPGTS TEPSEGSAPG  120
SPAGSPTSTE EGTSTEPSEG SAPGTSTEPS EMDKKYSIGL AIGTNSVGWA VITDEYKVPS  180
KKFKVLGNTD RHSIKKNLIG ALLFDSGETA EATRLKRTAR RRYTRRKNRI CYLQEIFSNE  240
MAKVDDSFFH RLEESFLVEE DKKHERHPIF GNIVDEVAYH EKYPTIYHLR KKLVDSTDKA  300
DLRLIYLALA HMIKFRGHFL IEGDLNPDNS DVDKLFIQLV QTYNQLFEEN PINASGVDAK  360
AILSARLSKS RRLENLIAQL PGEKKNGLFG NLIALSLGLT PNFKSNFDLA EDAKLQLSKD  420
TYDDDLDNLL AQIGDQYADL FLAAKNLSDA ILLSDILRVN TEITKAPLSA SMIKRYDEHH  480
QDLTLLKALV RQQLPEKYKE IFFDQSKNGY AGYIDGGASQ EEFYKFIKPI LEKMDGTEEL  540
LVKLNREDLL RKQRTFDNGS IPHQIHLGEL HAILRRQEDF YPFLKDNREK IEKILTFRIP  600
YYVGPLARGN SRFAWMTRKS EETITPWNFE EVVDKGASAQ SFIERMTNFD KNLPNEKVLP  660
KHSLLYEYFT VYNELTKVKY VTEGMRKPAF LSGEQKKAIV DLLFKTNRKV TVKQLKEDYF  720
KKIECFDSVE ISGVEDRFNA SLGTYHDLLK IIKDKDFLDN EENEDILEDI VLTLTLFEDR  780
EMIEERLKTY AHLFDDKVMK QLKRRRYTGW GRLSRKLING IRDKQSGKTI LDFLKSDGFA  840
NRNFMQLIHD DSLTFKEDIQ KAQVSGQGDS LHEHIANLAG SPAIKKGILQ TVKVVDELVK  900
VMGRHKPENI VIEMARENQT TQKGQKNSRE RMKRIEEGIK ELGSQILKEH PVENTQLQNE  960
KLYLYYLQNG RDMYVDQELD INRLSDYDVD AIVPQSFLKD DSIDNKVLTR SDKNRGKSDN  1020
VPSEEVVKKM KNYWRQLLNA KLITQRKFDN LTKAERGGLS ELDKAGFIKR QLVETRQITK  1080
HVAQILDSRM NTKYDENDKL IREVKVITLK SKLVSDFRKD FQFYKVREIN NYHHAHDAYL  1140
NAVVGTALIK KYPKLESEFV YGDYKVYDVR KMIAKSEQEI GKATAKYFFY SNIMNFFKTE  1200
ITLANGEIRK RPLIETNGET GEIVWDKGRD FATVRKVLSM PQVNIVKKTE VQTGGFSKES  1260
ILPKRNSDKL IARKKDWDPK KYGGFDSPTV AYSVLVVAKV EKGKSKKLKS VKELLGITIM  1320
ERSSFEKNPI DFLEAKGYKE VKKDLIIKLP KYSLFELENG RKRMLASAGE LQKGNELALP  1380
SKYVNFLYLA SHYEKLKGSP EDNEQKQLFV EQHKHYLDEI IEQISEFSKR VILADANLDK  1440
VLSAYNKHRD KPIREQAENI IHLFTLTNLG APAAFKYFDT TIDRKRYTST KEVLDATLIH  1500
QSITGLYETR IDLSQLGGDS RADYPYDVPD YASGSPKKKR KVSPGSGSET PGTSESATPE  1560
SNHDQEFDPP KVYPPVPAEK RKPIRVLSLF DGIATGLLVL KDLGIQVDRY IASEVCEDSI  1620
TVGMVRHQGK IMYVGDVRSV TQKHIQEWGP FDLVIGGSPC NDLSIVNPAR KGLYEGTGRL  1680
FFEFYRLLHD ARPKEGDDRP FFWLFENVVA MGVSDKRDIS RFLESNPVMI DAKEVSAAHR  1740
ARYFWGNLPG MNRPLASTVN DKLELQECLE HGRIAKFSKV RTITTRSNSI KQGKDQHFPV  1800
FMNEKEDILW CTEMERVFGF PVHYTDVSNM SRLARQRLLG RSWSVPVIRH LFAPLKEYFA  1860
CVSSGNSNAN SRGPSFSSGL VPLSLRGSHM GPMEIYKTVS AWKRQPVRVL SLFRNIDKVL  1920
KSLGFLESGS GSGGGTLKYV EDVTNVVRRD VEKWGPFDLV YGSTQPLGSS CDRCPGWYMF  1980
QFHRILQYAL PRQESQRPFF WIFMDNLLLT EDDQETTTRF LQTEAVTLQD VRGRDYQNAM  2040
RVWSNIPGLK SKHAPLTPKE EEYLQAQVRS RSKLDAPKVD LLVKNCLLPL REYFKYFSQN  2100
SLPLSRADPK KKRKVGSGAT NFSLLKQAGD VEENPGPGSG ATNFSLLKQA GDVEENPGPS  2160
ELIKENMHMK LYMEGTVDNH HFKCTSEGEG KPYEGTQTMR IKVVEGGPLP FAFDILATSF  2220
LYGSKTFINH TQGIPDFFKQ SFPEGFTWER VTTYEDGGVL TATQDTSLQD GCLIYNVKIR  2280
GVNFTSNGPV MQKKTLGWEA FTETLYPADG GLEGRNDMAL KLVGGSHLIA NIKTTYRSKK  2340
PAKNLKMPGV YYVDYRLERI KEANNETYVE QHEVAVARYC DLPSKLGHKL N          2391

SEQ ID NO: 15          moltype = AA  length = 2345
FEATURE                Location/Qualifiers
REGION                 1..2345
                       note = Synthetic polypeptide
source                 1..2345
                       mol_type = protein
                       organism = synthetic construct
SEQUENCE: 15
NHDQEFDPPK VYPPVPAEKR KPIRVLSLFD GIATGLLVLK DLGIQVDRYI ASEVCEDSIT  60
VGMVRHQGKI MYVGDVRSVT QKHIQEWGPF DLVIGGSPCN DLSIVNPARK GLYEGTGRLF  120
FEFYRLLHDA RPKEGDDRPF FWLFENVVAM GVSDKRDISR FLESNPVMID AKEVSAAHRA  180
RYFWGNLPGM NRPLASTVND KLELQECLEH GRIAKFSKVR TITTRSNSIK QGKDQHFPVF  240
MNEKEDILWC TEMERVFGFP VHYTDVSNMS RLARQRLLGR SWSVPVIRHL FAPLKEYFAC  300
VSSGNSNANS RGPSFSSGLV PLSLRGSHMG PMEIYKTVSA WKRQPVRVLS LFRNIDKVLK  360
SLGFLESGSG SGGGTLKYVE DVTNVVRRDV EKWGPFDLVY GSTQPLGSSC DRCPGWYMFQ  420
FHRILQYALP RQESQRPFFW IFMDNLLLTE DDQETTTRFL QTEAVTLQDV RGRDYQNAMR  480
VWSNIPGLKS KHAPLTPKEE EYLQAQVRSR SKLDAPKVDL LVKNCLLPLR EYFKYFSQNS  540
LPLGGPSSGA PPPSGGSPAG SPTSTEEGTS ESATPESGPG TSTEPSEGSA PGSPAGSPTS  600
TEEGTSTEPS EGSAPGTSTE PSEMDKKYSI GLAIGTNSVG WAVITDEYKV PSKKFKVLGN  660
TDRHSIKKNL IGALLFDSGE TAEATRLKRT ARRRYTRRKN RICYLQEIFS NEMAKVDDSF  720
FHRLEESFLV EEDKKHERHP IFGNIVDEVA YHEKYPTIYH LRKKLVDSTD KADLRLIYLA  780
LAHMIKFRGH FLIEGDLNPD NSDVDKLFIQ LVQTYNQLFE ENPINASGVD AKAILSARLS  840
KSRRLENLIA QLPGEKKNGL FGNLIALSLG LTPNFKSNFD LAEDAKLQLS KDTYDDDLDN  900
LLAQIGDQYA DLFLAAKNLS DAILLSDILR VNTEITKAPL SASMIKRYDE HHQDLTLLKA  960
LVRQQLPEKY KEIFFDQSKN GYAGYIDGGA SQEEFYKFIK PILEKMDGTE ELLVKLNRED  1020
LLRKQRTFDN GSIPHQIHLG ELHAILRRQE DFYPFLKDNR EKIEKILTFR IPYYVGPLAR  1080
GNSRFAWMTR KSEETITPWN FEEVVDKGAS AQSFIERMTN FDKNLPNEKV LPKHSLLYEY  1140
FTVYNELTKV KYVTEGMRKP AFLSGEQKKA IVDLLFKTNR KVTVKQLKED YFKKIECFDS  1200
VEISGVEDRF NASLGTYHDL LKIIKDKDFL DNEENEDILE DIVLTLTLFE DREMIEERLK  1260
TYAHLFDDKV MKQLKRRRYT GWGRLSRKLI NGIRDKQSGK TILDFLKSDG FANRNFMQLI  1320
HDDSLTFKED IQKAQVSGQG DSLHEHIANL AGSPAIKKGI LQTVKVVDEL VKVMGRHKPE  1380
NIVIEMAREN QTTQKGQKNS RERMKRIEEG IKELGSQILK EHPVENTQLQ NEKLYLYYLQ  1440
NGRDMYVDQE LDINRLSDYD VDAIVPQSFL KDDSIDNKVL TRSDKNRGKS DNVPSEEVVK  1500
KMKNYWRQLL NAKLITQRKF DNLTKAERGG LSELDKAGFI KRQLVETRQI TKHVAQILDS  1560
RMNTKYDEND KLIREVKVIT LKSKLVSDFR KDFQFYKVRE INNYHHAHDA YLNAVVGTAL  1620
IKKYPKLESE FVYGDYKVYD VRKMIAKSEQ EIGKATAKYF FYSNIMNFFK TEITLANGEI  1680
```

```
RKRPLIETNG ETGEIVWDKG RDFATVRKVL SMPQVNIVKK TEVQTGGFSK ESILPKRNSD  1740
KLIARKKDWD PKKYGGFDSP TVAYSVLVVA KVEKGKSKKL KSVKELLGIT IMERSSFEKN  1800
PIDFLEAKGY KEVKKDLIIK LPKYSLFELE NGRKRMLASA GELQKGNELA LPSKYVNFLY  1860
LASHYEKLKG SPEDNEQKQL FVEQHKHYLD EIIEQISEFS KRVILADANL DKVLSAYNKH  1920
RDKPIREQAE NIIHLFTLTN LGAPAAFKYF DTTIDRKRYT STKEVLDATL IHQSITGLYE  1980
TRIDLSQLGG DAYPYDVPDY ASLGSGSPKK KRKVEDPKKK RKVDGIGSGS NGSSGSSELI  2040
KENMHMKLYM EGTVDNHHFK CTSEGEGKPY EGTQTMRIKV VEGGPLPFAF DILATSFLYG  2100
SKTFINHTQG IPDFFKQSFP EGFTWERVTT YEDGGVLTAT QDTSLQDGCL IYNVKIRGVN  2160
FTSNGPVMQK KTLGWEAFTE TLYPADGGLE GRNDMALKLV GGSHLIANIK TTYRSKKPAK  2220
NLKMPGVYYV DYRLERIKEA NNETYVEQHE VAVARYCDLP SKLGHKLNGG GGGMDAKSLT  2280
AWSRTLVTFK DVFVDFTREE WKLLDTAQQI VYRNVMLENY KNLVSLGYQL TKPDVILRLE  2340
KGEEP                                                              2345

SEQ ID NO: 16          moltype = AA  length = 71
FEATURE                Location/Qualifiers
REGION                 1..71
                       note = Synthetic polypeptide
source                 1..71
                       mol_type = protein
                       organism = synthetic construct
SEQUENCE: 16
DAKSLTAWSR TLVTFKDVFV DFTREEWKLL DTAQQIVYRN VMLENYKNLV SLGYQLTKPD  60
VILRLEKGEE P                                                       71

SEQ ID NO: 17          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 17
GGSGGGS                                                            7

SEQ ID NO: 18          moltype =   length =
SEQUENCE: 18
000

SEQ ID NO: 19          moltype = AA  length = 17
FEATURE                Location/Qualifiers
REGION                 1..17
                       note = Synthetic polypeptide
source                 1..17
                       mol_type = protein
                       organism = synthetic construct
SEQUENCE: 19
EASGSGRASP GIPGSTR                                                 17

SEQ ID NO: 20          moltype = AA  length = 4
FEATURE                Location/Qualifiers
REGION                 1..4
                       note = Synthetic polypeptide
source                 1..4
                       mol_type = protein
                       organism = synthetic construct
SEQUENCE: 20
SRAD                                                               4

SEQ ID NO: 21          moltype =   length =
SEQUENCE: 21
000

SEQ ID NO: 22          moltype =   length =
SEQUENCE: 22
000

SEQ ID NO: 23          moltype = AA  length = 1368
FEATURE                Location/Qualifiers
REGION                 1..1368
                       note = Synthetic polypeptide
source                 1..1368
                       mol_type = protein
                       organism = synthetic construct
SEQUENCE: 23
MDKKYSIGLA IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
```

```
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 24           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 24
YPYDVPDYA                                                         9

SEQ ID NO: 25           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 25
PKKKRKV                                                           7

SEQ ID NO: 26           moltype = AA  length = 301
FEATURE                 Location/Qualifiers
REGION                  1..301
                        note = Synthetic polypeptide
source                  1..301
                        mol_type = protein
                        organism = synthetic construct
SEQUENCE: 26
NHDQEFDPPK VYPPVPAEKR KPIRVLSLFD GIATGLLVLK DLGIQVDRYI ASEVCEDSIT  60
VGMVRHQGKI MYVGDVRSVT QKHIQEWGPF DLVIGGSPCN DLSIVNPARK GLYEGTGRLF  120
FEFYRLLHDA RPKEGDDRPF FWLFENVVAM GVSDKRDISR FLESNPVMID AKEVSAAHRA  180
RYFWGNLPGM NRPLASTVND KLELQECLEH GRIAKFSKVR TITTRSNSIK QGKDQHFPVF  240
MNEKEDILWC TEMERVFGFP VHYTDVSNMS RLARQRLLGR SWSVPVIRHL FAPLKEYFAC  300
V                                                                 301

SEQ ID NO: 27           moltype = AA  length = 27
FEATURE                 Location/Qualifiers
REGION                  1..27
                        note = Synthetic polypeptide
source                  1..27
                        mol_type = protein
                        organism = synthetic construct
SEQUENCE: 27
SSGNSNANSR GPSFSSGLVP LSLRGSH                                     27

SEQ ID NO: 28           moltype = AA  length = 215
FEATURE                 Location/Qualifiers
REGION                  1..215
                        note = Synthetic polypeptide
source                  1..215
                        mol_type = protein
                        organism = synthetic construct
SEQUENCE: 28
MGPMEIYKTV SAWKRQPVRV LSLFRNIDKV LKSLGFLESG SGSGGGTLKY VEDVTNVVRR  60
DVEKWGPFDL VYGSTQPLGS SCDRCPGWYM FQFHRILQYA LPRQESQRPF FWIFMDNLLL  120
TEDDQETTTR FLQTEAVTLQ DVRGRDYQNA MRVWSNIPGL KSKHAPLTPK EEEYLQAQVR  180
SRSKLDAPKV DLLVKNCLLP LREYFKYFSQ NSLPL                            215

SEQ ID NO: 29           moltype = AA  length = 19
FEATURE                 Location/Qualifiers
```

```
REGION                  1..19
                        note = Synthetic polypeptide
source                  1..19
                        mol_type = protein
                        organism = synthetic construct
SEQUENCE: 29
ATNFSLLKQA GDVEENPGP                                         19

SEQ ID NO: 30           moltype = AA  length = 232
FEATURE                 Location/Qualifiers
REGION                  1..232
                        note = Synthetic polypeptide
source                  1..232
                        mol_type = protein
                        organism = synthetic construct
SEQUENCE: 30
SELIKENMHM KLYMEGTVDN HHFKCTSEGE GKPYEGTQTM RIKVVEGGPL PFAFDILATS  60
FLYGSKTFIN HTQGIPDFFK QSFPEGFTWE RVTTYEDGGV LTATQDTSLQ DGCLIYNVKI  120
RGVNFTSNGP VMQKKTLGWE AFTETLYPAD GGLEGRNDMA LKLVGGSHLI ANIKTTYRSK  180
KPAKNLKMPG VYYVDYRLER IKEANNETYV EQHEVAVARY CDLPSKLGHK LN         232

SEQ ID NO: 31           moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 31
SGSETPGTSE SATPES                                            16

SEQ ID NO: 32           moltype = AA  length = 80
FEATURE                 Location/Qualifiers
REGION                  1..80
                        note = Synthetic polypeptide
source                  1..80
                        mol_type = protein
                        organism = synthetic construct
SEQUENCE: 32
GGPSSGAPPP SGGSPAGSPT STEEGTSESA TPESGPGTST EPSEGSAPGS PAGSPTSTEE  60
GTSTEPSEGS APGTSTEPSE                                        80

SEQ ID NO: 33           moltype = AA  length = 543
FEATURE                 Location/Qualifiers
REGION                  1..543
                        note = Synthetic polypeptide
source                  1..543
                        mol_type = protein
                        organism = synthetic construct
SEQUENCE: 33
NHDQEFDPPK VYPPVPAEKR KPIRVLSLFD GIATGLLVLK DLGIQVDRYI ASEVCEDSIT  60
VGMVRHQGKI MYVGDVRSVT QKHIQEWGPF DLVIGGSPCN DLSIVNPARK GLYEGTGRLF  120
FEFYRLLHDA RPKEGDDRPF FWLFENVVAM GVSDKRDISR FLESNPVMID AKEVSAAHRA  180
RYFWGNLPGM NRPLASTVND KLELQECLEH GRIAKFSKVR TITTRSNSIK QGKDQHFPVF  240
MNEKEDILWC TEMERVFGFP VHYTDVSNMS RLARQRLLGR SWSVPVIRHL FAPLKEYFAC  300
VSSGNSNANS RGPSFSSGLV PLSLRGSHMG PMEIYKTVSA WKRQPVRVLS LFRNIDKVLK  360
SLGFLESGSG SGGGTLKYVE DVTNVVRRDV EKWGPFDLVY GSTQPLGSSC DRCPGWYMFQ  420
FHRILQYALP RQESQRPFFW IFMDNLLLTE DDQETTTRFL QTEAVTLQDV RGRDYQNAMR  480
VWSNIPGLKS KHAPLTPKEE EYLQAQVRSR SKLDAPKVDL LVKNCLLPLR EYFKYFSQNS  540
LPL                                                          543

SEQ ID NO: 34           moltype = AA  length = 1307
FEATURE                 Location/Qualifiers
REGION                  1..1307
                        note = Synthetic polypeptide
source                  1..1307
                        mol_type = protein
                        organism = synthetic construct
SEQUENCE: 34
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
```

```
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLANLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN                1307

SEQ ID NO: 35          moltype = AA  length = 1228
FEATURE                Location/Qualifiers
REGION                 1..1228
                       note = Synthetic polypeptide
source                 1..1228
                       mol_type = protein
                       organism = synthetic construct
SEQUENCE: 35
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IARGERNLLY  840
IVVVDGKGNI VEQYSLNEII NNFNGIRIKT DYHSLLDKKE KERFEARQNW TSIENIKELK  900
AGYISQVVHK ICELVEKYDA VIALADLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                     1228

SEQ ID NO: 36          moltype = AA  length = 1314
FEATURE                Location/Qualifiers
REGION                 1..1314
                       note = Synthetic polypeptide
source                 1..1314
                       mol_type = protein
                       organism = synthetic construct
SEQUENCE: 36
MYPYDVPDYA SGSGMSIYQE FVNKYSLSKT LRFELIPQGK TLENIKARGL ILDDEKRAKD  60
YKKAKQIIDK YHQFFIEEIL SSVCISEDLL QNYSDVYFKL KKSDDDNLQK DFKSAKDTIK  120
KQISEYIKDS EKFKNLFNQN LIDAKKGQES DLILWLKQSK DNGIELFKAN SDITDIDEAL  180
EIIKSFKGWT TYFKGFHENR KNVYSSNDIP TSIIYRIVDD NLPKFLENKA KYESLKDKAP  240
EAINYEQIKK DLAEELTFDI DYKTSEVNQR VFSLDEVFEI ANFNNYLNQS GITKFNTIIG  300
GKFVNGENTK RKGINEYINL YSQQINDKTL KKYKMSVLFK QILSDTESKS FVIDKLEDDS  360
DVVTTMQSFY EQIAAFKTVE EKSIKETLSL LFDDLKAQKL DLSKIYFKND KSLTDLSQQV  420
FDDYSVIGTA VLEYITQQIA PKNLDNPSKK EQELIAKKTE KAKYLSLETI KLALEEFNKH  480
RDIDKQCRFE EILANFAAIP MIFDEIAQNK DNLAQISIKY QNQGKKDLLQ ASAEDDVKAI  540
KDLLDQTNNL LHKLKIFHIS QSEDKANILD KDEHFYLVFE ECYFELANIV PLYNKIRNYI  600
TQKPYSDEKF KLNFENSTLA NGWDKNKEPD NTAILFIKDD KYYLGVMNKK NNKIFDDKAI  660
KENKGEGYKK IVYKLLPGAN KMLPKVFFSA KSIKFYNPSE DILRIRNHST HTKNGSPQKG  720
YEKFEFNIED CRKFIDFYKQ SISKHPEWKD FGFRFSDTQR YNSIDEFYRE VENQGYKLTF  780
ENISESYIDS VVNQGKLYLF QIYNKDFSAY SKGRPNLHTL YWKALFDERN LQDVVYKLNG  840
EAELFYRKQS IPKKITHPAK EAIANKNKDN PKKESVFEYD LIKDKRFTED KFFFHCPITI  900
NFKSSGANKF NDEINLLLKE KANDVHILSI ARGERHLAYY TLVDGKGNII KQDTFNIIGN  960
DRMKTNYHDK LAAIEKDRDS ARKDWKKINN IKEMKEGYLS QVVHEIAKLV IEYNAIVVFE  1020
DLNFGFKRGR FKVEKQVYQK LEKMLIEKLN YLVFKDNEFD KTGGVLRAYQ LTAPFETFKK  1080
MGKQTGIIYY VPAGFTSKIC PVTGFVNQLY PKYESVSKSQ EFFSKFDKIC YNLDKGYFEF  1140
SFDYKNFGDK AAKGKWTIAS FGSRLINFRN SDKNHNWDTR EVYPTKELEK LLKDYSIEYG  1200
HGECIKAAIC GESDKKFFAK LTSVLNTILQ MRNSKTGTEL DYLISPVADV NGNFFDSRQA  1260
PKNMPQDADA NGAYHIGLKG LMLLGRIKNN QEGKKLNLVI KNEEYFEFVQ NRNN        1314

SEQ ID NO: 37          moltype = DNA  length = 19
FEATURE                Location/Qualifiers
misc_feature           1..19
                       note = Synthetic polynucleotide
source                 1..19
```

```
                         mol_type = other DNA
                         organism = synthetic construct
SEQUENCE: 37
actgcggaaa tttgagcgt                                                    19

SEQ ID NO: 38            moltype = DNA  length = 19
FEATURE                  Location/Qualifiers
misc_feature             1..19
                         note = Synthetic polynucleotide
source                   1..19
                         mol_type = other DNA
                         organism = synthetic construct
SEQUENCE: 38
acgctcaaat ttccgcagt                                                    19

SEQ ID NO: 39            moltype = DNA  length = 19
FEATURE                  Location/Qualifiers
misc_feature             1..19
                         note = Synthetic polynucleotide
source                   1..19
                         mol_type = other DNA
                         organism = synthetic construct
SEQUENCE: 39
aggcaatggc tgcacatgc                                                    19

SEQ ID NO: 40            moltype = DNA  length = 19
FEATURE                  Location/Qualifiers
misc_feature             1..19
                         note = Synthetic polynucleotide
source                   1..19
                         mol_type = other DNA
                         organism = synthetic construct
SEQUENCE: 40
gcatgtgcag ccattgcct                                                    19

SEQ ID NO: 41            moltype = DNA  length = 19
FEATURE                  Location/Qualifiers
misc_feature             1..19
                         note = Synthetic polynucleotide
source                   1..19
                         mol_type = other DNA
                         organism = synthetic construct
SEQUENCE: 41
gacgcttggt tctgaggag                                                    19

SEQ ID NO: 42            moltype = DNA  length = 19
FEATURE                  Location/Qualifiers
misc_feature             1..19
                         note = Synthetic polynucleotide
source                   1..19
                         mol_type = other DNA
                         organism = synthetic construct
SEQUENCE: 42
ctcctcagaa ccaagcgtc                                                    19

SEQ ID NO: 43            moltype = DNA  length = 19
FEATURE                  Location/Qualifiers
misc_feature             1..19
                         note = Synthetic polynucleotide
source                   1..19
                         mol_type = other DNA
                         organism = synthetic construct
SEQUENCE: 43
tccggaaacg cattcctct                                                    19

SEQ ID NO: 44            moltype = DNA  length = 19
FEATURE                  Location/Qualifiers
misc_feature             1..19
                         note = Synthetic polynucleotide
source                   1..19
                         mol_type = other DNA
                         organism = synthetic construct
SEQUENCE: 44
agaggaatgc gtttccgga                                                    19

SEQ ID NO: 45            moltype = DNA  length = 19
FEATURE                  Location/Qualifiers
misc_feature             1..19
                         note = Synthetic polynucleotide
```

```
source                  1..19
                        mol_type = other DNA
                        organism = synthetic construct
SEQUENCE: 45
ccgcgtcagc ccggcccgg                                              19

SEQ ID NO: 46           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 46
ccgggccggg ctgacgcgg                                              19

SEQ ID NO: 47           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 47
cgactcccgc tgggcctct                                              19

SEQ ID NO: 48           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 48
agaggcccag cgggagtcg                                              19

SEQ ID NO: 49           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 49
ccgttgcgcg ctcgctctc                                              19

SEQ ID NO: 50           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 50
gagagcgagc gcgcaacgg                                              19

SEQ ID NO: 51           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 51
ccgcgcatcc tgccaggcc                                              19

SEQ ID NO: 52           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 52
ggcctggcag gatgcgcgg                                              19

SEQ ID NO: 53           moltype = DNA  length = 19
FEATURE                 Location/Qualifiers
misc_feature            1..19
```

```
                        note = Synthetic polynucleotide
source                  1..19
                        mol_type = other DNA
                        organism = synthetic construct
SEQUENCE: 53
ccaacttggc gcgtttcgg                                                     19

SEQ ID NO: 54           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 54
ccgaaacgcg ccaagttgg                                                     19

SEQ ID NO: 55           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 55
accacgcgtc cgagtccgg                                                     19

SEQ ID NO: 56           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 56
ccggactcgg acgcgtggt                                                     19

SEQ ID NO: 57           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 57
tgctcattgt ccctggaca                                                     19

SEQ ID NO: 58           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 58
tgtccaggga caatgagca                                                     19

SEQ ID NO: 59           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 59
ggacaccctg ctcattgtc                                                     19

SEQ ID NO: 60           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 60
gacaatgagc agggtgtcc                                                     19

SEQ ID NO: 61           moltype = DNA  length = 19
FEATURE                 Location/Qualifiers
```

```
misc_feature          1..19
                      note = Synthetic polynucleotide
source                1..19
                      mol_type = other DNA
                      organism = synthetic construct
SEQUENCE: 61
accggcagcc tgcgcgtcc                                               19

SEQ ID NO: 62         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 62
ggacgcgcag gctgccggt                                               19

SEQ ID NO: 63         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 63
cgatgggcac ccactgctc                                               19

SEQ ID NO: 64         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 64
gagcagtggg tgcccatcg                                               19

SEQ ID NO: 65         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 65
ccttcacgtg gacgcgcag                                               19

SEQ ID NO: 66         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 66
ctgcgcgtcc acgtgaagg                                               19

SEQ ID NO: 67         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 67
cgtgaaggtg gaagccttc                                               19

SEQ ID NO: 68         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 68
gaaggcttcc accttcacg                                               19

SEQ ID NO: 69         moltype = DNA  length = 19
```

```
FEATURE               Location/Qualifiers
misc_feature          1..19
                      note = Synthetic polynucleotide
source                1..19
                      mol_type = other DNA
                      organism = synthetic construct
SEQUENCE: 69
ctccttggtc aggcgccgg                                                  19

SEQ ID NO: 70         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 70
ccggcgcctg accaaggag                                                  19

SEQ ID NO: 71         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 71
tggtcaggcg ccggttccg                                                  19

SEQ ID NO: 72         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 72
cggaaccggc gcctgacca                                                  19

SEQ ID NO: 73         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 73
tagaggtcgc cttctcctc                                                  19

SEQ ID NO: 74         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 74
gaggagaagg cgacctcta                                                  19

SEQ ID NO: 75         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 75
cgacgctcgg gtcgcggtg                                                  19

SEQ ID NO: 76         moltype = DNA  length = 19
FEATURE               Location/Qualifiers
misc_feature          1..19
                      note = Synthetic polynucleotide
source                1..19
                      mol_type = other DNA
                      organism = synthetic construct
SEQUENCE: 76
caccgcgacc cgagcgtcg                                                  19
```

```
SEQ ID NO: 77          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 77
atgctgtcgc cgcgcgggg                                            19

SEQ ID NO: 78          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 78
ccccgcgcgg cgacagcat                                            19

SEQ ID NO: 79          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 79
ctcaccctca ccggagcca                                            19

SEQ ID NO: 80          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 80
tggctccggt gagggtgag                                            19

SEQ ID NO: 81          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 81
ccgcaaactt tactcctta                                            19

SEQ ID NO: 82          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 82
taaggagtaa agtttgcgg                                            19

SEQ ID NO: 83          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 83
ctcctaagat tggcttcac                                            19

SEQ ID NO: 84          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 84
gtgaagccaa tcttaggag                                            19
```

```
SEQ ID NO: 85           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 85
ccggagccac tcctaagat                                            19

SEQ ID NO: 86           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 86
atcttaggag tggctccgg                                            19

SEQ ID NO: 87           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 87
ttctctaccc tacgtctca                                            19

SEQ ID NO: 88           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 88
tgagacgtag ggtagagaa                                            19

SEQ ID NO: 89           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 89
tacgtctcat tctccgcaa                                            19

SEQ ID NO: 90           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 90
ttgcggagaa tgagacgta                                            19

SEQ ID NO: 91           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 91
gctaggcctc cagcccttc                                            19

SEQ ID NO: 92           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 92
```

-continued

```
gaagggctgg aggcctagc                                                   19

SEQ ID NO: 93          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 93
acaggtggcg ccgcaactt                                                   19

SEQ ID NO: 94          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 94
aagttgcggc gccacctgt                                                   19

SEQ ID NO: 95          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 95
agccggaggc gcgagagtc                                                   19

SEQ ID NO: 96          moltype = DNA  length = 19
FEATURE                Location/Qualifiers
misc_feature           1..19
                       note = Synthetic polynucleotide
source                 1..19
                       mol_type = other DNA
                       organism = synthetic construct
SEQUENCE: 96
gactctcgcg cctccggct                                                   19
```

COMPOSITIONS AND METHODS FOR GENE EDITING

CROSS-REFERENCE TO RELATED APPLICATIONS

The application is a continuation of U.S. patent application Ser. No. 17/726,290, filed Apr. 21, 2022, which is a continuation of U.S. patent application Ser. No. 17/073,588, filed Oct. 19, 2020, now U.S. Pat. No. 11,434,491, issued on Sep. 6, 2022, which is continuation under 35 USC § 120 of International Application No. PCT/US2019/028377 filed Apr. 19, 2019, which claims priority to U.S. Application No. 62/660,023 filed Apr. 19, 2018, the disclosures of which are incorporated by reference herein in their entireties.

STATEMENT AS TO RIGHTS TO INVENTIONS MADE UNDER FEDERALLY SPONSORED RESEARCH AND DEVELOPMENT

This invention was made with government support under grant no. HR0011-17-2-0043 awarded by the Department of Defense, Defense Advanced Research Projects Agency and grant no. R01 DA036858 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-620001WO_SequenceListing_ST25.txt, created May 14, 2019, 382,771 bytes, machine format IBM-PC, MS Windows operating system, is hereby incorporated by reference.

BACKGROUND

Although considered a promising therapeutic approach for treatment of disease, genome editing carries inherent risks due to the potential for genotoxicity from double strand breaks. Further, genome editing often is associated with an all-or-none effect on the target gene (i.e., it produces a full knockout). In contrast, targeted epigenome engineering does not carry the risk of DSB-induced genotoxicity; further, it affords the opportunity to create a more graded effect on gene expression and thus function from a complete silencing through a less pronounced effect.

Provided herein are solutions to these and other needs in the art.

BRIEF SUMMARY

In an aspect is provided a fusion protein including a nuclease-deficient RNA-guided DNA endonuclease enzyme, a Krüppel associated box (KRAB) domain and a DNA methyltransferase domain. In an aspect is provided a fusion protein of any one of SEQ ID NOS:1-15.

In an aspect is provided a nucleic acid sequence encoding the fusion protein as described herein, including embodiments and aspects thereof.

In an aspect is provided a complex including a fusion protein as described herein, including embodiments and aspects thereof, and a polynucleotide including (1) a DNA-targeting sequence that is complementary to a target polynucleotide sequence and (2) a binding sequence for the nuclease-deficient RNA-guided DNA endonuclease enzyme, wherein the nuclease-deficient RNA-guided DNA endonuclease enzyme is bound to the polynucleotide via the binding sequence.

In an aspect is provided a vector including the nucleic acid sequence of a fusion protein as described herein, including embodiments and aspects thereof.

In an aspect is provided a cell including a fusion protein as described herein, including embodiments and aspects thereof, a nucleic acid as described herein, including embodiments and aspects thereof, a complex as described herein, including embodiments and aspects thereof, or a vector as described herein, including embodiments and aspects thereof.

In an aspect is provided a method of silencing a target nucleic acid sequence in a cell, including delivering a first polynucleotide encoding a fusion protein as described herein, including embodiments and aspects thereof, to a cell containing the target nucleic acid, and delivering to the cell a second polynucleotide including (i) a DNA-targeting sequence that is complementary to the target nucleic acid sequence, and (ii) a binding sequence for the nuclease-deficient RNA-guide DNA endonuclease enzyme. Without intending to be bound by any theory, it is believed that the fusion protein silences the target nucleic acid sequence in the cell by methylating a chromatin containing the target nucleic acid sequence and/or by introducing repressive chromatin marks to a chromatin containing the target nucleic acid sequence. Thus, in aspects, the fusion protein silences the target nucleic acid sequence in the cell by methylating a chromatin containing the target nucleic acid sequence and/or by introducing repressive chromatin marks to a chromatin containing the target nucleic acid sequence.

In an aspect is provided a method of silencing a target nucleic acid sequence in a cell, including delivering a complex as described herein, including embodiments and aspects thereof, to a cell containing the target nucleic acid, wherein the complex silences the target nucleic acid sequence in the cell. Without intending to be bound by any theory, it is believed that the complex silences the target nucleic acid sequence in the cell by methylating a chromatin containing the target nucleic acid sequence and/or by introducing repressive chromatin marks to a chromatin containing the target nucleic acid sequence. Thus, in aspects, the complex silences the target nucleic acid sequence in the cell by methylating a chromatin containing the target nucleic acid sequence and/or by introducing repressive chromatin marks to a chromatin containing the target nucleic acid sequence

BRIEF DESCRIPTION OF THE DRAWINGS

FIG. 1A is a schematic of an all-in-one protein (SEQ ID NO:1) of the disclosure that has the KRAB domain fused to the —N-terminus of dCas9 (SEQ ID NO:23), separated by a GGSGGGS (SEQ ID NO:17) linker, and Dnmt3A-Dnmt3L at the C-terminus of dCas9 (separated by a EASGSGRASPGIPGSTR (SEQ ID NO:19) linker). FIG. 1B provides schematics of dCas9-fused epigenetic modulators tested for permanent gene silencing. The dCas9-KRAB protein is adapted from Gilbert et al., Cell 2013 for CRISPR interference (CRISPRi) applications. The dCas9-Dnmt3A-Dnmt3L fusion is adapted from Stepper et al., Nucleic Acids Research, 2016. The inventors engineered a novel all-in-one protein that combines the KRAB domain (SEQ ID NO:16), dCas9 (D10A, H208A), Dnmt3A-Dnmt3L (SEQ ID NO:33; where Dnmt3A is SEQ ID NO:26 and Dnmt3L is SEQ ID NO:28) into one polypeptide. FIG. 1C provides schematics of a methylation-sensitive GFP reporter (adapted from Stelzer et al., Cell 2015) that was used to assess long-term silencing by the all-in-one protein. FIGS. 1D-1E provide a diagram and results of a hit-and-run experimental workflow in HEK293T cells expressing the GFP reporter shown in FIG. 3. FIG. 1D shows that plasmids were co-transfected into cells, one encoding the hit-and-run protein and the other plasmid encoding a sgRNA. FIG. 1E shows the results of the hit-and-run assay sorted for cells that were co-transfected with the all-in-one plasmid and sgRNA plasmid. FIG. 1F shows the results of the silencing of the GFP reporter is dependent on the sgRNA sequence.

FIGS. 2A-2C are representative flow cytometry data shown taken 22 days post-transfection following gene (CD29, CD81, CD151) targeting for long term silencing using the all-in-one protein. Quadrant IV represents cells that have turned off the gene, indicated by the percentage of cells with the gene off (i.e., 45%, 66%, and 53%, respectively). FIG. 2D provides quantification of silencing of CD29, CD81, and CD151 with three different sgRNA. FIG. 2E provides quantification of silencing of two or three genes simultaneously to show that the all-in-protein can be multiplexed by co-delivery of sgRNAs targeting different genes. FIG. 2F provides a plot representing a time point taken 9 months post transfection of the all-in-one protein and sgRNA targeting the CLTA gene, signifying that the majority of cells have stably turned off the CLTA gene.

FIGS. 3A-3C shows that harvested cells lost expression of CD29 (FIG. 3A), CD81 (FIG. 3B), and CD151 (FIG. 3C) thirty-six days post-transfection, as determined by their RNA expression profiles. FIGS. 3D-3F are volcano plots showing that the targeted genes CD29 (FIG. 3D), CD81 (FIG. 3E) and CD151 (FIG. 3F) is the only significant gene knocked down for each experiment, signifying high specificity of gene silencing. FIGS. 3G-3I provides quantification of transcript levels of CD151 (FIG. 3G), CD81 (GIF. 3H), and CD29 (FIG. 3I) showing more than 96% knockdown of each of the targeted genes.

FIGS. 4A-4F are flow cytometry plots showing BFP expression (which is fused to the all-in-one protein) in HeLa (cervical)(FIG. 4A), U2OS (bone)(FIG. 4B), and human induced pluripotent cells (iPSC) (FIG. 4C). FIGS. 4D-4F are the untransfected controls for FIGS. 4A-4C, respectively. FIG. 4G shows that stable silencing of endogenous genes in HeLa and U2OS cells, measured at 18 days post-transfection with the all-in-one protein, was achieved. In FIGS. 4A-4F, the x-axis is BFP (fused to all-in-one protein), and the y-axis is mCherry. FIG. 4H shows that gene silencing was detected 14 days post transfection by qPCR in AML12 mouse hepatocyte cell lines when targeting Pcsk9, Npc1, Spcs1 and Cd81.

FIGS. 6A-6-B shows the gene silencing results 18 days post-transfection of the fusion proteins of SEQ ID NOS:1-15 transfected into HEK293T cells for targeted silencing of the CLTA gene. The dCas9-KRAB and dCas9-Dnmt3A-Dnmt3L designs showed transient and lower efficiency of long term silencing. FIGS. 6C-6D provide a comparison of SEQ ID NO:1 (p'76) and SEQ ID NO:15 (p112) for silencing the HIST2H2BE (H2B) endogenous gene (FIG. 6C) and a synthetic Snrpn-GFP reporter gene (FIG. 6D) stably expressed in HEK293T cells. FIG. 6E provides a plot of protein expression (dotted lines) of p76 and p112 over the 50 day time course to turn off the HIST2H2BE (H2B) gene. Protein levels were measured by flow cytometry detection of BFP, which is co-expressed with the all-in-one protein.

FIG. 7A is a Western blot analysis of the all-in-one protein variants p76 and p90-p102 using an antibody against *Steptococcus pyogenes* Cas9. The top band represents full-length protein and smaller-sized bands represent proteolysis of the all-in-one protein. FIG. 7B is a Western blot analysis of all-in-one protein variants to detect free Dnmt3A that is cleaved from the fusion protein.

FIG. 8A is a schematic of a pooled screen to determine the optimal sgRNAs that leads to long term gene silencing. FIGS. 8B-8E are flow cytometry histograms of the percent of cells undergoing gene silencing four weeks post-transfection. Four HEK293T cell lines were used, each with a different gene with a GFP tag, including CLTA (FIG. 8B), VIM (FIG. 8C), HIST2H2BE (H2B) (FIG. 8D), and RAB11A (FIG. 8E).

FIG. 10A is a workflow of a pooled screen in HEK293T cells to determine optimal sgRNA targeting positions for the all-in-one protein, adapted from a previous ricin tiling screen in K562 cells to determine optimal sgRNAs for dCas9-KRAB (Gilbert, Horlbeck et al., Cell 2014). FIGS. 10B-10E are representative plots showing growth phenotypes for four genes, including ARL1 (FIG. 10B), EIF6 (FIG. 10C), SMC3 (FIG. 10D), HEATR1 (FIG. 10E), from existing dCas9-KRAB/CRISPRi datasets in K562 cells (Gilbert, Horlbeck et al., 2014) and with the all-in-one protein (bottom plot). Each dot represents an sgRNA. The TSS and annotated CpG island are shown for each gene.

FIG. 12A shows the in vitro transcription of two all-in-one variants (p102 and p112) show full length synthesis of each design. FIG. 12B provides a flow cytometry plot showing expression of p102 and p112 one day post-transfection of mRNA into HEK293T cells. FIG. 12C provides the time course of CLTA endogenous gene silencing in HEK293T cells after transfecting mRNA expressing the p102 and p112 all-in-one variants.

FIGS. 13A-13G describe controlled expression of the all-in-one protein by doxycycline induction. FIG. 13A provides flow cytometry plots showing induced expression of the all-in-one protein by addition of doxycycline in K562 cells that stably encode the all-in-one protein under a doxycycline-inducible promoter. The dotted line represents the baseline median BFP fluorescence without doxycycline administration. FIG. 13B provides a Western blot of cells to detect expression of the all-in-one protein before and after doxycycline treatment. FIGS. 13C-13F are flow cytometry plots of CD81 (FIGS. 13C-13D) and CD151 (FIGS. 13E-13F) knockdown 14 days post-doxycycline treatment of K562 cells. FIG. 13G shows the quantification of CD81 and CD151 knockdown 14 days post-doxycycline treatment or without doxycycline treatment.

DETAILED DESCRIPTION

Figure 1A:
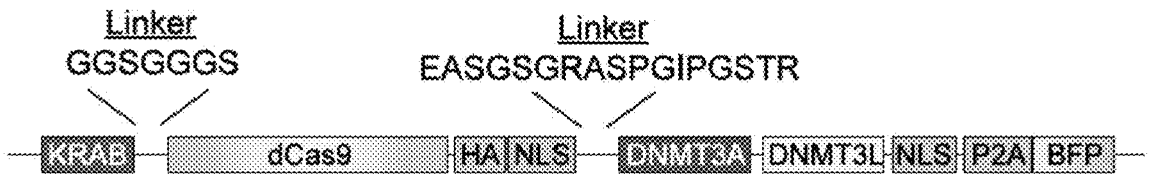
FIG. 1A-1F describe engineering of an all-in-one protein for long-term gene silencing.

The technology described herein allows for, inter alia, permanent silencing of genes in mammalian cells without generating double stranded DNA breaks in the host genome. In embodiments, the central component is a single polypeptide chain composed of catalytically inactive Cas9 (dCas9) fused to Dnmt3A, Dnmt3L, and a KRAB domain (herein referred to as an "all-in-one protein"). This fusion protein provided herein can be directed to a specific site in a mammalian genome using a single guide RNA (sgRNA) and may add DNA methylation and/or repressive chromatin marks to the site. In embodiments, the result is gene silencing that is inheritable across subsequent cell divisions. In embodiments, the fusion protein provided herein (and sgRNA) are only expressed transiently, bypassing the use of viral delivery methods to induce permanent silencing.

In embodiments, the fusion proteins provided herein provide a robust long-term or permanent silencing of endogenous gene expression by epigenome editing rather than genome editing. Both alleles of a gene may be targeted or a single pathogenic allele may be selectively targeted. In embodiments, an advantage of the fusion protein provided herein is that epigenetic editing is reversible and therefore inherently safer than genome editing. Thus, in embodiments, fusion protein provided herein is useful in prophylactic applications. For example, gene silencing can enable acute protection from an infection/biologic toxin and then be reversed after the risk of infection or intoxication is absent. Thus, in embodiments, fusion protein provided herein is useful for viral or toxin that enters a cell through interaction with a protein that is required for long term organ function or homeostasis. In embodiments, fusion protein provided herein is useful in genome editing based therapeutics.

In embodiments, permanent gene silencing in mammalian cells can be accomplished with two components: a single polypeptide chain composed of dCas9 fused to three epigenetic modulators and a single guide RNA that directs the protein to a specific site in the host genome. In embodiments, the components are only expressed transiently in the host cell, thus reducing toxicity and off-target events.

In embodiments, the fusion protein provided herein does not induce DNA breaks in the host cell for permanent gene silencing. In embodiments, the epigenetic marks that are added to the genomic site of interest are reversible, thus allowing for removal of any off-target events that may occur.

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acids, e.g. polynucleotides, contemplated herein include, but are not limited to, any type of RNA, e.g., mRNA, siRNA, miRNA, sgRNA, and guide RNA and any type of DNA, genomic DNA, plasmid DNA, and minicircle DNA, and any fragments thereof. In aspects, the nucleic acid is messenger RNA. In aspects, the messenger RNA is messenger ribonucleoprotein (RNP). The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, sgRNA, guide RNA, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In aspects, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

The term "complementary" or "complementarity" refers to the ability of a nucleic acid to form hydrogen bond(s) with another nucleic acid sequence by either traditional Watson-Crick or other non-traditional types. For example, the sequence A-G-T is complementary to the sequence T-C-A. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions (i.e., stringent hybridization conditions).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. One of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al., supra.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., sgRNA) may be detected by standard PCR or Northern blot methods well known in the art. See, Sambrook et al., 1989 Molecular Cloning: A Laboratory Manual, 18.1-18.88.

The term "transcriptional regulatory sequence" as provided herein refers to a segment of DNA that is capable of increasing or decreasing transcription (e.g., expression) of a specific gene within an organism. Non-limiting examples of transcriptional regulatory sequences include promoters, enhancers, and silencers.

The terms "transcription start site" and transcription initiation site" may be used interchangeably to refer herein to the 5' end of a gene sequence (e.g., DNA sequence) where RNA polymerase (e.g., DNA-directed RNA polymerase) begins synthesizing the RNA transcript. The transcription start site may be the first nucleotide of a transcribed DNA sequence where RNA polymerase begins synthesizing the RNA transcript. A skilled artisan can determine a transcription start site via routine experimentation and analysis, for example, by performing a run-off transcription assay or by definitions according to FANTOM5 database.

The term "promoter" as used herein refers to a region of DNA that initiates transcription of a particular gene. Promoters are typically located near the transcription start site of a gene, upstream of the gene and on the same strand (i.e., 5' on the sense strand) on the DNA. Promoters may be about 100 to about 1000 base pairs in length.

The term "enhancer" as used herein refers to a region of DNA that may be bound by proteins (e.g., transcription factors) to increase the likelihood that transcription of a gene will occur. Enhancers may be about 50 to about 1500 base pairs in length. Enhancers may be located downstream or upstream of the transcription initiation site that it regulates and may be several hundreds of base pairs away from the transcription initiation site.

The term "silencer" as used herein refers to a DNA sequence capable of binding transcription regulation factors known as repressors, thereby negatively effecting transcription of a gene. Silencer DNA sequences may be found at many different positions throughout the DNA, including, but not limited to, upstream of a target gene for which it acts to repress transcription of the gene (e.g., silence gene expression).

A "guide RNA" or "gRNA" as provided herein refers to any polynucleotide sequence having sufficient complementarity with a target polynucleotide sequence to hybridize with the target sequence and direct sequence-specific binding of a CRISPR complex to the target sequence. In aspects, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

In embodiments, the polynucleotide (e.g., gRNA) is a single-stranded ribonucleic acid. In aspects, the polynucleotide (e.g., gRNA) is 10, 20, 30, 40, 50, 60, 70, 80, 90, 100 or more nucleic acid residues in length. In aspects, the polynucleotide (e.g., gRNA) is from 10 to 30 nucleic acid residues in length. In aspects, the polynucleotide (e.g., gRNA) is 20 nucleic acid residues in length. In aspects, the length of the polynucleotide (e.g., gRNA) can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In aspects, the polynucleotide (e.g., gRNA) is from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In aspects, the polynucleotide (e.g., gRNA) is from 10 to 15, 10 to 20, 10 to 30, 10 to 40, or 10 to 50 residues in length.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may, in aspects, be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M) (see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

For specific proteins described herein (e.g., KRAB, dCas9, Dnmt3A, Dnmt3L), the named protein includes any of the protein's naturally occurring forms, or variants or homologs that maintain the protein activity (e.g., within at least 50%, 80%, 90%, 95%, 96%, 97%, 98%, 99% or 100% activity compared to the native protein). In aspects, variants or homologs have at least 50%, 55%, 60%, 65%, 70%, 75%, 80%, 85%, 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In aspects, the protein is the protein as identified by its NCBI sequence reference. In aspects, the protein is the protein as identified by its NCBI sequence reference or functional fragment or homolog thereof.

The term "Krüppel associated box domain" or "KRAB domain" as provided herein refers to a category of transcriptional repression domains present in approximately 400 human zinc finger protein-based transcription factors. KRAB domains typically include about 45 to about 75 amino acid residues. A description of KRAB domains, including their function and use, may be found, for example, in Ecco, G., Imbeault, M., Trono, D., KRAB zinc finger proteins, Development 144, 2017; Lambert et al. The human transcription factors, Cell 172, 2018; Gilbert et al., Cell (2013); and Gilbert et al., Cell (2014), all of which are incorporated herein by reference in their entirety. In aspects, the KRAB domain is a KRAB domain of Kox 1. In aspects, the KRAB domain includes the sequence set forth by SEQ ID NO:16. In aspects, the KRAB domain is the sequence of SEQ ID NO:16. In aspects, the KRAB domain includes an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:16. In aspects, the KRAB domain includes an amino acid sequence that has at least 75% sequence identity to SEQ ID NO:16. In aspects, the KRAB domain includes an amino acid sequence that has at least 80% sequence identity to SEQ ID NO:16. In aspects, the KRAB domain includes an amino acid sequence that has at least 85% sequence identity to SEQ ID NO:16. In aspects, the KRAB domain includes an amino acid sequence that has at least 90% sequence identity to SEQ ID NO:16. In aspects, the KRAB domain includes an amino acid sequence that has at least 95% sequence identity to SEQ ID NO:16.

The term "DNA methyltransferase" as provided herein refers to an enzyme that catalyzes the transfer of a methyl group to DNA. Non-limiting examples of DNA methyltransferases include Dnmt1, Dnmt3A, Dnmt3B, and Dnmt3L. In aspects, the DNA methyltransferase is a bacterial cytosine methyltransferase and/or a bacterial non-cytosine methyltransferase. Depending on the specific DNA methyltransferase, different regions of DNA are methylated. For example, Dnmt3A typically targets CpG dinucleotides for methylation. Through DNA methylation, DNA methyltransferases can modify the activity of a DNA segment (e.g., gene expression) without altering the DNA sequence. In aspects, DNA methylation results in repression of gene transcription and/or modulation of methylation sensitive transcription factors or CTCF. As described herein, fusion proteins may include one or more (e.g., two) DNA metyltransferases. When a DNA methyltransferase is included as part of a fusion protein, the DNA methyltransferase may be referred to as a "DNA methyltransferase domain." In aspects, a DNA methyltransferase domain includes one or more DNA methyltransferases. In aspects, a DNA methyltransferase domain includes two DNA methyltransferases. In aspects, the DNA methyltransferase domain is Dnmt3A. In aspects, the DNA methyltransferase domain has the amino acid sequence of SEQ ID NO:26. In aspects, the DNA methyltransferase domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:26. In aspects, the DNA methyltransferase domain has an amino acid sequence that has at least 75% sequence identity to SEQ ID NO:26. In aspects, the DNA methyltransferase domain has an amino acid sequence that has at least 80% sequence identity to SEQ ID NO:26. In aspects, the DNA methyltransferase domain has an amino acid sequence that has at least 85% sequence identity to SEQ ID NO:26. In aspects, the DNA methyltransferase domain has an amino acid sequence that has at least 90% sequence identity to SEQ ID NO:26. In aspects, the DNA methyltransferase domain has an amino acid sequence that has at least 95% sequence identity to SEQ ID NO:26. In aspects, the DNA methyltransferase domain is Dnmt3L. In aspects, the DNA methyltransferase domain has the amino acid sequence of SEQ ID NO:28. In aspects, the DNA methyltransferase domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:28. In aspects, the DNA methyltransferase domain has an amino acid sequence that has at least 75% sequence identity to SEQ ID NO:28. In aspects, the DNA methyltransferase domain has an amino acid sequence that has at least 80% sequence identity to SEQ ID NO:28. In aspects, the DNA methyltransferase domain has an amino acid sequence that has at least 85% sequence identity to SEQ ID NO:28. In aspects, the DNA methyltransferase domain has an amino acid sequence that has at least 90% sequence identity to SEQ ID NO:28. In aspects, the DNA methyltransferase domain has an amino acid sequence that has at least 95% sequence identity to SEQ ID NO:28. In aspects, the DNA methyltransferase domain includes Dnmt3A and Dnmt3L. In aspects, the DNA methyltransferase domain has the amino acid sequence of SEQ ID NO:33. In aspects, the DNA methyltransferase domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:33. In aspects, the DNA methyltransferase domain has an amino acid sequence that has at least 75% sequence identity to SEQ ID NO:33. In aspects, the DNA methyltransferase domain has an amino acid sequence that has at least 80% sequence identity to SEQ ID NO:33. In aspects, the DNA methyltransferase domain has an amino acid sequence that has at least 85% sequence identity to SEQ ID NO:33. In aspects, the DNA methyltransferase domain has an amino acid sequence that has at least 90% sequence identity to SEQ ID NO:33. In aspects, the DNA methyltransferase domain has an amino acid sequence that has at least 95% sequence identity to SEQ ID NO:33. A description of Dnmt3A-3L domain structure and use may be found, for example, in Siddique et al, Targeted methylation and gene silencing of VEGF-A in human cells by using a designed Dnmt3a-Dnmt3L single-chain fusion protein with increased DNA methylation activity, J. Mol. Biol. 425, 2013 and Stepper et al, Efficient targeted DNA methylation with chimeric dCas9-Dnmt3a-Dnmt3L methyltransferase, Nucleic Acids Res. 45, 2017, which are incorporated herein by reference in their entirety and for all purposes.

A "Dnmt3A", "Dnmt3a," "DNA (cytosine-5)-methyltransferase 3A" or "DNA methyltransferase 3a" protein as referred to herein includes any of the recombinant or naturally-occurring forms of the Dnmt3A enzyme or variants or homologs thereof that maintain Dnmt3A enzyme activity (e.g. within at least 50%, 55%, 60%, 65%, 70%, 75%, 80%, 85%, 90%, 91%, 92%, 93%, 94%, 95%, 96%, 97%, 98%, 99% or 100% activity compared to Dnmt3A). In aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring Dnmt3A protein. In aspects, the Dnmt3A protein is substantially identical to the protein identified by the UniProt reference number Q9Y6K1 or a variant or homolog having substantial identity thereto. In aspects, the Dnmt3A polypeptide is encoded by a nucleic acid sequence identified by the NCBI reference sequence Accession number NM 022552, homologs or functional fragments thereof. In aspects, Dnmt3A includes the sequence set forth by SEQ ID NO:26. In aspects, Dnmt3A is the sequence set forth by SEQ ID NO:26. In aspects, Dnmt3A has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:26. In aspects, the DNA methyltransferase domain has an amino acid sequence that has at least 75% sequence identity to SEQ ID NO:26. In aspects, the DNA methyltransferase domain has an amino acid sequence that has at least 80% sequence identity to SEQ ID NO:26. In aspects, the DNA methyltransferase domain has an amino acid sequence that has at least 85% sequence identity to SEQ ID NO:26. In aspects, Dnmt3A has an amino acid sequence that has at least 90% sequence identity to SEQ ID NO:26. In aspects, Dnmt3A has an amino acid sequence that has at least 95% sequence identity to SEQ ID NO:26.

A "Dnmt3L", "DNA (cytosine-5)-methyltransferase 3L" or "DNA methyltransferase 3L" protein as referred to herein includes any of the recombinant or naturally-occurring forms of the Dnmt3L enzyme or variants or homologs thereof that maintain Dnmt3L enzyme activity (e.g., within at least 50%, 55%, 60%, 65%, 70%, 75%, 80%, 85%, 90%, 91%, 92%, 93%, 94%, 95%, 96%, 97%, 98%, 99% or 100% activity compared to Dnmt3L). In aspects, the variants or homologs have at least 50%, 55%, 60%, 65%, 70%, 75%, 80%, 85%, 90%, 91%, 92%, 93%, 94%, 95%, 96%, 97%, 98%, 99% or 100% amino acid sequence identity across the whole sequence or a portion of the sequence (e.g., a 50, 100, 150 or 200 continuous amino acid portion) compared to a naturally occurring Dnmt3L protein. In aspects, the Dnmt3L protein is substantially identical to the protein identified by the UniProt reference number Q9CWR8 or a variant or homolog having substantial identity thereto. In aspects, the Dnmt3L protein is identical to the protein identified by the UniProt reference number Q9CWR8. In aspects, the Dnmt3L protein has at least 75% sequence identity to the amino acid sequence of the protein identified by the UniProt reference number Q9CWR8. In aspects, the Dnmt3L protein has at least 80% sequence identity to the amino acid sequence of the protein identified by the UniProt reference number Q9CWR8. In aspects, the Dnmt3L protein has at least 85% sequence identity to the amino acid sequence of the protein identified by the UniProt reference number Q9CWR8. In aspects, the Dnmt3L protein has at least 95% sequence identity to the amino acid sequence of the protein identified by the UniProt reference number Q9CWR8.

In aspects, the Dnmt3L protein is substantially identical to the protein identified by the UniProt reference number Q9UJW or a variant or homolog having substantial identity thereto. In aspects, the Dnmt3L protein is identical to the protein identified by the UniProt reference number Q9UJW. In aspects, the Dnmt3L protein has at least 50% sequence identity to the amino acid sequence of the protein identified by the UniProt reference number Q9UJW. In aspects, the Dnmt3L protein has at least 55% sequence identity to the protein identified by the UniProt reference number Q9UJW. In aspects, the Dnmt3L protein has at least 60% sequence identity to the amino acid sequence of the protein identified by the UniProt reference number Q9UJW. In aspects, the Dnmt3L protein has at least 65% sequence identity to the amino acid sequence of the protein identified by the UniProt reference number Q9UJW. In aspects, the Dnmt3L protein has at least 70% sequence identity to the amino acid sequence of the protein identified by the UniProt reference number Q9UJW. In aspects, the Dnmt3L protein has at least 75% sequence identity to the amino acid sequence of the protein identified by the UniProt reference number Q9UJW. In aspects, the Dnmt3L protein has at least 80% sequence identity to the amino acid sequence of the protein identified by the UniProt reference number Q9UJW. In aspects, the Dnmt3L protein has at least 85% sequence identity to the amino acid sequence of the protein identified by the UniProt reference number Q9UJW. In aspects, the Dnmt3L protein has at least 90% sequence identity to the amino acid sequence of the protein identified by the UniProt reference number Q9UJW. In aspects, the Dnmt3L protein has at least 95% sequence identity to the amino acid sequence of the protein identified by the UniProt reference number Q9UJW. In aspects, the Dnmt3L polypeptide is encoded by a nucleic acid sequence identified by the NCBI reference sequence Accession number NM 001081695, or homologs or functional fragments thereof. In aspects, Dnmt3L includes the sequence set forth by SEQ ID NO:28. In aspects, Dnmt3L is the sequence set forth by SEQ ID NO:28. In aspects, Dnmt3L has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:28. In aspects, Dnmt3L has an amino acid sequence that has at least 50% sequence identity to SEQ ID NO:28. In aspects, Dnmt3L has an amino acid sequence that has at least 55% sequence identity to SEQ ID NO:28. In aspects, Dnmt3L has an amino acid sequence that has at least 60% sequence identity to SEQ ID NO:28. In aspects, Dnmt3L has an amino acid sequence that has at least 65% sequence identity to SEQ ID NO:28. In aspects, Dnmt3L has an amino acid sequence that has at least 97% sequence identity to SEQ ID NO:28. In aspects, Dnmt3L has an amino acid sequence that has at least 75% sequence identity to SEQ ID NO:28. In aspects, Dnmt3L has an amino acid sequence that has at least 80% sequence identity to SEQ ID NO:28. In aspects, Dnmt3L has an amino acid sequence that has at least 85% sequence identity to SEQ ID NO:28. In aspects, Dnmt3L has an amino acid sequence that has at least 90% sequence identity to SEQ ID NO:28. In aspects, Dnmt3L has an amino acid sequence that has at least 95% sequence identity to SEQ ID NO:28.

The term "RNA-guided DNA endonuclease" and the like refer, in the usual and customary sense, to an enzyme that cleave a phosphodiester bond within a DNA polynucleotide chain, wherein the recognition of the phosphodiester bond is facilitated by a separate RNA sequence (for example, a single guide RNA).

The term "Class II CRISPR endonuclease" refers to endonucleases that have similar endonuclease activity as Cas9 and participate in a Class II CRISPR system. An example Class II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). The Cpf1 enzyme belongs to a putative type V CRISPR-Cas system. Both type II and type V systems are included in Class II of the CRISPR-Cas system.

A "nuclear localization sequence" or "nuclear localization signal" or "NLS" is a peptide that directs proteins to the nucleus. In aspects, the NLS includes five basic, positively charged amino acids. The NLS may be located anywhere on the peptide chain. In aspects, the NLS is an NLS derived from SV40. In aspects, the NLS includes the sequence set forth by SEQ ID NO:25. In aspects, the NLS is the sequence set forth by SEQ ID NO:25. In aspects, NLS has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO: 25. In aspects, NLS has an amino acid sequence that has at least 75% sequence identity to SEQ ID NO:25. In aspects, NLS has an amino acid sequence that has at least 80% sequence identity to SEQ ID NO:25. In aspects, NLS has an amino acid sequence that has at least 85% sequence identity to SEQ ID NO:25. In aspects, NLS has an amino acid sequence that has at least 90% sequence identity to SEQ ID NO:25. In aspects, NLS has an amino acid sequence that has at least 95% sequence identity to SEQ ID NO:25. In aspects, NLS has an amino acid sequence of SEQ ID NO:25.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include nanoparticle encapsulation of the nucleic acids that encode the fusion protein (e.g., lipid nanoparticles, gold nanoparticles, and the like), calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

A "peptide linker" as provided herein is a linker including a peptide moiety. In embodiments, the peptide linker is a divalent peptide, such as an amino acid sequence attached at the N-terminus and the C-terminus to the remainder of the compound (e.g., fusion protein provided herein. The peptide linker may be a peptide moiety (a divalent peptide moiety) capable of being cleaved (e.g., a P2A cleavable polypeptide). A peptide linker as provided herein may also be referred to interchangeably as an amino acid linker. In aspects, the peptide linker includes 1 to about 80 amino acid residues. In aspects, the peptide linker includes 1 to about 70 amino acid residues. In aspects, the peptide linker includes 1 to about 60 amino acid residues. In aspects, the peptide linker includes 1 to about 50 amino acid residues. In aspects, the peptide linker includes 1 to about 40 amino acid residues. In aspects, the peptide linker includes 1 to about 30 amino acid residues. In aspects, the peptide linker includes 1 to about 25 amino acid residues. In aspects, the peptide linker includes 1 to about 20 amino acid residues. In aspects, the peptide linker includes about 2 to about 20 amino acid residues. In aspects, the peptide linker includes about 2 to about 19 amino acid residues. In aspects, the peptide linker includes about 2 to about 18 amino acid residues. In aspects, the peptide linker includes about 2 to about 17 amino acid residues. In aspects, the peptide linker includes about 2 to about 16 amino acid residues. In aspects, the peptide linker includes about 2 to about 15 amino acid residues. In aspects, the peptide linker includes about 2 to about 14 amino acid residues. In aspects, the peptide linker includes about 2 to about 13 amino acid residues. In aspects, the peptide linker includes about 2 to about 12 amino acid residues. In aspects, the peptide linker includes about 2 to about 11 amino acid residues. In aspects, the peptide linker includes about 2 to about 10 amino acid residues. In aspects, the peptide linker includes about 2 to about 9 amino acid residues. In aspects, the peptide linker includes about 2 to about 8 amino acid residues. In aspects, the peptide linker includes about 2 to about 7 amino acid residues. In aspects, the peptide linker includes about 2 to about 6 amino acid residues. In aspects, the peptide linker includes about 2 to about 5 amino acid residues. In aspects, the peptide linker includes about 2 to about 4 amino acid residues. In aspects, the peptide linker includes about 2 to about 3 amino acid residues. In aspects, the peptide linker includes about 3 to about 19 amino acid residues. In aspects, the peptide linker includes about 3 to about 18 amino acid residues. In aspects, the peptide linker includes about 3 to about 17 amino acid residues. In aspects, the peptide linker includes about 3 to about 16 amino acid residues. In aspects, the peptide linker includes about 3 to about 15 amino acid residues. In aspects, the peptide linker includes about 3 to about 14 amino acid residues. In aspects, the peptide linker includes about 3 to about 13 amino acid residues. In aspects, the peptide linker includes about 3 to about 12 amino acid residues. In aspects, the peptide linker includes about 3 to about 11 amino acid residues. In aspects, the peptide linker includes about 3 to about 10 amino acid residues. In aspects, the peptide linker includes about 3 to about 9 amino acid residues. In aspects, the peptide linker includes about 3 to about 8 amino acid residues. In aspects, the peptide linker includes about 3 to about 7 amino acid residues. In aspects, the peptide linker includes about 3 to about 6 amino acid residues. In aspects, the peptide linker includes about 3 to about 5 amino acid residues. In aspects, the peptide linker includes about 3 to about 4 amino acid residues. In aspects, the peptide linker includes about 10 to about 20 amino acid residues. In aspects, the peptide linker includes about 15 to about 20 amino acid residues. In aspects, the peptide linker includes about 2 amino acid residues. In aspects, the peptide linker includes about 3 amino acid residues. In aspects, the peptide linker includes about 4 amino acid residues. In aspects, the peptide linker includes about 5 amino acid residues. In aspects, the peptide linker includes about 6 amino acid residues. In aspects, the peptide linker includes about 7 amino acid residues. In aspects, the peptide linker includes about 8 amino acid residues. In aspects, the peptide linker includes about 9 amino acid residues. In aspects, the peptide linker includes about 10 amino acid residues. In aspects, the peptide linker includes about 11 amino acid residues. In aspects, the peptide linker includes about 12 amino acid residues. In aspects, the peptide linker includes about 13 amino acid residues. In aspects, the peptide linker includes about 14 amino acid residues. In aspects, the peptide linker includes about 15 amino acid residues. In aspects, the peptide linker includes about 16 amino acid residues. In aspects, the peptide linker includes about 17 amino acid residues. In aspects, the peptide linker includes about 18 amino acid residues. In aspects, the peptide linker includes about 19 amino acid residues. In aspects, the peptide linker includes about 20 amino acid residues. In aspects, the peptide linker includes about 21 amino acid residues. In aspects, the peptide linker includes about 22 amino acid residues. In aspects, the peptide linker includes about 23 amino acid residues. In aspects, the peptide linker includes about 24 amino acid residues. In aspects, the peptide linker includes about 25 amino acid residues.

In aspects, the peptide linker includes the sequence set forth by SEQ ID NO:17. In aspects, the peptide linker is the sequence set forth by SEQ ID NO:17. In aspects, the peptide linker includes the sequence set forth by SEQ ID NO:18. In aspects, the peptide linker is the sequence set forth by SEQ ID NO:18. In aspects, the peptide linker includes the sequence set forth by SEQ ID NO:19. In aspects, the peptide linker is the sequence set forth by SEQ ID NO:19. In aspects, the peptide linker includes the sequence set forth by SEQ ID NO:20. In aspects, the peptide linker is the sequence set forth by SEQ ID NO:20. In aspects, the peptide linker includes the sequence set forth by SEQ ID NO:21. In aspects, the peptide linker is the sequence set forth by SEQ ID NO:21. In aspects, the peptide linker includes the sequence set forth by SEQ ID NO:22. In aspects, the peptide linker is the sequence set forth by SEQ ID NO:22. In aspects, the peptide linker includes the sequence set forth by SEQ ID NO:27. In aspects, the peptide linker is the sequence set forth by SEQ ID NO:27. In aspects, the peptide linker includes the sequence set forth by SEQ ID NO:24. In aspects, the peptide linker is the sequence set forth by SEQ ID NO:24. In aspects, the peptide linker includes the sequence set forth by SEQ ID NO:29. In aspects, the peptide linker is the sequence set forth by SEQ ID NO:29. In aspects, the peptide linker is an XTEN polypeptide. In aspects, the peptide linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:17, 18, 19, 20, 21, 22, 24, 27, or 29. In aspects, the peptide linker has an amino acid sequence that has at least 90% sequence identity to SEQ ID NO:17, 18, 19, 20, 21, 22, 24, 27, or 29.

In aspects, the peptide linker has an amino acid sequence that has at least 90% sequence identity to SEQ ID NO:17. In aspects, the peptide linker has an amino acid sequence that has at least 90% sequence identity to SEQ ID NO:18. In aspects, the peptide linker has an amino acid sequence that has at least 90% sequence identity to SEQ ID NO:19. In aspects, the peptide linker has an amino acid sequence that has at least 90% sequence identity to SEQ ID NO:20. In aspects, the peptide linker has an amino acid sequence that has at least 90% sequence identity to SEQ ID NO:21. In aspects, the peptide linker has an amino acid sequence that has at least 90% sequence identity to SEQ ID NO:22. In aspects, the peptide linker has an amino acid sequence that has at least 90% sequence identity to SEQ ID NO:24. In aspects, the peptide linker has an amino acid sequence that has at least 90% sequence identity to SEQ ID NO:27. In aspects, the peptide linker has an amino acid sequence that has at least 90% sequence identity to SEQ ID NO:29. In aspects, the peptide linker has an amino acid sequence that has at least 95% sequence identity to SEQ ID NO:17, 18, 19, 20, 21, 22, 24, 27, or 29. In aspects, the peptide linker has an amino acid sequence that has at least 95% sequence identity to SEQ ID NO:17. In aspects, the peptide linker has an amino acid sequence that has at least 95% sequence identity to SEQ ID NO:18. In aspects, the peptide linker has an amino acid sequence that has at least 95% sequence identity to SEQ ID NO:19. In aspects, the peptide linker has an amino acid sequence that has at least 95% sequence identity to SEQ ID NO:20. In aspects, the peptide linker has an amino acid sequence that has at least 95% sequence identity to SEQ ID NO:21. In aspects, the peptide linker has an amino acid sequence that has at least 95% sequence identity to SEQ ID NO:22. In aspects, the peptide linker has an amino acid sequence that has at least 95% sequence identity to SEQ ID NO:24. In aspects, the peptide linker has an amino acid sequence that has at least 95% sequence identity to SEQ ID NO:27. In aspects, the peptide linker has an amino acid sequence that has at least 95% sequence identity to SEQ ID NO:29.

The terms “XTEN,” “XTEN linker,” or “XTEN polypeptide” as used herein refer to an recombinant polypeptide (e.g. unstructured recombinant peptide) lacking hydrophobic amino acid residues. The development and use of XTEN can be found in, for example, Schellenberger et al., Nature Biotechnology 27, 1186-1190 (2009), which is incorporated herein by reference in its entirety and for all purposes. In aspects, the XTEN linker includes the sequence set forth by SEQ ID NO:31. In aspects, the XTEN linker is the sequence set forth by SEQ ID NO:31. In aspects, the XTEN linker includes the sequence set forth by SEQ ID NO:32. In aspects, the XTEN linker is the sequence set forth by SEQ ID NO:32. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:31. In aspects, the XTEN linker has an amino acid sequence that has at least 90% sequence identity to SEQ ID NO:31. In aspects, the XTEN linker has an amino acid sequence that has at least 95% sequence identity to SEQ ID NO:31. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:32. In aspects, the XTEN linker has an amino acid sequence that has at least 90% sequence identity to SEQ ID NO:32. In aspects, the XTEN linker has an amino acid sequence that has at least 95% sequence identity to SEQ ID NO:32.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y. $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

A detectable moiety is a monovalent detectable agent or a detectable agent capable of forming a bond with another composition. In aspects, the detectable agent is an HA tag. In aspects, the HA tag includes the sequence set forth by SEQ ID NO:24. In aspects, the HA tag is the sequence set forth by SEQ ID NO:24. In aspects, the HA tag has an amino acid sequence that has at least 80% sequence identity to SEQ ID NO:24. In aspects, the HA tag has an amino acid sequence that has at least 85% sequence identity to SEQ ID NO:24. In aspects, the HA tag has an amino acid sequence that has at least 90% sequence identity to SEQ ID NO:24. In aspects, the HA tag has an amino acid sequence that has at least 95% sequence identity to SEQ ID NO:24. In aspects, the detectable agent is blue fluorescent protein (BFP). In aspects, the BFP includes the sequence set forth by SEQ ID NO:30. In aspects, the BFP is the sequence set forth by SEQ ID NO:30. In aspects, the BFP has an amino acid sequence that has at least 80% sequence identity to SEQ ID NO:30. In aspects, the BFP has an amino acid sequence that has at least 85% sequence identity to SEQ ID NO:30. In aspects, the BFP has an amino acid sequence that has at least 90% sequence identity to SEQ ID NO:30. In aspects, the BFP has an amino acid sequence that has at least 95% sequence identity to SEQ ID NO:30.

Radioactive substances (e.g., radioisotopes) that may be used as imaging and/or labeling agents in accordance with the aspects of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y. $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, and $^{225}$Ac. Paramagnetic ions that may be used as additional imaging agents in accordance with the aspects of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

"Contacting" is used in accordance with its plain ordinary meaning and refers to the process of allowing at least two distinct species to become sufficiently proximal to react, interact or physically touch. It should be appreciated, however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a fusion protein as provided herein and a nucleic acid sequence (e.g., target DNA sequence).

As defined herein, the term "inhibition", "inhibit", "inhibiting," "repression," repressing," "silencing," "silence" and the like when used in reference to a composition as provided herein (e.g., fusion protein, complex, nucleic acid, vector) refer to negatively affecting (e.g., decreasing) the activity (e.g., transcription) of a nucleic acid sequence (e.g., decreasing transcription of a gene) relative to the activity of the nuclei acid sequence (e.g., transcription of a gene) in the absence of the composition (e.g., fusion protein, complex, nucleic acid, vector). In aspects, inhibition refers to reduction of a disease or symptoms of disease (e.g., cancer). Thus, inhibition includes, at least in part, partially or totally blocking activation (e.g., transcription), or decreasing, preventing, or delaying activation (e.g., transcription) of the nucleic acid sequence. The inhibited activity (e.g., transcription) may be 90%, 80%, 70%, 60%, 50%, 40%, 30%, 20%, 10%, or less than that in a control. In aspects, the inhibition is 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

Fusion Proteins

Provided herein are, inter alia, fusion proteins that can turn off genes permanently (e.g., irreversibly) and reversibly in mammalian cells using CRISPR-based epigenome editing. In embodiments, the fusion protein includes a single polypeptide fusion of four proteins (e.g., catalytically inactive Cas9 (e.g., dCas9), a KRAB domain, Dnmt3A and Dnmt3L) which can be expressed transiently in cells. The fusion protein can be directed to a specific site in a mammalian genome using a polynucleotide complementary to a target nucleic acid sequence (e.g., DNA sequence) and that further includes a sequence (i.e., binding sequence) capable of binding the fusion protein. Once properly positioned and without intending to be bound by a theory, the fusion protein adds DNA methylation and/or repressive chromatin marks to the target nucleic acid, resulting in gene silencing that is inheritable across subsequent cell divisions. In this way, the fusion protein can perform epigenome editing that bypasses the need to generate DNA double-strand breaks in the host genome, making it a safe and reversible way of manipulating the genome of a living organism.

In embodiments, the fustion protein comprises a nuclease-deficient RNA-guided DNA endonuclease enzyme; a KRAB domain, and a DNA methyltransferase domain. In aspects, the fusion protein comprises, from N-terminus to C-terminus, a DNA methyltransferase domain, a nuclease-deficient RNA-guided DNA endonuclease enzyme, and KRAB domain. In aspects, the fusion protein comprises, from N-terminus to C-terminus, a KRAB domain a nuclease-deficient RNA-guided DNA endonuclease enzyme, and a DNA methyltransferase domain. In embodiments, the fustion protein further comprises one or more peptide linkers. In aspects, the fusion protein further comprises one or more detectable tags. In aspects, the fusion protein further comprises one or more nuclear localization sequences. In aspects, the fusion protein further comprises one or more peptide linkers, one or more detectable tags, one or more nuclear localization sequences, or a combination of two or more of the foregoing. When the fusion protein comprises one or more peptide linkers, each peptide liner can be the same or different. When the fusion protein comprises one or more detectable tags, each detectable tag can be the same or different. In aspects, the fusion protein comprises from 1 to 10 detectable tags. In aspects, the fusion protein comprises from 1 to 9 detectable tags. In aspects, the fusion protein comprises from 1 to 8 detectable tags. In aspects, the fusion protein comprises from 1 to 7 detectable tags. In aspects, the fusion protein comprises from 1 to 6 detectable tags. In aspects, the fusion protein comprises from 1 to 5 detectable tags. In aspects, the fusion protein comprises from 1 to 4 detectable tags. In aspects, the fusion protein comprises from 1 to 3 detectable tags. In aspects, the fusion protein comprises from 1 to 2 detectable tags. In aspects, the fusion protein comprises 1 detectable tag. In aspects, the fusion protein comprises 2 detectable tags. In aspects, the fusion protein comprises 3 detectable tags. In aspects, the fusion protein comprises 4 detectable tags. In aspects, the fusion protein comprises 5 detectable tags.

In embodiments, the fusion protein comprises the structure: A-B-C, or B-A-C or C-A-B, or C-B-A, or B-C-A, or A-C-B; where A comprises a nuclease-deficient RNA-guided DNA endonuclease enzyme; B comprises a KRAB domain, C comprises a DNA methyltransferase domain; and wherein the component on the left is the N-terminus and the component on the right is the C-terminus. In aspects, the fusion protein further comprises one or more peptide linkers and one or more detectable tags. In aspects, A-B, B-A, B-C, C-B, A-C, and C-A are each independently linked together via a covalent bond, a peptide linker, a detectable tag, a nuclear localization sequence, or a combination of two or more thereof. The peptide linker can be any known in the art (e.g., P2A cleavable peptide, XTEN linker, and the like). In aspects, the fusion protein comprises other components, such as detectable tags (e.g., HA tag, blue fluorescent protein, and the like).

In embodiments, the fusion protein comprises the structure: A-$L_1$-B-$L_2$-C, where A comprises a nuclease-deficient RNA-guided DNA endonuclease enzyme; B comprises a KRAB domain, C comprises a DNA methyltransferase domain, $L_1$ is a covalent bond or a peptide linker, and $L_2$ is a covalent bond or a peptide linker; and where A is at the N-terminus and C is at the C-terminus. In aspects, A is covalently linked to B via a peptide linker. In aspects, A is covalently linked to B via a covalent bond. In aspects, B is covalently linked to C via a peptide linker. In aspects, B is covalently linked to C via a covalent bond. The peptide linker can be any known in the art (e.g., P2A cleavable peptide, XTEN linker, and the like). In aspects, the fusion protein comprises other components, such as detectable tags, nuclear localization sequences, and the like. In aspects, $L_1$ is a covalent bond, a peptide linker, a detectable tag, a nuclear localization sequence, or a combination thereof. In aspects, $L_2$ is a covalent bond, a peptide linker, a detectable tag, a nuclear localization sequence, or a combination thereof.

Figure 5:
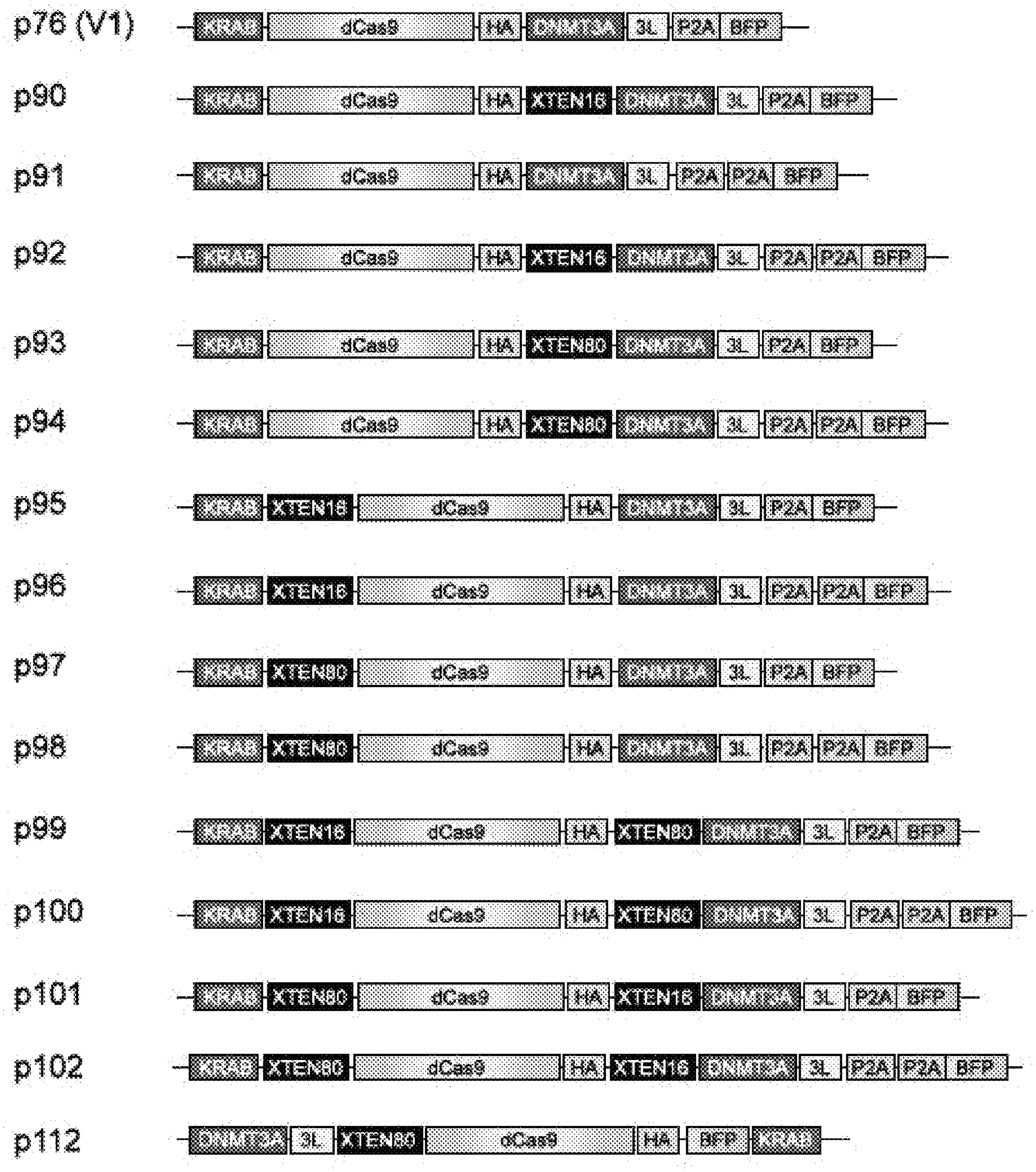
FIG. 5 provides schematics of the fusion proteins p76, p90-p102, and p112 which correspond to SEQ ID NOS:1-15, respectively.

In embodiments, the fusion protein comprises the structure: B-$L_1$-A-$L_2$-C, where A comprise a nuclease-deficient RNA-guided DNA endonuclease enzyme; B comprises a KRAB domain, C comprises a DNA methyltransferase domain, $L_1$ is a covalent bond or a peptide linker, and $L_2$ is a covalent bond or a peptide linker; and where B is at the N-terminus and C is at the C-terminus. In aspects, $L_1$ is a peptide linker. In aspects, $L_1$ is a covalent bond. In aspects, $L_2$ is a peptide linker. In aspects, $L_2$ is a covalent bond. The peptide linker can be any known in the art or described herein (e.g., P2A cleavable peptide, XTEN linker, and the like). In aspects, the fusion protein comprises other components, such as detectable tags. In aspects, $L_1$ is a covalent bond, a peptide linker, a detectable tag, or a combination thereof. In aspects, $L_2$ is a covalent bond, a peptide linker, a detectable tag, or a combination thereof. In aspects, the fusion protein further comprises a nuclear localization sequence. Exemplary fusion proteins comprising the structure: B-$L_1$-A-$L_2$-C include p76, p90, p91, p92, p93, p94, p95, p96, p9'7, p98, p99, p100, p101, and p102 (FIG. 5)

In embodiments, the fusion protein comprises the structure: B-$L_3$-A-$L_4$-C-$L_5$-D; where A comprises a nuclease-deficient RNA-guided DNA endonuclease enzyme; B comprises a KRAB domain, C comprises a DNA methyltransferase domain, D is absent or D comprises one or more detectable tags, $L_3$ comprises a covalent bond, a peptide linker, a detectable tag, or a combination of two or more thereof, $L_4$ comprises a covalent bond, a peptide linker, a detectable tag, or a combination of two or more thereof, $L_5$ is absent or $L_5$ comprises a covalent bond or a peptide linker; and where B is at the N-terminus and D is at the C-terminus. In aspects, $L_3$ is a peptide linker. In aspects, $L_3$ is a covalent bond. In aspects, $L_3$ comprises a peptide linker and a detectable tag. In aspects, $L_3$ comprises a detectable tag. In aspects, $L_4$ is a peptide linker. In aspects, $L_4$ comprises a peptide linker and a detectable tag. In aspects, $L_4$ is a covalent bond. In aspects, $L_4$ comprises a detectable tag. In aspects, $L_5$ is a peptide linker. In aspects, $L_5$ is a covalent bond. In aspects, D comprises one or a plurality of detectable tags. In aspects, D comprises one detectable tag. In aspects, D comprises two detectable tags. In aspects, D comprises three detectable tags. In aspects, D comprises a plurality of detectable tags. D can be any detectable tag known in the art and/or described herein (e.g., HA tag, blue fluorescent protein, and the like). In aspects $L_5$ and D are absent. When $L_3$, $L_4$, $L_5$, and D comprise two or more detectable tags, each detectable tag is the same or different. The peptide linker can be any known in the art and/or described herein (e.g., P2A cleavable peptide, XTEN linker, and the like). In aspects, the fusion protein further comprises a nuclear localization sequence. Exemplary fusion proteins comprising the structure: B-$L_3$-A-$L_4$-C-$L_5$-D include p'76, p90, p91, p92, p93, p94, p95, p96, p9'7, p98, p99, p100, p101, and p102, as shown in FIG. 5.

In embodiments, the fusion protein comprises the structure: C-$L_3$-A-$L_4$-B-$L_5$-D, where A comprises a nuclease-deficient RNA-guided DNA endonuclease enzyme; B comprises a KRAB domain, C comprises a DNA methyltransferase domain, D is absent or D comprises one or more detectable tags, $L_3$ comprises a covalent bond, a peptide linker, a detectable tag, or a combination of two or more thereof, $L_4$ comprises a covalent bond, a peptide linker, a detectable tag, or a combination of two or more thereof, $L_5$ is absent or $L_5$ comprises a covalent bond or a peptide linker; and where C is at the N-terminus and D is at the C-terminus. In aspects, $L_3$ is a peptide linker. In aspects, $L_3$ is a covalent bond. In aspects, $L_3$ comprises a detectable tag. In aspects, $L_3$ comprises a peptide linker and a detectable tag. In aspects, $L_4$ a peptide linker. In aspects, $L_4$ is a covalent bond. In aspects, $L_4$ comprises a detectable tag. In aspects, $L_4$ comprises a peptide linker and a detectable tag. In aspects, $L_5$ a peptide linker. In aspects, $L_5$ is a covalent bond. In aspects, D comprises one or a plurality of detectable tags. In aspects, D comprises one detectable tag. In aspects, D comprises two detectable tags. In aspects, D comprises three detectable tags. In aspects, D comprises a plurality of detectable tags. D can be any detectable tag known in the art and/or described herein (e.g., HA tag, blue fluorescent protein, and the like). In aspects $L_5$ and D are absent. When $L_3$, $L_4$, $L_5$, and D comprise two or more detectable tags, each detectable tag is the same or different. The peptide linker can be any known in the art and/or described herein (e.g., P2A cleavable peptide, XTEN linker, and the like). In aspects, the fusion protein further comprises a nuclear localization sequence. Exemplary fusion proteins comprising the structure: C-$L_3$-A-$L_4$-B-$L_5$-D include p112, as shown in FIG. 5.

The term "nuclease-deficient RNA-guided DNA endonuclease enzyme" and the like refer, in the usual and customary sense, to an RNA-guided DNA endonuclease (e.g. a mutated form of a naturally occurring RNA-guided DNA endonuclease) that targets a specific phosphodiester bond within a DNA polynucleotide, wherein the recognition of the phosphodiester bond is facilitated by a separate polynucleotide sequence (for example, a RNA sequence (e.g., single guide RNA (sgRNA)), but is incapable of cleaving the target phosphodiester bond to a significant degree (e.g. there is no measurable cleavage of the phosphodiester bond under physiological conditions). A nuclease-deficient RNA-guided DNA endonuclease thus retains DNA-binding ability (e.g. specific binding to a target sequence) when complexed with a polynucleotide (e.g., sgRNA), but lacks significant endonuclease activity (e.g. any amount of detectable endonuclease activity). In aspects, the nuclease-deficient RNA-guided DNA endonuclease enzyme is dCas9, ddCpf1, a nuclease-deficient Cas9 variant, or a nuclease-deficient Class II CRISPR endonuclease.

In embodiments, the nuclease-deficient RNA-guided DNA endonuclease enzyme is dCas9. The terms "dCas9" or "dCas9 protein" as referred to herein is a Cas9 protein in which both catalytic sites for endonuclease activity are defective or lack activity. In aspects, the dCas9 protein has mutations at positions corresponding to D10A and H840A of *S. pyogenes* Cas9. In aspects, the dCas9 protein lacks endonuclease activity due to point mutations at both endonuclease catalytic sites (RuvC and HNH) of wild type Cas9. The point mutations can be D10A and H840A. In aspects, the dCas9 has substantially no detectable endonuclease (e.g., endodeoxyribonuclease) activity. In aspects, dCas9 includes the amino acid sequence of SEQ ID NO:23. In aspects, dCas9 has the amino acid sequence of SEQ ID NO:23. In aspects, dCas9 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:23. In aspects, dCas9 has an amino acid sequence that has at least 75% sequence identity to SEQ ID NO:23. In aspects, dCas9 has an amino acid sequence that has at least 80% sequence identity to SEQ ID NO:23. In aspects, dCas9 has an amino acid sequence that has at least 85% sequence identity to SEQ ID NO:23. In aspects, dCas9 has an amino acid sequence that has at least 90% sequence identity to SEQ ID NO:23. In aspects, dCas9 has an amino acid sequence that has at least 95% sequence identity to SEQ ID NO:23.

A "CRISPR associated protein 9," "Cas9," "Csn1" or "Cas9 protein" as referred to herein includes any of the recombinant or naturally-occurring forms of the Cas9 endonuclease or variants or homologs thereof that maintain Cas9 endonuclease enzyme activity (e.g. within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In aspects, the Cas9 protein is substantially identical to the protein identified by the UniProt reference number Q99ZW2 or a variant or homolog having substantial identity thereto. In aspects, the Cas9 protein has at least 75% sequence identity to the amino acid sequence of the protein identified by the UniProt reference number Q99ZW2. In aspects, the Cas9 protein has at least 80% sequence identity to the amino acid sequence of the protein identified by the UniProt reference number Q99ZW2. In aspects, the Cas9 protein has at least 85% sequence identity to the amino acid sequence of the protein identified by the UniProt reference number Q99ZW2. In aspects, the Cas9 protein has at least 90% sequence identity to the amino acid sequence of the protein identified by the UniProt reference number Q99ZW2. In aspects, the Cas9 protein has at least 95% sequence identity to the amino acid sequence of the protein identified by the UniProt reference number Q99ZW2.

In embodiments, the nuclease-deficient RNA-guided DNA endonuclease enzyme is "ddCpf1" or "ddCas12a". The terms "DNAse-dead Cpf1" or "ddCpf1" refer to mutated Acidaminococcus sp. Cpf1 (AsCpf1) resulting in the inactivation of Cpf1 DNAse activity. In aspects, ddCpf1 includes an E993A mutation in the RuvC domain of AsCpf1. In aspects, the ddCpf1 has substantially no detectable endonuclease (e.g., endodeoxyribonuclease) activity. In aspects, ddCpf1 includes the amino acid sequence of SEQ ID NO:34. In aspects, ddCpf1 has the amino acid sequence of SEQ ID NO:34. In aspects, ddCpf1 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:34. In aspects, ddCpf1 has an amino acid sequence that has at least 75% sequence identity to SEQ ID NO:34. In aspects, ddCpf1 has an amino acid sequence that has at least 80% sequence identity to SEQ ID NO:34. In aspects, ddCpf1 has an amino acid sequence that has at least 85% sequence identity to SEQ ID NO:34. In aspects, ddCpf1 has an amino acid sequence that has at least 90% sequence identity to SEQ ID NO:34. In aspects, ddCpf1 has an amino acid sequence that has at least 95% sequence identity to SEQ ID NO:34.

In embodiments, the nuclease-deficient RNA-guided DNA endonuclease enzyme is dLbCpf1. The term "dLbCpf1: refers to mutated Cpf1 from Lachnospiraceae bacterium ND2006 (LbCpf1) that lacks DNAse activity. In aspects, dLbCpf1 includes a D832A mutation. In aspects, the dLbCpf1 has substantially no detectable endonuclease (e.g., endodeoxyribo-nuclease) activity. In aspects, dLbCpf1 includes the amino acid sequence of SEQ ID NO:35. In aspects, dLbCpf1 has the amino acid sequence of SEQ ID NO:35. In aspects, dLbCpf1 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:35. In aspects, dLbCpf1 has an amino acid sequence that has at least 75% sequence identity to SEQ ID NO:35. In aspects, dLbCpf1 has an amino acid sequence that has at least 80% sequence identity to SEQ ID NO:35. In aspects, dLbCpf1 has an amino acid sequence that has at least 85% sequence identity to SEQ ID NO:35. In aspects, dLbCpf1 has an amino acid sequence that has at least 90% sequence identity to SEQ ID NO:35. In aspects, dLbCpf1 has an amino acid sequence that has at least 95% sequence identity to SEQ ID NO:35.

In embodiments, the nuclease-deficient RNA-guided DNA endonuclease enzyme is dFnCpf1. The term "dFnCpf1" refers to mutated Cpf1 from *Francisella novicida* U112 (FnCpf1) that lacks DNAse activity. In aspects, dFnCpf1 includes a D917A mutation. In aspects, the dFnCpf1 has substantially no detectable endonuclease (e.g., endodeoxyribo-nuclease) activity. In aspects, dFnCpf1 includes the amino acid sequence of SEQ ID NO: 36. In aspects, dFnCpf1 has the amino acid sequence of SEQ ID NO: 36. In aspects, dFnCpf1 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:36. In aspects, dFnCpf1 has an amino acid sequence that has at least 75% sequence identity to SEQ ID NO:36. In aspects, dFnCpf1 has an amino acid sequence that has at least 80% sequence identity to SEQ ID NO:36. In aspects, dFnCpf1 has an amino acid sequence that has at least 85% sequence identity to SEQ ID NO:36. In aspects, dFnCpf1 has an amino acid sequence that has at least 90% sequence identity to SEQ ID NO:36. In aspects, dFnCpf1 has an amino acid sequence that has at least 95% sequence identity to SEQ ID NO:36.

A "Cpf1" or "Cpf1 protein" as referred to herein includes any of the recombinant or naturally-occurring forms of the Cpf1 (CRISPR from *Prevotella* and *Francisella* 1) endonuclease or variants or homologs thereof that maintain Cpf1 endonuclease enzyme activity (e.g. within at least 50%, 80%, 90%, 95%, 96%, 97%, 98%, 99% or 100% activity compared to Cpf1). In aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cpf1 protein. In aspects, the Cpf1 protein is substantially identical to the protein identified by the UniProt reference number U2UMQ6 or a variant or homolog having substantial identity thereto. In aspects, the Cpf1 protein is identical to the protein identified by the UniProt reference number U2UMQ6. In aspects, the Cpf1 protein has at least 75% sequence identity to the amino acid sequence of the protein identified by the UniProt reference number U2UMQ6. In aspects, the Cpf1 protein has at least 80% sequence identity to the amino acid sequence of the protein identified by the UniProt reference number U2UMQ6. In aspects, the Cpf1 protein is identical to the protein identified by the UniProt reference number U2UMQ6. In aspects, the Cpf1 protein has at least 85% sequence identity to the amino acid sequence of the protein identified by the UniProt reference number U2UMQ6. In aspects, the Cpf1 protein is identical to the protein identified by the UniProt reference number U2UMQ6. In aspects, the Cpf1 protein has at least 90% sequence identity to the amino acid sequence of the protein identified by the UniProt reference number U2UMQ6. In aspects, the Cpf1 protein is identical to the protein identified by the UniProt reference number U2UMQ6. In aspects, the Cpf1 protein has at least 95% sequence identity to the amino acid sequence of the protein identified by the UniProt reference number U2UMQ6.

In embodiments, the nuclease-deficient RNA-guided DNA endonuclease enzyme is a nuclease-deficient Cas9 variant. The term "nuclease-deficient Cas9 variant" refers to a Cas9 protein having one or more mutations that increase its binding specificity to PAM compared to wild type Cas9 and further include mutations that render the protein incapable of or having severely impaired endonuclease activity. Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). The binding specificity of nuclease-deficient Cas9 variants to PAM can be determined by any method known in the art. Descriptions and uses of known Cas9 variants may be found, for example, in Shmakov et al., Diversity and evolution of class 2 CRISPR-Cas systems. Nat. Rev. Microbiol. 15, 2017 and Cebrian-Serrano et al, CRISPR-Cas orthologues and variants: optimizing the repertoire, specificity and delivery of genome engineering tools. Mamm. Genome 7-8, 2017, which are incorporated herein by reference in their entirety and for all purposes. Exemplary Cas9 variants are listed in the Table 4 below.

TABLE 4

| Cas9 Variants | PAM domains | References |
|---|---|---|
| *Strep pyogenes* (Sp) Cas9 | NGG | Hsu et al. 2014 Cell |
| *Staph aureus* (Sa) Cas9 | NNGRRT or NNGRR NNGGGT, NNGAAT, NNGAGT (Zetsche) | Ran et al. 2015 Nature |
| SpCas9 VQR mutant (D1135V, R1335Q, T1337R) | NGAG > NGAT = NGAA > NGAC NGCG | Kleinstiver et al. 2015 Nature |
| SpCas9 VRER mutant (D1135V/G1218R/R1335E/T1337R) | NGCG | Kleinstiver et al. 2015 Nature |
| SpCas9 D1135E | NGG, greater fidelity, less cutting at NAG and NGA sites | Kleinstiver et al. 2015 Nature |
| eSpCas9 1.1 mutant (K848A/K1003A/R1060A) | NGG | Slaymaker et al. Science 2015 |
| SpCas9 HF1 (Q695A, Q926A, N497A, R661A) | NGG | Kleinstiver et al. 2016 Nature |
| AsCpf1 | TTTN (5' of sgRNA) | Zetsche et al. 2015 Cell |
| HypaCas9 (N692A, M694A, Q695A, H698A) | | Chen et al., Nature volume 550, pages 407-410 (19 Oct. 2017) |

In embodiments, the nuclease-deficient RNA-guided DNA endonuclease enzyme is a nuclease-deficient Class II CRISPR endonuclease. The term "nuclease-deficient Class II CRISPR endonuclease" as used herein refers to any Class II CRISPR endonuclease having mutations resulting in reduced, impaired, or inactive endonuclease activity.

In embodiments, the DNA methyltransferase domain is a Dnmt3A-3L domain. A "Dnmt3A-3L domain" as provided herein refers to a protein including both Dnmt3A and Dnmt3L. In aspects, the Dnmt3A and the Dnmt3L are covalently linked. In aspects, the Dnmt3A is covalently linked to the Dnmt3L through a peptide linker. In aspects, the peptide linker includes the sequence set forth by SEQ ID NO:27. In aspects, the peptide linker is the sequence set forth by SEQ ID NO:27. In aspects, the peptide linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:27. In aspects, the peptide linker has an amino acid sequence that has at least 90% sequence identity to SEQ ID NO:27. In aspects, the peptide linker has an amino acid sequence that has at least 95% sequence identity to SEQ ID NO:27. In aspects, the Dnmt3A-3L domain includes the sequence set forth by SEQ ID NO:33. In aspects, the Dnmt3A-3L domain is the sequence set forth by SEQ ID NO:33. In aspects, the Dnmt3A-3L domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:33. In aspects, the Dnmt3A-3L domain has an amino acid sequence that has at least 75% sequence identity to SEQ ID NO:33. In aspects, the Dnmt3A-3L domain has an amino acid sequence that has at least 80% sequence identity to SEQ ID NO:33. In aspects, the Dnmt3A-3L domain has an amino acid sequence that has at least 85% sequence identity to SEQ ID NO:33. In aspects, the Dnmt3A-3L domain has an amino acid sequence that has at least 90% sequence identity to SEQ ID NO:33. In aspects, the Dnmt3A-3L domain has an amino acid sequence that has at least 95% sequence identity to SEQ ID NO:33.

In embodiments, the peptide linker is a XTEN linker. In aspects, the XTEN linker includes about 16 to about 80 amino acid residues. In aspects, the XTEN linker includes about 17 to about 80 amino acid residues. In aspects, the XTEN linker includes about 18 to about 80 amino acid residues. In aspects, the XTEN linker includes about 19 to about 80 amino acid residues. In aspects, the XTEN linker includes about 20 to about 80 amino acid residues. In aspects, the XTEN linker includes about 30 to about 80 amino acid residues. In aspects, the XTEN linker includes about 40 to about 80 amino acid residues. In aspects, the XTEN linker includes about 50 to about 80 amino acid residues. In aspects, the XTEN linker includes about 60 to about 80 amino acid residues. In aspects, the XTEN linker includes about 70 to about 80 amino acid residues. In aspects, the XTEN linker includes about 16 to about 70 amino acid residues. In aspects, the XTEN linker includes about 16 to about 60 amino acid residues. In aspects, the XTEN linker includes about 16 to about 50 amino acid residues. In aspects, the XTEN linker includes about 16 to about 40 amino acid residues. In aspects, the XTEN linker includes about 16 to about 35 amino acid residues. In aspects, the XTEN linker includes about 16 to about 30 amino acid residues. In aspects, the XTEN linker includes about 16 to about 25 amino acid residues. In aspects, the XTEN linker includes about 16 to about 20 amino acid residues. In aspects, the XTEN linker includes about 16 amino acid residues. In aspects, the XTEN linker includes about 17 amino acid residues. In aspects, the XTEN linker includes about 18 amino acid residues. In aspects, the XTEN linker includes about 19 amino acid residues. In aspects, the XTEN linker includes about 20 amino acid residues.

In embodiments, the XTEN linker includes the sequence set forth by SEQ ID NO:31. In aspects, the XTEN linker is the sequence set forth by SEQ ID NO:31. In aspects, the XTEN linker includes the sequence set forth by SEQ ID NO:32. In aspects, the XTEN linker is the sequence set forth by SEQ ID NO:32. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:31. In aspects, the XTEN linker has an amino acid sequence that has at least 85% sequence identity to SEQ ID NO:31. In aspects, the XTEN linker has an amino acid sequence that has at least 90% sequence identity to SEQ ID NO:31. In aspects, the XTEN linker has an amino acid sequence that has at least 95% sequence identity to SEQ ID NO:31. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:32. In aspects, the XTEN linker has an amino acid sequence that has at least 75% sequence identity to SEQ ID NO:32. In aspects, the XTEN linker has an amino acid sequence that has at least 80% sequence identity to SEQ ID NO:32. In aspects, the XTEN linker has an amino acid sequence that has at least 85% sequence identity to SEQ ID NO:32. In aspects, the XTEN linker has an amino acid sequence that has at least 90% sequence identity to SEQ ID NO:32. In aspects, the XTEN linker has an amino acid sequence that has at least 95% sequence identity to SEQ ID NO:32.

The fusion protein may include amino acid sequences useful for targeting the fusion protein to specific regions of a cell (e.g., cytoplasm, nucleus). Thus, in aspects, the fusion protein further includes a nuclear localization signal (NLS) peptide. In aspects, the NLS includes the sequence set forth by SEQ ID NO:25. In aspects, the NLS is the sequence set forth by SEQ ID NO:25. In aspects, the NLS has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO: 25. In aspects, the NLS has an amino acid sequence that has at least 75% sequence identity to SEQ ID NO:25. In aspects, the NLS has an amino acid sequence that has at least 80% sequence identity to SEQ ID NO:25. In aspects, the NLS has an amino acid sequence that has at least 85% sequence identity to SEQ ID NO:25. In aspects, the NLS has an amino acid sequence that has at least 90% sequence identity to SEQ ID NO:25. In aspects, the NLS has an amino acid sequence that has at least 95% sequence identity to SEQ ID NO:25.

In embodiments, the fusion protein includes, from N-terminus to C-terminus, a KRAB domain, a nuclease-deficient RNA-guided DNA endonuclease enzyme, and a DNA methyltransferase domain.

In embodiments, the nuclease-deficient RNA-guided DNA endonuclease enzyme is dCas9 and the DNA methyltransferase domain is a Dnmt3A-3L domain.

In embodiments, the dCas9 is covalently linked to the KRAB domain via a peptide linker and wherein the dCas9 is covalently linked to the Dnmt3A-3L domain via a peptide linker.

In embodiments, peptide linker is an XTEN linker. In aspects, the XTEN linker includes the sequence set forth by SEQ ID NO:31. In aspects, the XTEN linker is the sequence set forth by SEQ ID NO:31. In aspects, the XTEN linker has an amino acid sequence that has at least 75% sequence identity to SEQ ID NO:31. In aspects, the XTEN linker has an amino acid sequence that has at least 80% sequence identity to SEQ ID NO:31. In aspects, the XTEN linker has an amino acid sequence that has at least 85% sequence identity to SEQ ID NO:31. In aspects, the XTEN linker has an amino acid sequence that has at least 90% sequence identity to SEQ ID NO:31. In aspects, the XTEN linker has an amino acid sequence that has at least 95% sequence identity to SEQ ID NO:31. In aspects, the XTEN linker includes the sequence set forth by SEQ ID NO:32. In aspects, the XTEN linker is the sequence set forth by SEQ ID NO:32. In aspects, the XTEN linker has an amino acid sequence that has at least 75% sequence identity to SEQ ID NO:32. In aspects, the XTEN linker has an amino acid sequence that has at least 80% sequence identity to SEQ ID NO:32. In aspects, the XTEN linker has an amino acid sequence that has at least 85% sequence identity to SEQ ID NO:32. In aspects, the XTEN linker has an amino acid sequence that has at least 90% sequence identity to SEQ ID NO:32. In aspects, the XTEN linker has an amino acid sequence that has at least 95% sequence identity to SEQ ID NO:32.

In embodiments, the fusion protein includes the amino acid sequence of SEQ ID NO: 1, 2, 3, 4, 5, 6, 7, 8, 9, 10, 11 12, 13, 14 or 15. In aspects, the fusion protein includes the amino acid sequence of SEQ ID NO:1. In aspects, the fusion protein is the amino acid sequence of SEQ ID NO:1. In aspects, the fusion protein includes the amino acid sequence of SEQ ID NO:2. In aspects, the fusion protein is the amino acid sequence of SEQ ID NO:2 In aspects, the fusion protein includes the amino acid sequence of SEQ ID NO:3. In aspects, the fusion protein is the amino acid sequence of SEQ ID NO:3. In aspects, the fusion protein includes the amino acid sequence of SEQ ID NO:4. In aspects, the fusion protein is the amino acid sequence of SEQ ID NO:4. In aspects, the fusion protein includes the amino acid sequence of SEQ ID NO:5. In aspects, the fusion protein is the amino acid sequence of SEQ ID NO:5. In aspects, the fusion protein includes the amino acid sequence of SEQ ID NO:6. In aspects, the fusion protein is the amino acid sequence of SEQ ID NO:6. In aspects, the fusion protein includes the amino acid sequence of SEQ ID NO:7. In aspects, the fusion protein is the amino acid sequence of SEQ ID NO:7. In aspects, the fusion protein includes the amino acid sequence of SEQ ID NO:8. In aspects, the fusion protein is the amino acid sequence of SEQ ID NO:8. In aspects, the fusion protein includes the amino acid sequence of SEQ ID NO:9. In aspects, the fusion protein is the amino acid sequence of SEQ ID NO:9. In aspects, the fusion protein includes the amino acid sequence of SEQ ID NO:10. In aspects, the fusion protein is the amino acid sequence of SEQ ID NO:10. In aspects, the fusion protein includes the amino acid sequence of SEQ ID NO:11. In aspects, the fusion protein is the amino acid sequence of SEQ ID NO:11. In aspects, the fusion protein includes the amino acid sequence of SEQ ID NO:12. In aspects, the fusion protein is the amino acid sequence of SEQ ID NO:12. In aspects, the fusion protein includes the amino acid sequence of SEQ ID NO:13. In aspects, the fusion protein is the amino acid sequence of SEQ ID NO:13. In aspects, the fusion protein includes the amino acid sequence of SEQ ID NO:14. In aspects, the fusion protein is the amino acid sequence of SEQ ID NO:14. In aspects, the fusion protein includes the amino acid sequence of SEQ ID NO:15. In aspects, the fusion protein is the amino acid sequence of SEQ ID NO:15.

In embodiments, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1, 2, 3, 4, 5, 6, 7, 8, 9, 10, 11 12, 13, 14 or 15. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:2. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:3. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:4. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:5. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:6. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:7. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:8. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:9. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:10. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:11. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:12. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:13. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:14. In aspects, the fusion protein includes an amino acid sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:15.

In embodiments, the fusion protein includes an amino acid sequence having at least 75% sequence identity to SEQ ID NO:1, 2, 3, 4, 5, 6, 7, 8, 9, 10, 11 12, 13, 14 or 15. In aspects, the fusion protein includes an amino acid sequence having at least 75% sequence identity to SEQ ID NO:1. In aspects, the fusion protein includes an amino acid sequence having at least 75% sequence identity to SEQ ID NO:2. In aspects, the fusion protein includes an amino acid sequence having at least 75% sequence identity to SEQ ID NO:3. In aspects, the fusion protein includes an amino acid sequence having at least 75% sequence identity to SEQ ID NO:4. In aspects, the fusion protein includes an amino acid sequence having at least 75% sequence identity to SEQ ID NO:5. In aspects, the fusion protein includes an amino acid sequence having at least 75% sequence identity to SEQ ID NO:6. In aspects, the fusion protein includes an amino acid sequence having at least 75% sequence identity to SEQ ID NO:7. In aspects, the fusion protein includes an amino acid sequence having at least 75% sequence identity to SEQ ID NO:8. In aspects, the fusion protein includes an amino acid sequence having at least 75% sequence identity to SEQ ID NO:9. In aspects, the fusion protein includes an amino acid sequence having at least 75% sequence identity to SEQ ID NO:10. In aspects, the fusion protein includes an amino acid sequence having at least 75% sequence identity to SEQ ID NO:11. In aspects, the fusion protein includes an amino acid sequence having at least 75% sequence identity to SEQ ID NO:12. In aspects, the fusion protein includes an amino acid sequence having at least 75% sequence identity to SEQ ID NO:13. In aspects, the fusion protein includes an amino acid sequence having at least 75% sequence identity to SEQ ID NO:14. In aspects, the fusion protein includes an amino acid sequence having at least 75% sequence identity to SEQ ID NO:15.

In embodiments, the fusion protein includes an amino acid sequence having at least 80%, sequence identity to SEQ ID NO:1, 2, 3, 4, 5, 6, 7, 8, 9, 10, 11 12, 13, 14 or 15. In aspects, the fusion protein includes an amino acid sequence having at least 80% sequence identity to SEQ ID NO:1. In aspects, the fusion protein includes an amino acid sequence having at least 80% sequence identity to SEQ ID NO:2. In aspects, the fusion protein includes an amino acid sequence having at least 80% sequence identity to SEQ ID NO:3. In aspects, the fusion protein includes an amino acid sequence having at least 80% sequence identity to SEQ ID NO:4. In aspects, the fusion protein includes an amino acid sequence having at least 80% sequence identity to SEQ ID NO:5. In aspects, the fusion protein includes an amino acid sequence having at least 80% sequence identity to SEQ ID NO:6. In aspects, the fusion protein includes an amino acid sequence having at least 80% sequence identity to SEQ ID NO:7. In aspects, the fusion protein includes an amino acid sequence having at least 80% sequence identity to SEQ ID NO:8. In aspects, the fusion protein includes an amino acid sequence having at least 80% sequence identity to SEQ ID NO:9. In aspects, the fusion protein includes an amino acid sequence having at least 80% sequence identity to SEQ ID NO:10. In aspects, the fusion protein includes an amino acid sequence having at least 80% sequence identity to SEQ ID NO:11. In aspects, the fusion protein includes an amino acid sequence having at least 80% sequence identity to SEQ ID NO:12. In aspects, the fusion protein includes an amino acid sequence having at least 80% sequence identity to SEQ ID NO:13. In aspects, the fusion protein includes an amino acid sequence having at least 80% sequence identity to SEQ ID NO:14. In aspects, the fusion protein includes an amino acid sequence having at least 80% sequence identity to SEQ ID NO:15.

In embodiments, the fusion protein includes an amino acid sequence having at least 85% sequence identity to SEQ ID NO:1, 2, 3, 4, 5, 6, 7, 8, 9, 10, 11 12, 13, 14 or 15. In aspects, the fusion protein includes an amino acid sequence having at least 85% sequence identity to SEQ ID NO:1. In aspects, the fusion protein includes an amino acid sequence having at least 85% sequence identity to SEQ ID NO:2. In aspects, the fusion protein includes an amino acid sequence having at least 85% sequence identity to SEQ ID NO:3. In aspects, the fusion protein includes an amino acid sequence having at least 85% sequence identity to SEQ ID NO:4. In aspects, the fusion protein includes an amino acid sequence having at least 85% sequence identity to SEQ ID NO:5. In aspects, the fusion protein includes an amino acid sequence having at least 85% sequence identity to SEQ ID NO:6. In aspects, the fusion protein includes an amino acid sequence having at least 85% sequence identity to SEQ ID NO:7. In aspects, the fusion protein includes an amino acid sequence having at least 85% sequence identity to SEQ ID NO:8. In aspects, the fusion protein includes an amino acid sequence having at least 85% sequence identity to SEQ ID NO:9. In aspects, the fusion protein includes an amino acid sequence having at least 85% sequence identity to SEQ ID NO:10.

In aspects, the fusion protein includes an amino acid sequence having at least 85% sequence identity to SEQ ID NO:11. In aspects, the fusion protein includes an amino acid sequence having at least 85% sequence identity to SEQ ID NO:12. In aspects, the fusion protein includes an amino acid sequence having at least 85% sequence identity to SEQ ID NO:13. In aspects, the fusion protein includes an amino acid sequence having at least 85% sequence identity to SEQ ID NO:14. In aspects, the fusion protein includes an amino acid sequence having at least 85% sequence identity to SEQ ID NO:15.

In embodiments, the fusion protein includes an amino acid sequence having at least 90% sequence identity to SEQ ID NO:1, 2, 3, 4, 5, 6, 7, 8, 9, 10, 11 12, 13, 14 or 15. In aspects, the fusion protein includes an amino acid sequence having at least 90% sequence identity to SEQ ID NO:1. In aspects, the fusion protein includes an amino acid sequence having at least 90% sequence identity to SEQ ID NO:2. In aspects, the fusion protein includes an amino acid sequence having at least 90% sequence identity to SEQ ID NO:3. In aspects, the fusion protein includes an amino acid sequence having at least 90% sequence identity to SEQ ID NO:4. In aspects, the fusion protein includes an amino acid sequence having at least 90% sequence identity to SEQ ID NO:5. In aspects, the fusion protein includes an amino acid sequence having at least 90% sequence identity to SEQ ID NO:6. In aspects, the fusion protein includes an amino acid sequence having at least 90% sequence identity to SEQ ID NO:7. In aspects, the fusion protein includes an amino acid sequence having at least 90% sequence identity to SEQ ID NO:8. In aspects, the fusion protein includes an amino acid sequence having at least 90% sequence identity to SEQ ID NO:9. In aspects, the fusion protein includes an amino acid sequence having at least 90% sequence identity to SEQ ID NO:10. In aspects, the fusion protein includes an amino acid sequence having at least 90% sequence identity to SEQ ID NO:11. In aspects, the fusion protein includes an amino acid sequence having at least 90% sequence identity to SEQ ID NO:12. In aspects, the fusion protein includes an amino acid sequence having at least 90% sequence identity to SEQ ID NO:13. In aspects, the fusion protein includes an amino acid sequence having at least 90% sequence identity to SEQ ID NO:14. In aspects, the fusion protein includes an amino acid sequence having at least 90% sequence identity to SEQ ID NO:15.

In embodiments, the fusion protein includes an amino acid sequence having at least 95% sequence identity to SEQ ID NO:1, 2, 3, 4, 5, 6, 7, 8, 9, 10, 11 12, 13, 14 or 15. In aspects, the fusion protein includes an amino acid sequence having at least 95% sequence identity to SEQ ID NO:1. In aspects, the fusion protein includes an amino acid sequence having at least 95% sequence identity to SEQ ID NO:2. In aspects, the fusion protein includes an amino acid sequence having at least 95% sequence identity to SEQ ID NO:3. In aspects, the fusion protein includes an amino acid sequence having at least 95% sequence identity to SEQ ID NO:4. In aspects, the fusion protein includes an amino acid sequence having at least 95% sequence identity to SEQ ID NO:5. In aspects, the fusion protein includes an amino acid sequence having at least 95% sequence identity to SEQ ID NO:6. In aspects, the fusion protein includes an amino acid sequence having at least 95% sequence identity to SEQ ID NO:7. In aspects, the fusion protein includes an amino acid sequence having at least 95% sequence identity to SEQ ID NO:8. In aspects, the fusion protein includes an amino acid sequence having at least 95% sequence identity to SEQ ID NO:9. In aspects, the fusion protein includes an amino acid sequence having at least 95% sequence identity to SEQ ID NO:10. In aspects, the fusion protein includes an amino acid sequence having at least 95% sequence identity to SEQ ID NO:11. In aspects, the fusion protein includes an amino acid sequence having at least 95% sequence identity to SEQ ID NO:12. In aspects, the fusion protein includes an amino acid sequence having at least 95% sequence identity to SEQ ID NO:13. In aspects, the fusion protein includes an amino acid sequence having at least 95% sequence identity to SEQ ID NO:14. In aspects, the fusion protein includes an amino acid sequence having at least 95% sequence identity to SEQ ID NO:15.

Complexes

In order for the fusion protein to carry out epigenome editing, the fusion protein interacts with (e.g. is non-covalently bound to) a polynucleotide (e.g., sgRNA) that is complementary to a target polynucleotide sequence (e.g., a target DNA sequence to be edited) and further includes a sequence (i.e., a binding sequence) to which the nuclease-deficient RNA-guided DNA endonuclease enzyme of the fusion protein as described herein can bind. By forming this complex, the fusion protein is appropriately positioned to perform epigenome editing. The term "complex" refers to a composition that includes two or more components, where the components bind together to make a functional unit. In aspects, a complex described herein includes a fusion protein described herein and a polynucleotide described herein. Thus, in an aspect is provided a fusion protein as described herein, including embodiments and aspects thereof, and a polynucleotide including: (1) a DNA-targeting sequence that is complementary to a target polynucleotide sequence; and (2) a binding sequence for the nuclease-deficient RNA-guided DNA endonuclease enzyme, wherein the nuclease-deficient RNA-guided DNA endonuclease enzyme is bound to the polynucleotide via the binding sequence (e.g., an amino acid sequence capable of binding to the DNA-targeting sequence).

A DNA-targeting sequence refers to a polynucleotide that includes a nucleotide sequence complementary to the target polynucleotide sequence (DNA or RNA). In aspects, a DNA-targeting sequence can be a single RNA molecule (single RNA polynucleotide), which may include a "single-guide RNA," or "sgRNA." In aspects, the DNA-targeting sequence includes two RNA molecules (e.g., joined together via hybridization at the binding sequence (e.g., dCas9-binding sequence). In aspects, the DNA-targeting sequence (e.g., sgRNA) is at least 50%, 55%, 60%, 65%, 70%, 75%, 80%, 85%, 90%, 95%, 96%, 97%, 98% or 99% complementary to the target polynucleotide sequence. In aspects, the DNA-targeting sequence (e.g., sgRNA) is at least 50%, 55%, 60%, 65%, 70%, 75%, 80%, 85%, 90%, 95%, 96%, 97%, 98% or 99% complementary to the sequence of a cellular gene. In aspects, the DNA-targeting sequence (e.g., sgRNA) binds a cellular gene sequence. In aspects, the DNA-targeting sequence (e.g., sgRNA) is at least 75% complementary to the sequence of a cellular gene. In aspects, the DNA-targeting sequence (e.g., sgRNA) is at least 80% complementary to the sequence of a cellular gene. In aspects, the DNA-targeting sequence (e.g., sgRNA) binds a cellular gene sequence. In aspects, the DNA-targeting sequence (e.g., sgRNA) is at least 85% complementary to the sequence of a cellular gene. In aspects, the DNA-targeting sequence (e.g., sgRNA) binds a cellular gene sequence. In aspects, the DNA-targeting sequence (e.g., sgRNA) is at least 90% complementary to the sequence of a cellular gene. In aspects, the DNA-targeting sequence (e.g., sgRNA) binds a cellular gene sequence. In aspects, the DNA-targeting sequence (e.g., sgRNA) is at least 95% complementary to the sequence of a cellular gene. In aspects, the DNA-targeting sequence (e.g., sgRNA) binds a cellular gene sequence.

A "target polynucleotide sequence" as provided herein is a nucleic acid sequence present in, or expressed by, a cell, to which a guide sequence (or a DNA-targeting sequence) is designed to have complementarity, where hybridization between a target sequence and a guide sequence (or a DNA-targeting sequence) promotes the formation of a CRISPR complex. Full complementarity is not necessarily required, provided there is sufficient complementarity to cause hybridization and promote formation of a CRISPR complex. In aspects, the target polynucleotide sequence is an exogenous nucleic acid sequence. In aspects, the target polynucleotide sequence is an endogenous nucleic acid sequence.

The target polynucleotide sequence may be any region of the polynucleotide (e.g., DNA sequence) suitable for epigenome editing. In aspects, the target polynucleotide sequence is part of a gene. In aspects, the target polynucleotide sequence is part of a transcriptional regulatory sequence. In aspects, the target polynucleotide sequence is part of a promoter, enhancer or silencer. In aspects, the target polynucleotide sequence is part of a promoter. In aspects, the target polynucleotide sequence is part of an enhancer. In aspects, the target polynucleotide sequence is part of a silencer.

In embodiments, the target polynucleotide sequence is a hypomethylated nucleic acid sequence. A "hypomethylated nucleic acid sequence" is used herein according to the standard meaning in the art and refers to a loss or lack of methyl groups on the 5-methylcytosine nucleotide (e.g., in CpG). The loss or lack of methyl groups may be relative to a standard control. Hypomethylation may occur, for example, in aging cells or in cancer (e.g., early stages of neoplasia) relative to the younger cell or non-cancer cell, respectively. Thus, the complex may be useful for reestablishing normal (e.g. non-aged of non-diseased) methylation levels.

In embodiments, the target polynucleotide sequence is within about 3000 base pairs (bp) flanking a transcription start site. In aspects, the target polynucleotide sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking a transcription start site.

In embodiments, the target polynucleotide sequence is at, near, or within a promoter sequence. In aspects, the target polynucleotide sequence is within a CpG island. In aspects, the target polynucleotide sequence is known to be associated with a disease or condition characterized by DNA hypomethylation.

In embodiments, exemplary target polynucleotide sequences include those described in Tables 1 and 2. In aspects, the target polynucleotide sequence include the sequence of SEQ ID NO:37, 39, 41, 43, 45, 47, 49, 51, 53, 55, 57, 59, 61, 63, 65, 67, 69, 71, 73, 75, 77, 79, 81, 83, 85, 87, 89, 91, 93, or 95. In aspects, the target polynucleotide sequence include an amino acid sequence having at least 80%, 85%, 90%, 91%, 92%, 93%, 94%, 95%, 96%, 97%, 98%, or 99% sequence identity to SEQ ID NO:37, 39, 41, 43, 45, 47, 49, 51, 53, 55, 57, 59, 61, 63, 65, 67, 69, 71, 73, 75, 77, 79, 81, 83, 85, 87, 89, 91, 93, or 95. In aspects, the target polynucleotide sequence is SEQ ID NO:37. In aspects, the target polynucleotide sequence is SEQ ID NO:39. In aspects, the target polynucleotide sequence is SEQ ID NO:41. In aspects, the target polynucleotide sequence is SEQ ID NO:43. In aspects, the target polynucleotide sequence is SEQ ID NO:45. In aspects, the target polynucleotide sequence is SEQ ID NO:47. In aspects, the target polynucleotide sequence is SEQ ID NO:49. In aspects, the target polynucleotide sequence is SEQ ID NO:51. In aspects, the target polynucleotide sequence is SEQ ID NO:53. In aspects, the target polynucleotide sequence is SEQ ID NO:55. In aspects, the target polynucleotide sequence is SEQ ID NO:57. In aspects, the target polynucleotide sequence is SEQ ID NO:59. In aspects, the target polynucleotide sequence is SEQ ID NO:61. In aspects, the target polynucleotide sequence is SEQ ID NO:63. In aspects, the target polynucleotide sequence is SEQ ID NO:65. In aspects, the target polynucleotide sequence is SEQ ID NO:67. In aspects, the target polynucleotide sequence is SEQ ID NO:69. In aspects, the target polynucleotide sequence is SEQ ID NO:71. In aspects, the target polynucleotide sequence is SEQ ID NO:73. In aspects, the target polynucleotide sequence is SEQ ID NO:75. In aspects, the target polynucleotide sequence is SEQ ID NO:77. In aspects, the target polynucleotide sequence is SEQ ID NO:79. In aspects, the target polynucleotide sequence is SEQ ID NO:81. In aspects, the target polynucleotide sequence is SEQ ID NO:83. In aspects, the target polynucleotide sequence is SEQ ID NO:85. In aspects, the target polynucleotide sequence is SEQ ID NO:87. In aspects, the target polynucleotide sequence is SEQ ID NO:89. In aspects, the target polynucleotide sequence is SEQ ID NO:91. In aspects, the target polynucleotide sequence is SEQ ID NO:93. In aspects, the target polynucleotide sequence is SEQ ID NO:95.

In aspects, the target polynucleotide sequence has at least 75%, 80%, 85%, 90%, 91%, 92%, 93%, 94%, 95%, 96%, 97%, 98%, or 99% sequence identity to SEQ ID NO:37. In aspects, the target polynucleotide sequence has at least 75%, 80%, 85%, 90%, 91%, 92%, 93%, 94%, 95%, 96%, 97%, 98%, or 99% sequence identity to SEQ ID NO:39. In aspects, the target polynucleotide sequence has at least 75%, 80%, 85%, 90%, 91%, 92%, 93%, 94%, 95%, 96%, 97%, 98%, or 99% sequence identity to SEQ ID NO:41. In aspects, the target polynucleotide sequence has at least 75%, 80%, 85%, 90%, 91%, 92%, 93%, 94%, 95%, 96%, 97%, 98%, or 99% sequence identity to SEQ ID NO:43. In aspects, the target polynucleotide sequence is SEQ ID NO:45. In aspects, the target polynucleotide sequence has at least 75%, 80%, 85%, 90%, 91%, 92%, 93%, 94%, 95%, 96%, 97%, 98%, or 99% sequence identity to SEQ ID NO:47. In aspects, the target polynucleotide sequence has at least 75%, 80%, 85%, 90%, 91%, 92%, 93%, 94%, 95%, 96%, 97%, 98%, or 99% sequence identity to SEQ ID NO:49. In aspects, the target polynucleotide sequence has at least 75%, 80%, 85%, 90%, 91%, 92%, 93%, 94%, 95%, 96%, 97%, 98%, or 99% sequence identity to SEQ ID NO:51. In aspects, the target polynucleotide sequence has at least 75%, 80%, 85%, 90%, 91%, 92%, 93%, 94%, 95%, 96%, 97%, 98%, or 99% sequence identity to SEQ ID NO:53. In aspects, the target polynucleotide sequence has at least 75%, 80%, 85%, 90%, 91%, 92%, 93%, 94%, 95%, 96%, 97%, 98%, or 99% sequence identity to SEQ ID NO:55. In aspects, the target polynucleotide sequence has at least 75%, 80%, 85%, 90%, 91%, 92%, 93%, 94%, 95%, 96%, 97%, 98%, or 99% sequence identity to SEQ ID NO:57. In aspects, the target polynucleotide sequence has at least 75%, 80%, 85%, 90%, 91%, 92%, 93%, 94%, 95%, 96%, 97%, 98%, or 99% sequence identity to SEQ ID NO:59. In aspects, the target polynucleotide sequence has at least 75%, 80%, 85%, 90%, 91%, 92%, 93%, 94%, 95%, 96%, 97%, 98%, or 99% sequence identity to SEQ ID NO:61. In aspects, the target polynucleotide sequence has at least 75%, 80%, 85%, 90%, 91%, 92%, 93%, 94%, 95%, 96%, 97%, 98%, or 99% sequence identity to SEQ ID NO:63. In aspects, the target polynucleotide sequence has at least 75%, 80%, 85%, 90%, 91%, 92%, 93%, 94%, 95%, 96%, 97%, 98%, or 99% sequence identity to SEQ ID NO:65. In aspects, the target polynucleotide sequence has at least 75%, 80%, 85%, 90%, 91%, 92%, 93%, 94%, 95%, 96%, 97%, 98%, or 99%, sequence identity to SEQ ID NO:67. In aspects, the target polynucleotide sequence has at least 75%, 80%, 85%, 90%, 91%, 92%, 93%, 94%, 95%, 96%, 97%, 98%, or 99% sequence identity to SEQ ID NO:69. In aspects, the target polynucleotide sequence has at least 75%, 80%, 85%, 90%, 91%, 92%, 93%, 94%, 95%, 96%, 97%, 98%, or 99% sequence identity to SEQ ID NO:71. In aspects, the target polynucleotide sequence has at least 75%, 80%, 85%, 90%, 91%, 92%, 93%, 94%, 95%, 96%, 97%, 98%, or 99% sequence identity to SEQ ID NO:73. In aspects, the target polynucleotide sequence has at least 75%, 80%, 85%, 90%, 91%, 92%, 93%, 94%, 95%, 96%, 97%, 98%, or 99% sequence identity to SEQ ID NO:75. In aspects, the target polynucleotide sequence has at least 75%, 80%, 85%, 90%, 91%, 92%, 93%, 94%, 95%, 96%, 97%, 98%, or 99% sequence identity to SEQ ID NO:77. In aspects, the target polynucleotide sequence has at least 75%, 80%, 85%, 90%, 91%, 92%, 93%, 94%, 95%, 96%, 97%, 98%, or 99% sequence identity to SEQ ID NO:79. In aspects, the target polynucleotide sequence has at least 75%, 80%, 85%, 90%, 91%, 92%, 93%, 94%, 95%, 96%, 97%, 98%, or 99% sequence identity to SEQ ID NO:81. In aspects, the target polynucleotide sequence has at least 75%, 80%, 85%, 90%, 91%, 92%, 93%, 94%, 95%, 96%, 97%, 98%, or 99% sequence identity to SEQ ID NO:83. In aspects, the target polynucleotide sequence has at least 75%, 80%, 85%, 90%, 91%, 92%, 93%, 94%, 95%, 96%, 97%, 98%, or 99%, sequence identity to SEQ ID NO:85. In aspects, the target polynucleotide sequence has at least 75%, 80%, 85%, 90%, 91%, 92%, 93%, 94%, 95%, 96%, 97%, 98%, or 99% sequence identity to SEQ ID NO:87. In aspects, the target polynucleotide sequence has at least 75%, 80%, 85%, 90%, 91%, 92%, 93%, 94%, 95%, 96%, 97%, 98%, or 99% sequence identity to SEQ ID NO:89. In aspects, the target polynucleotide sequence has at least 75%, 80%, 85%, 90%, 91%, 92%, 93%, 94%, 95%, 96%, 97%, 98%, or 99% sequence identity to SEQ ID NO:91. In aspects, the target polynucleotide sequence has at least 75%, 80%, 85%, 90%, 91%, 92%, 93%, 94%, 95%, 96%, 97%, 98%, or 99% sequence identity to SEQ ID NO:93. In aspects, the target polynucleotide sequence has at least 75%, 80%, 85%, 90%, 91%, 92%, 93%, 94%, 95%, 96%, 97%, 98%, or 99% sequence identity to SEQ ID NO:95.

In aspects, the target polynucleotide sequence has at least 90% sequence identity to SEQ ID NO:37. In aspects, the target polynucleotide sequence has at least 90% sequence identity to SEQ ID NO:39. In aspects, the target polynucleotide sequence has at least 90% sequence identity to SEQ ID NO:41. In aspects, the target polynucleotide sequence has at least 90% sequence identity to SEQ ID NO:43. In aspects, the target polynucleotide sequence is SEQ ID NO:45. In aspects, the target polynucleotide sequence has at least 90% sequence identity to SEQ ID NO:47. In aspects, the target polynucleotide sequence has at least 90% sequence identity to SEQ ID NO:49. In aspects, the target polynucleotide sequence has at least 90% sequence identity to SEQ ID NO:51. In aspects, the target polynucleotide sequence has at least 90% sequence identity to SEQ ID NO:53. In aspects, the target polynucleotide sequence has at least 90% sequence identity to SEQ ID NO:55. In aspects, the target polynucleotide sequence has at least 90% sequence identity to SEQ ID NO:57. In aspects, the target polynucleotide sequence has at least 90% sequence identity to SEQ ID NO:59. In aspects, the target polynucleotide sequence has at least 90% sequence identity to SEQ ID NO:61. In aspects, the target polynucleotide sequence has at least 90% sequence identity to SEQ ID NO:63. In aspects, the target polynucleotide sequence has at least 90% sequence identity to SEQ ID NO:65. In aspects, the target polynucleotide sequence has at least 90% sequence identity to SEQ ID NO:67. In aspects, the target polynucleotide sequence has at least 90% sequence identity to SEQ ID NO:69. In aspects, the target polynucleotide sequence has at least 90% sequence identity to SEQ ID NO:71. In aspects, the target polynucleotide sequence has at least 90% sequence identity to SEQ ID NO:73. In aspects, the target polynucleotide sequence has at least 90% sequence identity to SEQ ID NO:75. In aspects, the target polynucleotide sequence has at least 90% sequence identity to SEQ ID NO:77. In aspects, the target polynucleotide sequence has at least 90% sequence identity to SEQ ID NO:79. In aspects, the target polynucleotide sequence has at least 90% sequence identity to SEQ ID NO:81. In aspects, the target polynucleotide sequence has at least 90% sequence identity to SEQ ID NO:83. In aspects, the target polynucleotide sequence has at least 90% sequence identity to SEQ ID NO:85. In aspects, the target polynucleotide sequence has at least 90% sequence identity to SEQ ID NO:87. In aspects, the target polynucleotide sequence has at least 90% sequence identity to SEQ ID NO:89. In aspects, the target polynucleotide sequence has at least 90% sequence identity to SEQ ID NO:91. In aspects, the target polynucleotide sequence has at least 90% sequence identity to SEQ ID NO:93. In aspects, the target polynucleotide sequence has at least 90% sequence identity to SEQ ID NO:95.

In aspects, the target polynucleotide sequence has at least 95% sequence identity to SEQ ID NO:37. In aspects, the target polynucleotide sequence has at least 95% sequence identity to SEQ ID NO:39. In aspects, the target polynucleotide sequence has at least 95% sequence identity to SEQ ID NO:41. In aspects, the target polynucleotide sequence has at least 95% sequence identity to SEQ ID NO:43. In aspects, the target polynucleotide sequence is SEQ ID NO:45. In aspects, the target polynucleotide sequence has at least 95% sequence identity to SEQ ID NO:47. In aspects, the target polynucleotide sequence has at least 95% sequence identity to SEQ ID NO:49. In aspects, the target polynucleotide sequence has at least 95% sequence identity to SEQ ID NO:51. In aspects, the target polynucleotide sequence has at least 95% sequence identity to SEQ ID NO:53. In aspects, the target polynucleotide sequence has at least 95% sequence identity to SEQ ID NO:55. In aspects, the target polynucleotide sequence has at least 95% sequence identity to SEQ ID NO:57. In aspects, the target polynucleotide sequence has at least 95% sequence identity to SEQ ID NO:59. In aspects, the target polynucleotide sequence has at least 95% sequence identity to SEQ ID NO:61. In aspects, the target polynucleotide sequence has at least 95% sequence identity to SEQ ID NO:63. In aspects, the target polynucleotide sequence has at least 95% sequence identity to SEQ ID NO:65. In aspects, the target polynucleotide sequence has at least 95% sequence identity to SEQ ID NO:67. In aspects, the target polynucleotide sequence has at least 95% sequence identity to SEQ ID NO:69. In aspects, the target polynucleotide sequence has at least 95% sequence identity to SEQ ID NO:71. In aspects, the target polynucleotide sequence has at least 95% sequence identity to SEQ ID NO:73. In aspects, the target polynucleotide sequence has at least 95% sequence identity to SEQ ID NO:75. In aspects, the target polynucleotide sequence has at least 95% sequence identity to SEQ ID NO:77. In aspects, the target polynucleotide sequence has at least 95% sequence identity to SEQ ID NO:79. In aspects, the target polynucleotide sequence has at least 95% sequence identity to SEQ ID NO:81. In aspects, the target polynucleotide sequence has at least 95% sequence identity to SEQ ID NO:83. In aspects, the target polynucleotide sequence has at least 95% sequence identity to SEQ ID NO:85. In aspects, the target polynucleotide sequence has at least 95% sequence identity to SEQ ID NO:87. In aspects, the target polynucleotide sequence has at least 95% sequence identity to SEQ ID NO:89. In aspects, the target polynucleotide sequence has at least 95% sequence identity to SEQ ID NO:91. In aspects, the target polynucleotide sequence has at least 95% sequence identity to SEQ ID NO:93. In aspects, the target polynucleotide sequence has at least 95% sequence identity to SEQ ID NO:95.

In embodiments, the complex includes dCas9 bound to the polynucleotide through binding a binding sequence of the polynucleotide and thereby forming a ribonucleoprotein complex. In aspects, the binding sequence forms a hairpin structure. In aspects, the binding sequence is 30-100 nt, 35-50 nt, 37-47 nt, or 42 nt in length.

In embodiments, the binding sequence (e.g., Cas9-binding sequence) interacts with or binds to a Cas9 protein (e.g., dCas9 protein), and together they bind to the target polynucleotide sequence recognized by the DNA-targeting sequence. The binding sequence (e.g., Cas9-binding sequence) includes two complementary stretches of nucleotides that hybridize to one another to form a double stranded RNA duplex (a dsRNA duplex). These two complementary stretches of nucleotides may be covalently linked by intervening nucleotides known as linkers or linker nucleotides (e.g., in the case of a single-molecule polynucleotide), and hybridize to form the double stranded RNA duplex (dsRNA duplex, or "Cas9-binding hairpin") of the binding sequence (e.g., Cas9-binding sequence), thus resulting in a stem-loop structure. Alternatively, in some aspects, the two complementary stretches of nucleotides may not be covalently linked, but instead are held together by hybridization between complementary sequences (e.g., a two-molecule polynucleotide).

The binding sequence (e.g., Cas9-binding sequence) can have a length of from 10 nucleotides to 100 nucleotides, e.g., from 10 nucleotides (nt) to 20 nt, from 20 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In aspects, the binding sequence has a length of from 15 nucleotides (nt) to 80 nt. In aspects, the binding sequence has a length of from 15 nt to 50 nt. In aspects, the binding sequence has a length of from 15 nt to 40 nt. In aspects, the binding sequence has a length of from 15 nt to 30 nt. In aspects, the binding sequence has a length of from 37 nt to 47 nt (e.g., 42 nt). In aspects, the binding sequence has a length of from 15 nt to 25 nt.

The dsRNA duplex of the binding sequence (e.g., Cas9-binding sequence) can have a length from 6 base pairs (bp) to 50 bp. For example, the dsRNA duplex of the binding sequence (e.g., Cas9-binding sequence) can have a length from 6 bp to 40 bp, from 6 bp to 30 bp, from 6 bp to 25 bp, from 6 bp to 20 bp, from 6 bp to 15 bp, from 8 bp to 40 bp, from 8 bp to 30 bp, from 8 bp to 25 bp, from 8 bp to 20 bp or from 8 bp to 15 bp. In aspects, the dsRNA duplex of the binding sequence (e.g., Cas9-binding sequence) has a length from 8 bp to 10 bp. In aspects, the dsRNA duplex of the binding sequence (e.g., Cas9-binding sequence) has a length from 10 bp to 15 bp. In aspects, the dsRNA duplex of the binding sequence (e.g., Cas9-binding sequence) has a length from 15 bp to 18 bp. In aspects, the dsRNA duplex of the binding sequence (e.g., Cas9-binding sequence) has a length from 18 bp to 20 bp. In aspects, the dsRNA duplex of the binding sequence (e.g., Cas9-binding sequence) has a length from 20 bp to 25 bp. In aspects, the dsRNA duplex of the binding sequence (e.g., Cas9-binding sequence) has a length from 25 bp to 30 bp. In aspects, the dsRNA duplex of the binding sequence (e.g., Cas9-binding sequence) has a length from 30 bp to 35 bp. In aspects, the dsRNA duplex of the binding sequence (e.g., Cas9-binding sequence) has a length from 35 bp to 40 bp. In aspects, the dsRNA duplex of the binding sequence (e.g., Cas9-binding sequence) has a length from 40 bp to 50 bp.

In embodiments, the exemplary polynucleotide that forms a complex with a fusion protein described herein includes those described in Tables 1 and 2 as sgRNA. In aspects, the polynucleotide that forms a complex with a fusion protein described herein includes the sequence of SEQ ID NO: 38, 40, 42, 44, 46, 48, 50, 52, 54, 56, 58, 60, 62, 64, 66, 68, 70, 72, 74, 76, 78, 80, 82, 84, 86, 88, 90, 92, or 94 or their corresponding RNA sequence. In aspects, the polynucleotide that forms a complex with a fusion protein described herein includes the sequence having at least 80%, 85%, 90%, 91%, 92%, 93%, 94%, 95%, 96%, 97%, 98%, or 99% sequence identity to SEQ ID NO:38, 40, 42, 44, 46, 48, 50, 52, 54, 56, 58, 60, 62, 64, 66, 68, 70, 72, 74, 76, 78, 80, 82, 84, 86, 88, 90, 92, or 94 or their corresponding RNA sequence. In aspects, the polynucleotide that forms a complex with a fusion protein described herein includes the sequence of SEQ ID NO:38. In aspects, the polynucleotide that forms a complex with a fusion protein described herein includes the sequence of SEQ ID NO:40. In aspects, the polynucleotide that forms a complex with a fusion protein described herein includes the sequence of SEQ ID NO:42. In aspects, the polynucleotide that forms a complex with a fusion protein described herein includes the sequence of SEQ ID NO:44. In aspects, the polynucleotide that forms a complex with a fusion protein described herein includes the sequence of SEQ ID NO:46. In aspects, the polynucleotide that forms a complex with a fusion protein described herein includes the sequence of SEQ ID NO:48. In aspects, the polynucleotide that forms a complex with a fusion protein described herein includes the sequence of SEQ ID NO:50. In aspects, the polynucleotide that forms a complex with a fusion protein described herein includes the sequence of SEQ ID NO:52. In aspects, the polynucleotide that forms a complex with a fusion protein described herein includes the sequence of SEQ ID NO:54. In aspects, the polynucleotide that forms a complex with a fusion protein described herein includes the sequence of SEQ ID NO:56. In aspects, the polynucleotide that forms a complex with a fusion protein described herein includes the sequence of SEQ ID NO:58. In aspects, the polynucleotide that forms a complex with a fusion protein described herein includes the sequence of SEQ ID NO:60. In aspects, the polynucleotide that forms a complex with a fusion protein described herein includes the sequence of SEQ ID NO:62. In aspects, the polynucleotide that forms a complex with a fusion protein described herein includes the sequence of SEQ ID NO:64. In aspects, the polynucleotide that forms a complex with a fusion protein described herein includes the sequence of SEQ ID NO:66. In aspects, the polynucleotide that forms a complex with a fusion protein described herein includes the sequence of SEQ ID NO:68. In aspects, the polynucleotide that forms a complex with a fusion protein described herein includes the sequence of SEQ ID NO:70. In aspects, the polynucleotide that forms a complex with a fusion protein described herein includes the sequence of SEQ ID NO:72. In aspects, the polynucleotide that forms a complex with a fusion protein described herein includes the sequence of SEQ ID NO:74. In aspects, the polynucleotide that forms a complex with a fusion protein described herein includes the sequence of SEQ ID NO:76. In aspects, the polynucleotide that forms a complex with a fusion protein described herein includes the sequence of SEQ ID NO:78. In aspects, the polynucleotide that forms a complex with a fusion protein described herein includes the sequence of SEQ ID NO:80. In aspects, the polynucleotide that forms a complex with a fusion protein described herein includes the sequence of SEQ ID NO:82. In aspects, the polynucleotide that forms a complex with a fusion protein described herein includes the sequence of SEQ ID NO:84. In aspects, the polynucleotide that forms a complex with a fusion protein described herein includes the sequence of SEQ ID NO:86. In aspects, the polynucleotide that forms a complex with a fusion protein described herein includes the sequence of SEQ ID NO:88. In aspects, the polynucleotide that forms a complex with a fusion protein described herein includes the sequence of SEQ ID NO:90. In aspects, the polynucleotide that forms a complex with a fusion protein described herein includes the sequence of SEQ ID NO:92. In aspects, the polynucleotide that forms a complex with a fusion protein described herein includes the sequence of SEQ ID NO:94.

Nucleic Acids and Vectors

The fusion protein described herein, including embodiments and aspects thereof, may be provided as a nucleic acid sequence that encodes for the fusion protein. Thus, in an aspect is provided a nucleic acid sequence encoding the fusion protein described herein, including embodiments and aspects thereof. In an aspect is provided a nucleic acid sequence encoding the fusion protein described herein (including the DNA-targeting sequence), including embodiments and aspects thereof. In aspects, the nucleic acid sequence encodes for a fusion protein described herein, including fusion proteins having amino acid sequences with certain % sequence identities described herein. In aspects, the nucleic acid is RNA. In aspects, the nucleic acid is messenger RNA. In aspects, the messenger RNA is messenger RNP. In aspects, the nucleic acid sequence encodes for the fusion proteins described herein, including embodiments and aspects thereof. In aspects, the nucleic acid sequence encodes for the fusion protein of SEQ ID NO:1. In aspects, the nucleic acid sequence encodes for the fusion protein of SEQ ID NO:2. In aspects, the nucleic acid sequence encodes for the fusion protein of SEQ ID NO:3. In aspects, the nucleic acid sequence encodes for the fusion protein of SEQ ID NO:4. In aspects, the nucleic acid sequence encodes for the fusion protein of SEQ ID NO:5. In aspects, the nucleic acid sequence encodes for the fusion protein of SEQ ID NO:6. In aspects, the nucleic acid sequence encodes for the fusion protein of SEQ ID NO:7. In aspects, the nucleic acid sequence encodes for the fusion protein of SEQ ID NO:8. In aspects, the nucleic acid sequence encodes for the fusion protein of SEQ ID NO:9. In aspects, the nucleic acid sequence encodes for the fusion protein of SEQ ID NO:10. In aspects, the nucleic acid sequence encodes for the fusion protein of SEQ ID NO:11. In aspects, the nucleic acid sequence encodes for the fusion protein of SEQ ID NO:12. In aspects, the nucleic acid sequence encodes for the fusion protein of SEQ ID NO:13. In aspects, the nucleic acid sequence encodes for the fusion protein of SEQ ID NO:14. In aspects, the nucleic acid sequence encodes for the fusion protein of SEQ ID NO:15.

It is further contemplated that the nucleic acid sequence encoding the fusion protein as described herein, including embodiments and aspects thereof, may be included in a vector. Therefore, in an aspect is provided a vector including a nucleic acid sequence as described herein, including embodiments and aspects thereof. In aspects, the vector comprises a nucleic acid sequence that encodes for a fusion protein described herein, including fusion proteins having amino acid sequences with certain % sequence identities described herein. In aspects, the nucleic acid is messenger RNA. In aspects, the messenger RNA is messenger RNP. In aspects, the vector comprises a nucleic acid sequence that encodes for the fusion protein of SEQ ID NO:1. In aspects, the vector comprises a nucleic acid sequence that encodes for the fusion protein of SEQ ID NO:2. In aspects, the vector comprises a nucleic acid sequence that encodes for the fusion protein of SEQ ID NO:3. In aspects, the vector comprises a nucleic acid sequence that encodes for the fusion protein of SEQ ID NO:4. In aspects, the vector comprises a nucleic acid sequence that encodes for the fusion protein of SEQ ID NO:5. In aspects, the vector comprises a nucleic acid sequence that encodes for the fusion protein of SEQ ID NO:6. In aspects, the vector comprises a nucleic acid sequence that encodes for the fusion protein of SEQ ID NO:7. In aspects, the vector comprises a nucleic acid sequence that encodes for the fusion protein of SEQ ID NO:8. In aspects, the vector comprises a nucleic acid sequence that encodes for the fusion protein of SEQ ID NO:9. In aspects, the vector comprises a nucleic acid sequence that encodes for the fusion protein of SEQ ID NO:10. In aspects, the vector comprises a nucleic acid sequence that encodes for the fusion protein of SEQ ID NO:11. In aspects, the vector comprises a nucleic acid sequence that encodes for the fusion protein of SEQ ID NO:12. In aspects, the vector comprises a nucleic acid sequence that encodes for the fusion protein of SEQ ID NO:13. In aspects, the vector comprises a nucleic acid sequence that encodes for the fusion protein of SEQ ID NO:14. In aspects, the vector comprises a nucleic acid sequence that encodes for the fusion protein of SEQ ID NO:15.

In embodiments, the vector further includes a polynucleotide, wherein the polynucleotide includes: (1) a DNA-targeting sequence that is complementary to a target polynucleotide sequence; and (2) a binding sequence for the nuclease-deficient RNA-guided DNA endonuclease enzyme. Thus, one or more vectors may include all necessary components for preforming epigenome editing.

Cells

The compositions described herein may be incorporated into a cell. Inside the cell, the compositions as described herein, including embodiments and aspects thereof, may perform epigenome editing. Accordingly, in an aspect is provided a cell including a fusion protein as described herein, including embodiments and aspects thereof, a nucleic acid as described herein, including embodiments and aspects thereof, a complex as described herein, including embodiments and aspects thereof, or a vector as described herein, including embodiments and aspects thereof. In aspects is provided a cell including a fusion protein as described herein, including embodiments and aspects thereof. In aspects is provided a cell including a nucleic acid as described herein, including embodiments and aspects thereof. In aspects is provided a cell including a complex as described herein, including embodiments and aspects thereof. In aspects is provided a cell including a vector as described herein, including embodiments and aspects thereof. In aspects, the cell is a eukaryotic cell. In aspects, the cell is a mammalian cell.

Methods

It is contemplated that the compositions described herein may be used for epigenome editing, and more particularly epigenome editing resulting in the repression or silencing of target nucleic acid sequences (e.g., genes). Without intending to be bound by any theory, silencing may result from methylation of and/or the introduction of repressive chromatin markers (e.g., mono-, di-, or tri-methylation of specific histones (e.g., H3K9, H3K27), deacetylation, acetylation, phosphorylation, ubiquitination) on chromatin containing a target nucleic acid sequence. Without intending to be bound by any theory, the method can be used to change epigenetic state by, for example, closing chromatin via methylation or introducing repressive chromatin markers on chromatin containing the target nuclei acid sequence (e.g., gene). Without intending to be bound by any theory, it is contemplated that the Dnmt3A-3L fusion functions to add methyl marks at CG DNA sites found in CpG islands and the KRAB domain recruits epigenetic factors that modify the histones by introducing repressive marks. Without intending to be bound by any theory, DNA is methylated at the C nucleotide of CG sequences found in CpG islands (i.e., adding methyl marks at the C nucleotide of CG DNA sites found in CpG islands).

In an aspect is provided a method of silencing a target nucleic acid sequence in a cell, including delivering a first polynucleotide encoding a fusion protein as described herein, including embodiments and aspects thereof, to a cell containing the target nucleic acid; and delivering to the cell a second polynucleotide including: (i) a DNA-targeting sequence that is complementary to the target nucleic acid sequence; and (ii) a binding sequence for the nuclease-deficient RNA-guide DNA endonuclease enzyme. Without intending to be bound by any theory, the fusion protein silences the target nucleic acid sequence in the cell by methylating a chromatin containing the target nucleic acid sequence and/or by introducing repressive chromatin marks to a chromatin containing the target nucleic acid sequence. Without intending to be bound by any theory, methylating a chromatin means that DNA is methylated at the C nucleotide of CG sequences found in CpG islands (i.e., adding methyl marks at the C nucleotide of CG DNA sites found in CpG islands). In aspects, the sequence that is within about 3000 base pairs of the target nucleic acid sequence is is methylated. In aspects, the sequence that is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs of the target nucleic acid sequence is methylated.

The term "repressive chromatin markers" as used herein refers to modifications made to the chromatin that result in silencing (e.g., decreasing or inhibiting of transcription) of the target nucleic acid sequence (e.g., a gene). Examples of repressive chromatin markers include, but are not limited to, mono-, di-, and/or tri-methylation, acetylation/deacetylation, phosphorylation, and ubiquitination of histones (e.g., H3K9, H3K27, H3K79, H2BK5).

In embodiments, silencing refers to a complete suppression of transcription. In aspects, silencing refers to a significant decrease in transcription compared to control levels of transcription.

In embodiments, the first polynucleotide is contained within a first vector. In aspects, the first polynucleotide is contained within a second vector. In aspects, the first vector and the second vector are the same. In aspects, the first vector is different from the second vector.

In embodiments, the polynucleotide described herein is delivered into the cell by any method known in the art, for example, by transfection, electroporation or transduction.

Alternatively, in an aspect is provided a method of silencing a target nucleic acid sequence in a cell, including delivering a complex as described herein, including embodiments and aspects thereof, to a cell containing the target nucleic acid. Without intending to be bound by any theory, the complex silences the target nucleic acid sequence in the cell by methylating a chromatin containing the target nucleic acid sequence and/or by introducing repressive chromatin marks to a chromatin containing the target nucleic acid sequence.

In embodiments, the cell is a mammalian cell.

In embodiments, the method has a specificity that is 2-fold higher than a specificity to a non-target nucleic acid sequence. In aspects, the method has a specificity that is at least 2-fold (e.g., 2-, 3-, 4-, 5-, 6-, 7-, 8-, 9-, 10-, 15-, 20-, 25-fold) higher than a specificity to a non-target nucleic acid sequence. Methods for determining specificity are well known in the art and include, but are not limited to, RNA-seq, bisulfite sequencing, chromatin immunoprecipitation, flow cytometry, and qPCR. Thus, in aspects, specificity is determined by RNA-seq. In aspects, specificity is determined by bisulfite sequencing. In aspects, specificity is determined by chromatin immunoprecipitation. In aspects, specificity is determined by flow cytometry. In aspects, specificity is determined by qPCR.

In aspects, the complex is delivered into the cell via any methods known in the art, for example, via ribonucleoprotein (RNP) delivery.

Embodiments N1-N41

Embodiment N1. A fusion protein comprising a nuclease-deficient RNA-guided DNA endonuclease enzyme, a Krüppel associated box domain, and a DNA methyltransferase domain.

Embodiment N2. The fusion protein of Embodiment N1, wherein the nuclease-deficient RNA-guided DNA endonuclease enzyme is dCas9, ddCpf1, a nuclease-deficient Cas9 variant, or a nuclease-deficient Class II CRISPR endonuclease.

Embodiment N3. The fusion protein of Embodiment N1 or N2, wherein the DNA methyltransferase domain is a Dnmt3A-3L domain.

Embodiment N4. The fusion protein of Embodiment N1, wherein the fusion protein comprises, from N-terminus to C-terminus, the DNA methyltransferase domain, the nuclease-deficient RNA-guided DNA endonuclease enzyme, and the Krüppel associated box domain Embodiment N5. The fusion protein of Embodiment N4, wherein the nuclease-deficient RNA-guided DNA endonuclease enzyme is dCas9 and the DNA methyltransferase domain is a Dnmt3A-3L domain Embodiment N6. The fusion protein of Embodiment N5, wherein the nuclease-deficient RNA-guided DNA endonuclease enzyme is dCas9 and the DNA methyltransferase domain is a Dnmt3A-3L domain Embodiment N7. The fusion protein of Embodiment N6, wherein the peptide linker is a XTEN linker.

Embodiment N8. The fusion protein of Embodiment N1, wherein the fusion protein comprises, from N-terminus to C-terminus, the Krüppel associated box, the nuclease-deficient RNA-guided DNA endonuclease enzyme, and the DNA methyltransferase domain Embodiment N9. The fusion protein of Embodiment N8, wherein the nuclease-deficient RNA-guided DNA endonuclease enzyme is dCas9 and the DNA methyltransferase domain is a Dnmt3A-3L domain.

Embodiment N10. The fusion protein of Embodiment N9, wherein the dCas9 is covalently linked to the Dnmt3A-3L domain via a peptide linker and wherein the Krüppel associated box domain is covalently linked to the dCas9 via a peptide linker.

Embodiment N11. The fusion protein of Embodiment N10, wherein the peptide linker is a XTEN linker.

Embodiment N12. The fusion protein of any one of Embodiments N1 to N3, wherein the nuclease-deficient RNA-guided DNA endonuclease enzyme is covalently linked to the Krüppel associated box domain via a peptide linker.

Embodiment N13. The fusion protein of any one of Embodiments N1 to N3, wherein the nuclease-deficient RNA-guided DNA endonuclease enzyme is covalently linked to the DNA methyltransferase domain via a peptide linker.

Embodiment N14. The fusion protein of any one of Embodiments N1 to N3, wherein the Krüppel associated box domain is covalently linked to the DNA methyltransferase domain via a peptide linker.

Embodiment N15. The fusion protein of any one of Embodiments N12 to N14, wherein the peptide linker is a XTEN linker.

Embodiment N16. The fusion protein of Embodiment N15, wherein the XTEN linker comprises about 16 to 80 amino acid residues.

Embodiment N17. The fusion protein of any one of Embodiments N1 to N16, further comprising a nuclear localization signal peptide.

Embodiment N18. The fusion protein of Embodiment N1, wherein the fusion protein comprises the amino acid sequence of SEQ ID NO: 1, 2, 3, 4, 5, 6, 7, 8, 9, 10, 11 12, 13, 14, or 15.

Embodiment N19. A nucleic acid sequence encoding the fusion protein of any one of Embodiments N1 to N18.

Embodiment N20. The nucleic acid sequence of Embodiment N19, wherein the nucleic acid sequence is messenger RNA.

Embodiment N21. A complex comprising: (i) a fusion protein of any one of Embodiments N1 to N18; and (ii) a polynucleotide comprising: (a) a DNA-targeting sequence that is complementary to a target polynucleotide sequence; and (b) a binding sequence for the nuclease-deficient RNA-guided DNA endonuclease enzyme, wherein the nuclease-deficient RNA-guided DNA endonuclease enzyme is bound to the polynucleotide via the binding sequence.

Embodiment N22. The complex of Embodiment N21, wherein the target polynucleotide sequence is part of a gene.

Embodiment N23. The complex of Embodiment N21, wherein the target polynucleotide sequence is part of a transcriptional regulatory sequence.

Embodiment N24. The complex of Embodiment N21, wherein the target polynucleotide sequence is part of a promoter, enhancer, or silencer.

Embodiment N25. The complex of Embodiment N21, wherein the target polynucleotide sequence is within about 3000 bp flanking a transcription start site.

Embodiment N26. A vector comprising the nucleic acid sequence of Embodiment N19 or N20.

Embodiment N27. The vector of Embodiment N26, further comprising a polynucleotide, wherein the polynucleotide comprises: (a) a DNA-targeting sequence that is complementary to a target polynucleotide sequence; and (b) a binding sequence for the nuclease-deficient RNA-guided DNA endonuclease enzyme.

Embodiment N28. A cell comprising the fusion protein of any one of Embodiments N1 to N18; the nucleic acid of Embodiment N19 or N20; the complex of any one of Embodiments N21 to N25, or the vector of Embodiment N26 or N27.

Embodiment N29. The cell of Embodiment N28, wherein the cell is a eukaryotic cell.

Embodiment N30. The cell of Embodiment N28, wherein the cell is a mammalian cell.

Embodiment N31. A method of silencing a target nucleic acid sequence in a cell, comprising: (i) delivering a first polynucleotide encoding a fusion protein of any one of Embodiments N1 to N18 to a cell containing the target nucleic acid; and (ii) delivering to the cell a second polynucleotide comprising: (a) a DNA-targeting sequence that is complementary to the target nucleic acid sequence; and (b) a binding sequence for the nuclease-deficient RNA-guide DNA endonuclease enzyme Embodiment N32. The method of Embodiment N31, wherein the fusion protein silences the target nucleic acid sequence in the cell by methylating a chromatin containing the target nucleic acid sequence and/or by introducing repressive chromatin marks to a chromatin containing the target nucleic acid sequence.

Embodiment N33. The method of Embodiment N31 or N32, wherein the first polynucleotide is contained within a first vector.

Embodiment N34. The method of any one of Embodiments N31 to N33, wherein the first polynucleotide is contained within a second vector.

Embodiment N35. The method of Embodiment N34, wherein the first vector and the second vector are the same.

Embodiment N36. The method of Embodiment N34, wherein the first vector is different from the second vector.

Embodiment N37. The method of Embodiment N31, wherein the cell is a mammalian cell.

Embodiment N38. The method of Embodiment N31, wherein the method has a specificity that is 2-fold higher than a specificity to a non-target nucleic acid sequence.

Embodiment N39. A method of silencing a target nucleic acid sequence in a cell, the method comprising delivering the complex of any one of Embodiments N21 to N25 to a cell containing the target nucleic acid.

Embodiment N40. The method of Embodiment N39, wherein the complex silences the target nucleic acid sequence in the cell by methylating a chromatin containing the target nucleic acid sequence and/or by introducing repressive chromatin marks to a chromatin containing the target nucleic acid sequence.

Embodiment N41. The method of Embodiment N39 or N40, wherein the cell is a mammalian cell.

Embodiment N42. The method of any one of Embodiments N39 to N41, wherein the method has a specificity that is 2-fold higher than a specificity to a non-target nucleic acid sequence.

Embodiments 1 to 36

Embodiment 1. A fusion protein comprising a nuclease-deficient RNA-guided DNA endonuclease enzyme, a Krüppel associated box (KRAB) domain, and a DNA methyltransferase domain.

Embodiment 2. The fusion protein of Embodiment 1, wherein the nuclease-deficient RNA-guided DNA endonuclease enzyme is dCas9, ddCpf1, a nuclease-deficient Cas9 variant, or a nuclease-deficient Class II CRISPR endonuclease.

Embodiment 3. The fusion protein of Embodiment 1 or 2, wherein the DNA methyltransferase domain is a Dnmt3A-3L domain.

Embodiment 4. The fusion protein of any one of Embodiments 1 to 3, wherein the nuclease-deficient RNA-guided DNA endonuclease enzyme is covalently linked to the KRAB domain via a peptide linker.

Embodiment 5. The fusion protein of any one of Embodiments 1 to 4, wherein the nuclease-deficient RNA-guided DNA endonuclease enzyme is covalently linked to the DNA methyltransferase domain via a peptide linker.

Embodiment 6. The fusion protein of any one of Embodiments 1 to 5, wherein the KRAB domain is covalently linked to the DNA methyltransferase domain via a peptide linker.

Embodiment 7. The fusion protein of any one of Embodiments 4 to 6, wherein the peptide linker is a XTEN linker.

Embodiment 8. The fusion protein of Embodiment 7, wherein the XTEN linker comprises about 16 to 80 amino acid residues.

Embodiment 9. The fusion protein of any one of Embodiments 1 to 8, further comprising a nuclear localization signal peptide.

Embodiment 10. The fusion protein of any one of Embodiments 1 to 9, wherein the fusion protein comprises, from N-terminus to C-terminus, a KRAB domain, a nuclease-deficient RNA-guided DNA endonuclease enzyme, and a DNA methyltransferase domain.

Embodiment 11. The fusion protein of any one of Embodiments 1 to 10, wherein the nuclease-deficient RNA-guided DNA endonuclease enzyme is dCas9 and the DNA methyltransferase domain is a Dnmt3A-3L domain.

Embodiment 12. The fusion protein of Embodiment 11, wherein the dCas9 is covalently linked to the KRAB domain via a peptide linker and wherein the dCas9 is covalently linked to the Dnmt3A-3L domain via a peptide linker.

Embodiment 13. The fusion protein of Embodiment 12, wherein the peptide linker is a XTEN linker.

Embodiment 14. The fusion protein of any one of Embodiments 1 to 13, wherein the fusion protein comprises the amino acid sequence of SEQ ID NO:1, 2, 3, 4, 5, 6, 7, 8, 9, 10, 11 12, 13, 14, or 15.

Embodiment 15. A nucleic acid sequence encoding the fusion protein of any one of Embodiments 1 to 14.

Embodiment 16. A complex comprising: (i) a fusion protein of any one of Embodiments 1 to 14; and (ii) a polynucleotide comprising: (a) a DNA-targeting sequence that is complementary to a target polynucleotide sequence; and (b) a binding sequence for the nuclease-deficient RNA-guided DNA endonuclease enzyme, wherein the nuclease-deficient RNA-guided DNA endonuclease enzyme is bound to the polynucleotide via the binding sequence.

Embodiment 17. The complex of Embodiment 16, wherein the target polynucleotide sequence is part of a gene.

Embodiment 18. The complex of Embodiment 16, wherein the target polynucleotide sequence is part of a transcriptional regulatory sequence.

Embodiment 19. The complex of Embodiment 16, wherein the target polynucleotide sequence is part of a promoter, enhancer, or silencer.

Embodiment 20. The complex of Embodiment 16, wherein the target polynucleotide sequence is a hypomethylated nucleic acid sequence.

Embodiment 21. The complex of Embodiment 16, wherein the target polynucleotide sequence is within about 3000 bp flanking a transcription start site.

Embodiment 22. A vector comprising the nucleic acid sequence of Embodiment 15.

Embodiment 23. The vector of Embodiment 17, further comprising a polynucleotide, wherein the polynucleotide comprises: (a) a DNA-targeting sequence that is complementary to a target polynucleotide sequence; and (b) a binding sequence for the nuclease-deficient RNA-guided DNA endonuclease enzyme.

Embodiment 24. A cell comprising the fusion protein of any one of Embodiments 1 to 14; the nucleic acid of Embodiment 15; the complex of any one of Embodiments 16 to 21; or the vector of Embodiment 22 or 23.

Embodiment 25. The cell of Embodiment 18, wherein the cell is a eukaryotic cell.

Embodiment 26. The cell of Embodiment 18, wherein the cell is a mammalian cell.

Embodiment 27. A method of silencing a target nucleic acid sequence in a cell, comprising: (i) delivering a first polynucleotide encoding a fusion protein according to any one of Embodiments 1 to 14 to a cell containing the target nucleic acid; and (ii) delivering to the cell a second polynucleotide comprising: (a) a DNA-targeting sequence that is complementary to the target nucleic acid sequence; and (b) a binding sequence for the nuclease-deficient RNA-guide DNA endonuclease enzyme, wherein the fusion protein silences the target nucleic acid sequence in the cell by methylating a chromatin containing the target nucleic acid sequence and/or by introducing repressive chromatin marks to a chromatin containing the target nucleic acid sequence Embodiment 28. The method of Embodiment 27, wherein the first polynucleotide is contained within a first vector.

Embodiment 29. The method of Embodiment 27, wherein the first polynucleotide is contained within a second vector.

Embodiment 30. The method of Embodiment 28 or 29, wherein the first vector and the second vector are the same.

Embodiment 31. The method of Embodiment 28 or 29, wherein the first vector is different from the second vector.

Embodiment 32. The method of any one of Embodiments 27 to 31, wherein the cell is a mammalian cell.

Embodiment 33. The method of any one of Embodiments 27 to 32, wherein the method has a specificity that is 2-fold higher than a specificity to a non-target nucleic acid sequence.

Embodiment 34. A method of silencing a target nucleic acid sequence in a cell, the method comprising delivering the complex of any one of Embodiments 16 to 20 to a cell containing the target nucleic acid, wherein the complex silences the target nucleic acid sequence in the cell by: (i) methylating a chromatin containing the target nucleic acid sequence, (ii) introducing repressive chromatin marks to a chromatin containing the target nucleic acid sequence, or (iii) methylating a chromatin containing the target nucleic acid sequence and introducing repressive chromatin marks to a chromatin containing the target nucleic acid sequence.

Embodiment 35. The method of Embodiment 34, wherein the cell is a mammalian cell.

Embodiment 36. The method of Embodiment 34 or 35, wherein the method has a specificity that is 2-fold higher than a specificity to a non-target nucleic acid sequence.

EXAMPLES

Embodiments and aspects herein are further illustrated by the following examples. The examples are merely intended to illustrate embodiments and aspects, and are not to be construed to limit the scope herein.

Figure 1B:
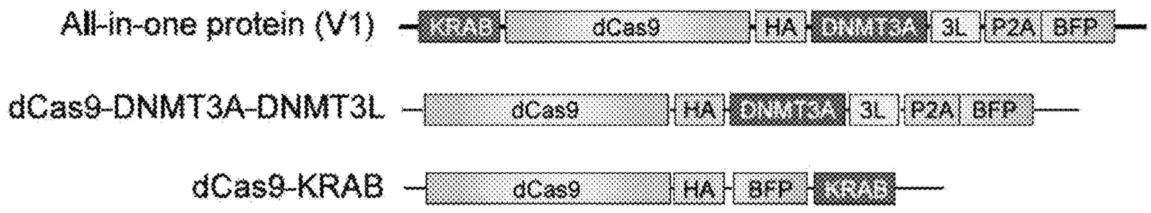

Example 1 dCas9-fused epigenetic modulators tested for permanent gene silencing. The initial version (V1, p76 (SEQ ID NO:1)) of the all-in-one protein (FIG. 1A) has the KRAB domain fused to the —N-terminus of dCas9 (SEQ ID NO:23), separated by a GGSGGGS (SEQ ID NO:17) linker, and Dnmt3A-Dnmt3L at the C-terminus of dCas9 (separated by a EASGSGRASPGIPGSTR (SEQ ID NO:19) linker). Another all-in-one proteins that combined the KRAB domain (SEQ ID NO:16), dCas9 (D10A, H208A), Dnmt3A-Dnmt3L (SEQ ID NO:33; where SEQ ID NO:26 is Dnmt3A and SEQ ID NO:28 is Dnmt3L) into one polypeptide (FIG. 1B). With reference to FIG. 1B, the dCas9-KRAB protein was adapted from Gilbert et al., Cell 2013 for CRISPR interference (CRISPRi) applications, and the dCas9-Dnmt3A-Dnmt3L fusion was adapted from Stepper et al., Nucleic Acids Research, 2016.

Figure 1C:
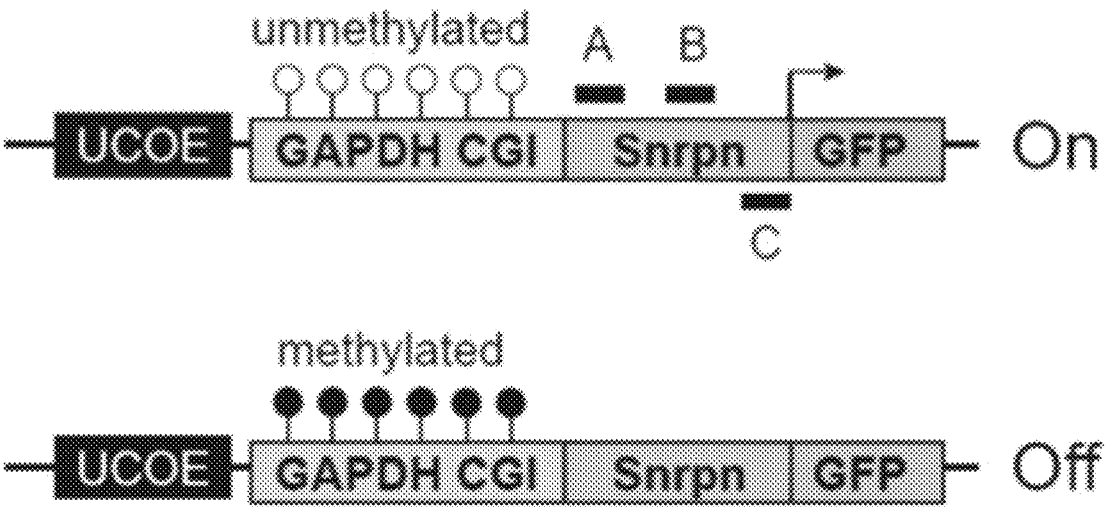
Figure 1D:
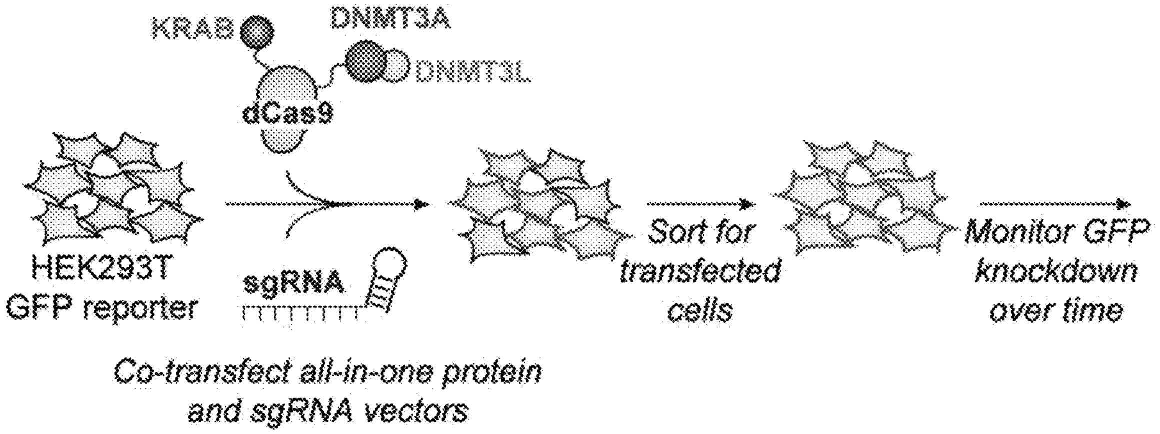
Figure 1E:
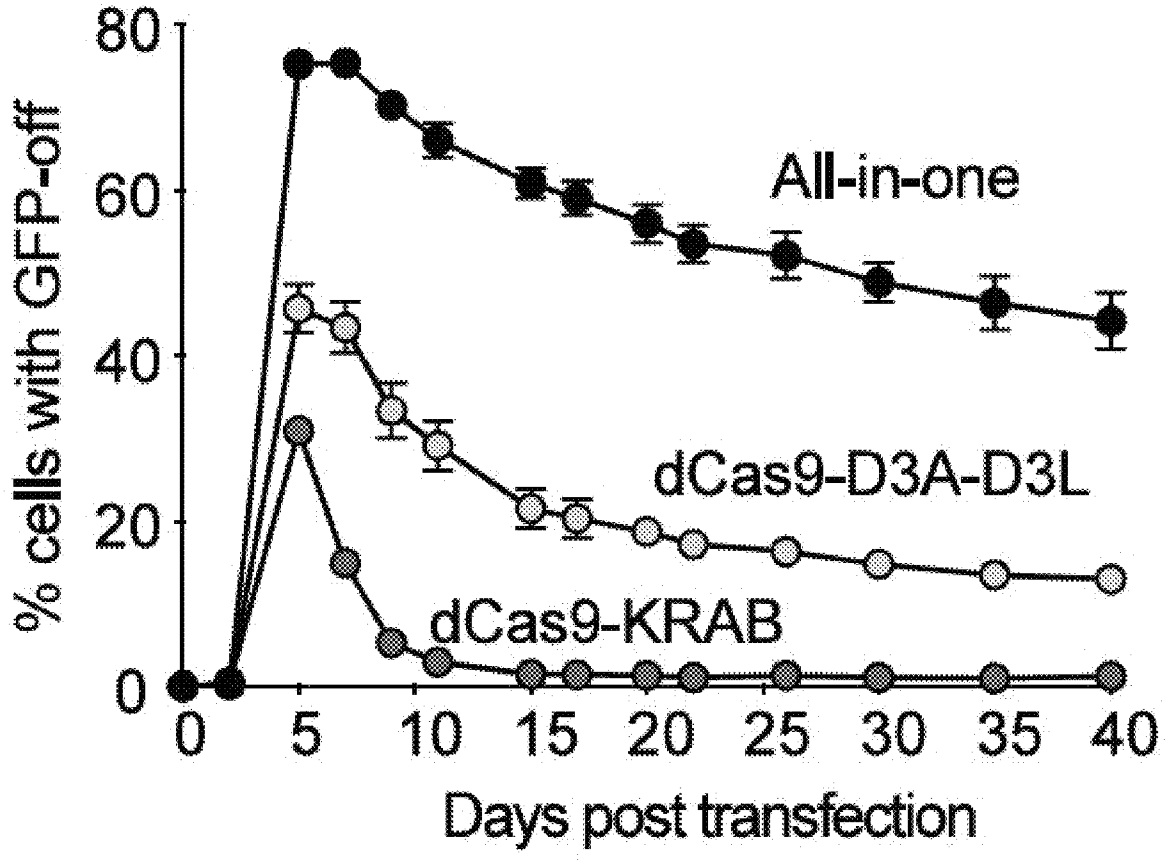
Figure 1F:
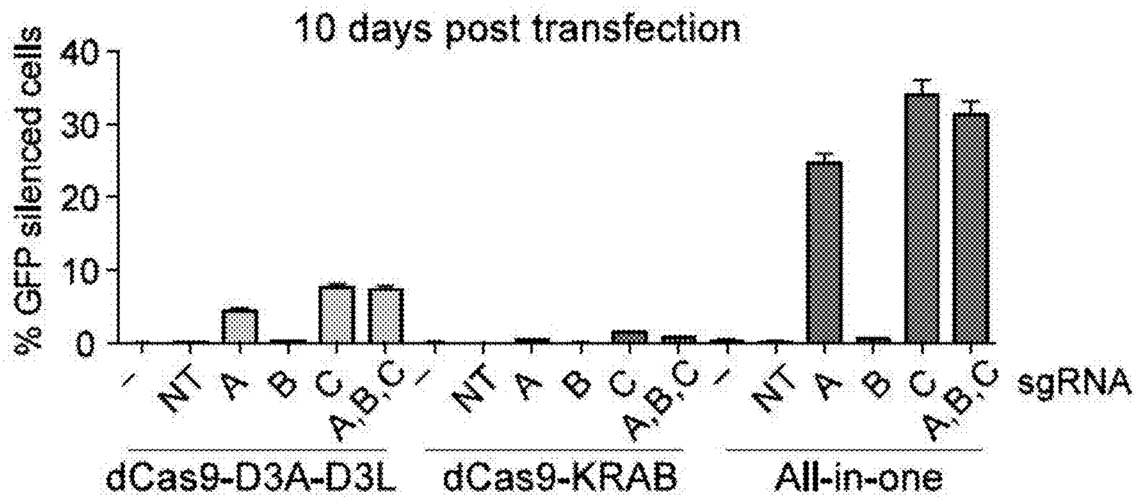

The activity of the V1 epigenetic editor was tested in HEK293T cells using a DNA-methylation sensitive GFP reporter (adapted from Stelzer et al., Cell 2015) to assess long-term silencing by the all-in-one protein (FIG. 1C). A ubiquitous chromatin opening element (UCOE) was added upstream of the GAPDH CpG island (CGI) to prevent background silencing of the lentiviral vector in mammalian cells. The gfp gene is turned off when the GAPDH CGI is methylated. A, B and C denote positions we encoded single guide RNAs (sgRNA) to target in the promoter. These targeted sequences and corresponding sgRNA sequences are listed in the Table 1 below. Two plasmids were co-transfected into cells, one encoding the hit-and-run protein and the other plasmid encoding a sgRNA (FIG. 1D). Two days post-transfection, cells that express the hit-and-run protein and sgRNA-expressing vector are sorted. GFP fluorescence is assessed over time by flow cytometry. A population of cells undergoing long-term silencing of the GFP reporter was observed when the all-in-one protein is expressed with sgRNAs (FIG. 1E). The number of cells undergoing long-term silencing was higher than dCas9-Dnmt3A-Dnmt3L (lacking the KRAB domain).

TABLE 1

| Name | Targeted sequence (5' to 3') | sgRNA sequence (5' to 3') |
|---|---|---|
| A (JKNg156) | ACTGCGGAAATTTGAGCGT (SEQ ID NO: 37) | ACGCTCAAATTTCCGCAGT (SEQ ID NO: 38) |
| B (JKNg158) | AGGCAATGGCTGCACATGC (SEQ ID NO: 39) | GCATGTGCAGCCATTGCCT (SEQ ID NO: 40) |
| C (JKNg160) | GACGCTTGGTTCTGAGGAG (SEQ ID NO: 41) | CTCCTCAGAACCAAGCGTC (SEQ ID NO: 42) |

Silencing of the GFP reporter is dependent on the sgRNA sequence, with guide C resulting in the highest level of silencing among the three sgRNA sequences tested. Pooling the sgRNAs encoding different sequences did not have a significant change in gene silencing.

Figures 2A, 2B, 2C:
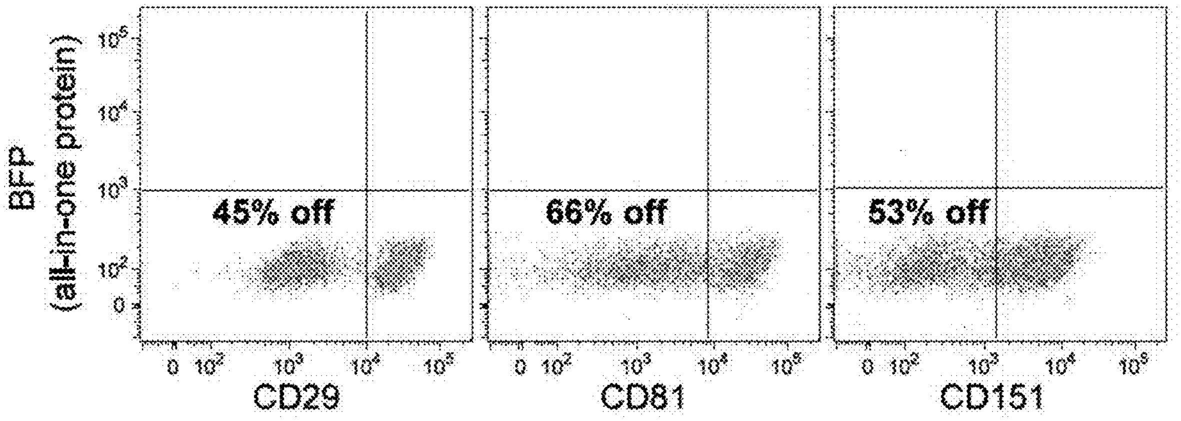
FIGS. 2A-2F describe long-term silencing of endogenous genes.
Figure 2D:
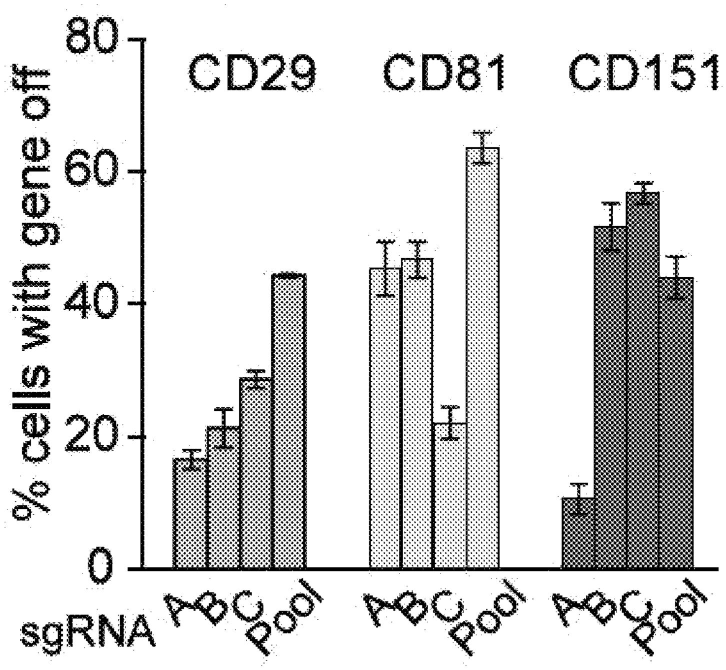

Three genes (CD29, CD81, CD151) were targeted for long term silencing using the hit-and-run fusion protein. All three proteins are cell surface-localized and knockdown was assessed by cell surface antibody staining of cells, followed by flow cytometry. Representative flow cytometry data are shown in FIGS. 2A-2C taken 22 days post-transfection. Quadrant IV represents cells that have turned off the gene, indicated by the percentage of cells with the gene off. The lack of cells in Quadrants I and II signify that the hit-and-run protein (marked by BFP) is no longer present in the cells. FIG. 2D provides quantification of silencing of CD29, CD81 and CD151 with three different sgRNA sequences or a pool of all three sgRNAs. The targeted DNA sequences and their sgRNAs used in this experiment are summarized in Table 2.

TABLE 2

| Name | Targeted sequence (5' to 3') | sgRNA sequence (5' to 3') |
|---|---|---|
| CD29, sgRNA-A | TCCGGAAACGCATTCCTCT (SEQ ID NO: 43) | AGAGGAATGCGTTTCCGGA (SEQ ID NO: 44) |

TABLE 2-continued

| Name | Targeted sequence (5' to 3') | sgRNA sequence (5' to 3') |
|---|---|---|
| CD29, sgRNA-B | CCGCGTCAGCCCGGCCCGG (SEQ ID NO: 45) | CCGGGCCGGGCTGACGCGG (SEQ ID NO: 46) |
| CD29, sgRNA-C | CGACTCCCGCTGGGCCTCT (SEQ ID NO: 47) | AGAGGCCCAGCGGGAGTCG (SEQ ID NO: 48) |
| CD81, sgRNA-A | ccgttgcgcgctcgctctc (SEQ ID NO: 49) | gagagcgagcgcgcaacgg (SEQ ID NO: 50) |
| CD81, sgRNA-B | CCGCGCATCCTGCCAGGCC (SEQ ID NO: 51) | GGCCTGGCAGGATGCGCGG (SEQ ID NO: 52) |
| CD81, sgRNA-C | CCAACTTGGCGCGTTTCGG (SEQ ID NO: 53) | CCGAAACGCGCCAAGTTGG (SEQ ID NO: 54) |
| CD151, sgRNA-A | ACCACGCGTCCGAGTCCGG (SEQ ID NO: 55) | CCGGACTCGGACGCGTGGT (SEQ ID NO: 56) |
| CD151, sgRNA-B | TGCTCATTGTCCCTGGACA (SEQ ID NO: 57) | TGTCCAGGGACAATGAGCA (SEQ ID NO: 58) |
| CD151, sgRNA-C | GGACACCCTGCTCATTGTC (SEQ ID NO: 59) | GACAATGAGCAGGGTGTCC (SEQ ID NO: 60) |

Figure 2E:
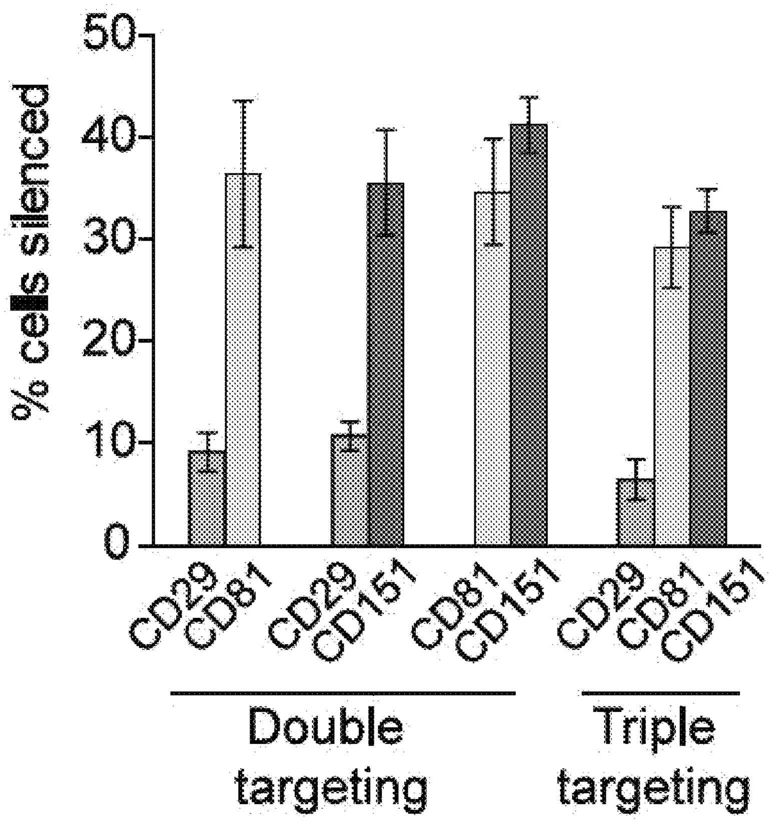

Two or three genes were simultaneously targeted to show that the all-in-protein can be multiplexed by co-delivery of sgRNAs targeting different genes. NT sgRNA refers to non-targeting sgRNA control. The results are shown in FIG. 2E.

Figure 2F:
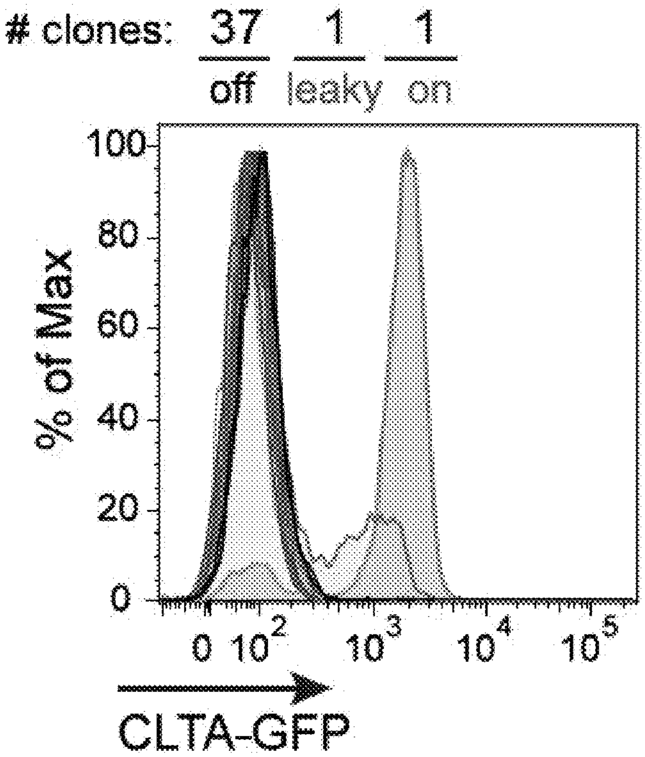

Gene silencing of cells that started as a single clone were followed and it was observed the majority of cells have maintained the targeted CLTA gene off (37 out of 39 clones). The plot in FIG. 2F represents a time point taken 9 months post transfection of the all-in-one protein and sgRNA targeting the CLTA gene.

The system described herein can target any genes in the mammalian genomes, especially those that contain CpG islands at the gene promoter. The Dnmt3A-Dnmt3L canonically targets CpG dinucleotides. Examples of genes that can be targeted include, but are not limited to, CXCR4, CD4, CD8, CD45, PD-1, CLTA-4, TGFBR, TCRa, TCRb, B2M.

Example 3

Figure 3A:
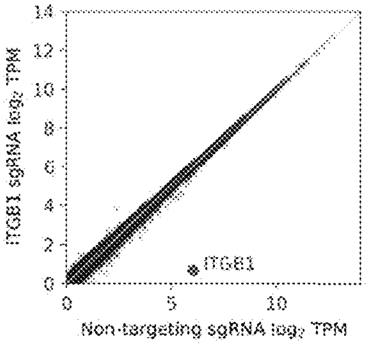
FIGS. 3A-3I describe long-term silencing of endogenous genes.
Figure 3B:
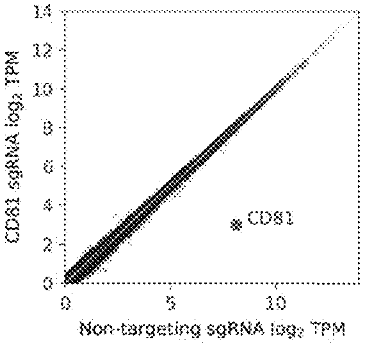
Figure 3C:
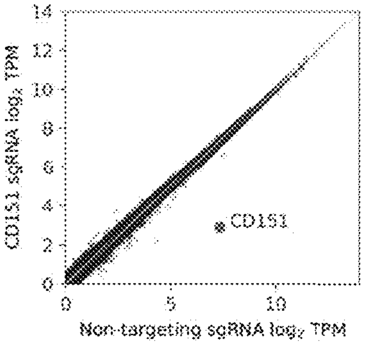
Figure 3D:
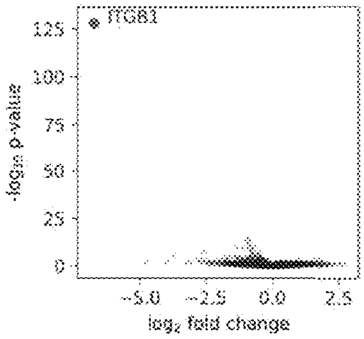
Figure 3E:
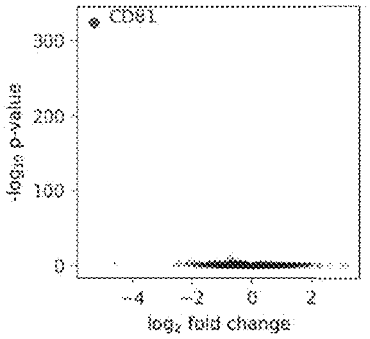
Figure 3F:
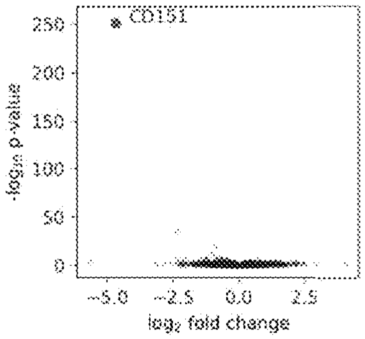
Figure 3G:
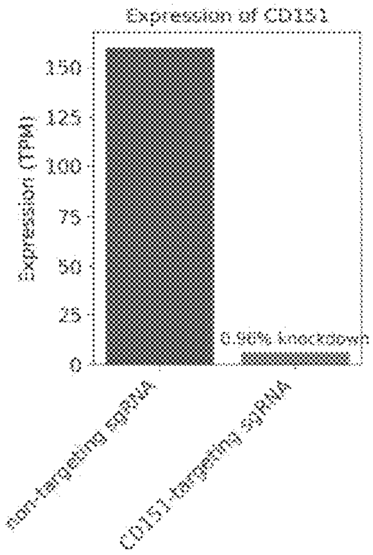
Figure 3H:
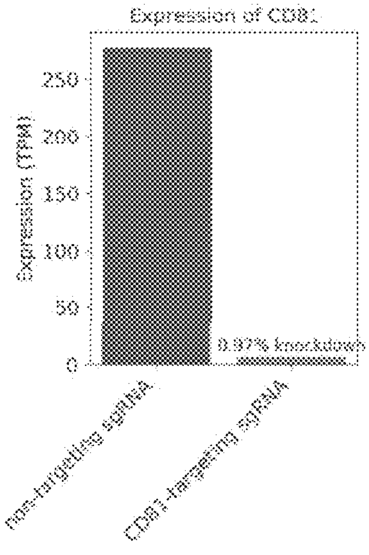
Figure 3I:
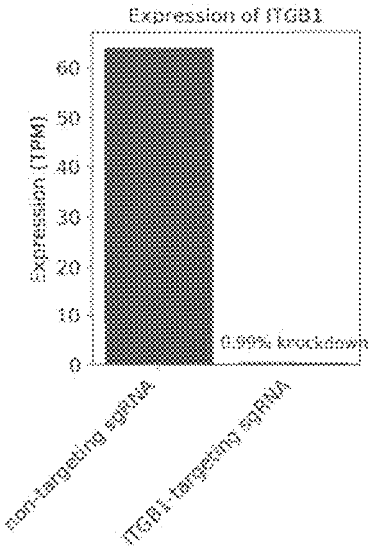

Cells were harvested that lost expression of ITGB1 (CD29), CD81 and CD151 thirty-six days post-transfection and analyzed their RNA expression profiles were analyzed. As shown in FIGS. 3A-3C, successful knockdown of the targeted genes was detected compared to the non-targeting sgRNA control. FIGS. 3D-3F are volcano plots show that the targeted gene is the only significant gene knocked down for each experiment, signifying high specificity of gene silencing. FIGS. 3G-3I are the quantification of transcript levels showing greater than 96% knockdown of the targeted gene.

Example 4

Figure 4A:
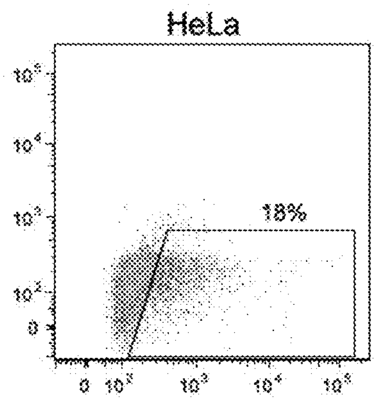
FIGS. 4A-4H describe long-term gene silencing in different mammalian cell lines.
Figure 4B:
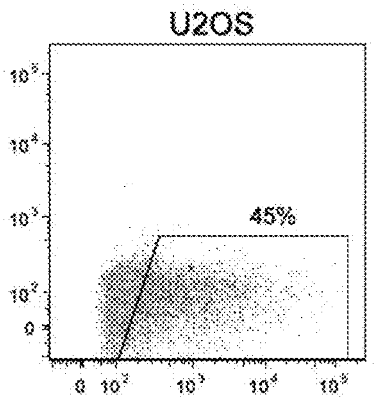
Figure 4C:
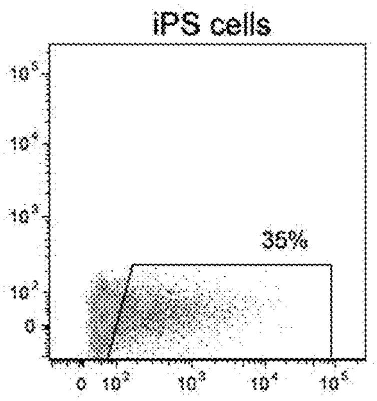
Figure 4D:
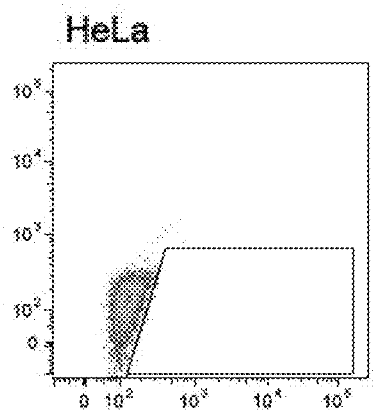
Figure 4E:
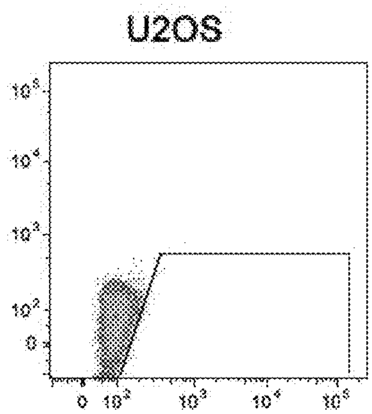
Figure 4F:
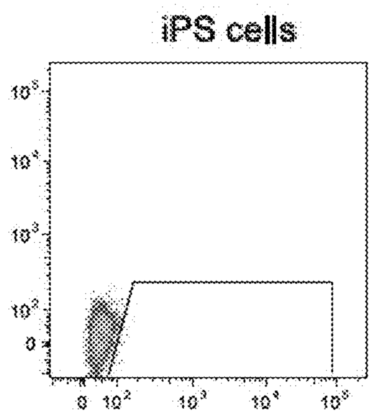
Figure 4G:
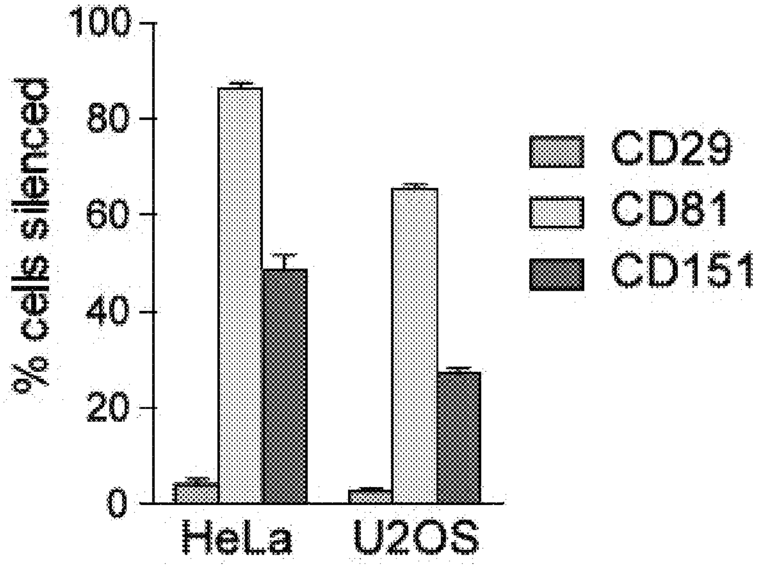
Figure 4H:
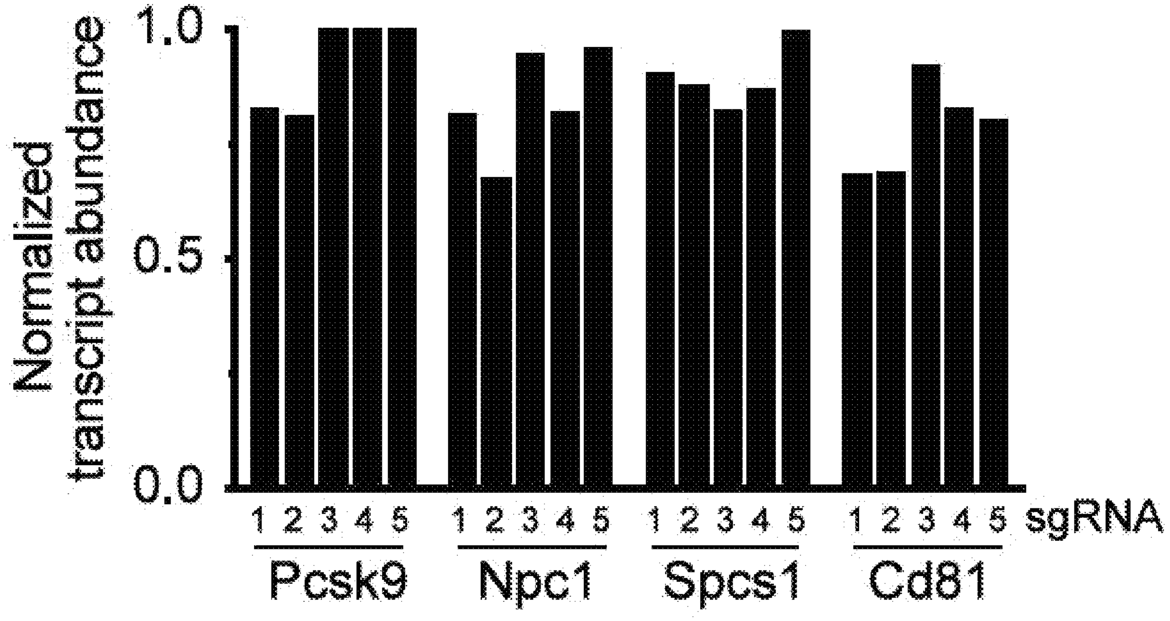

The all-in-one protein can be transfected and expressed in HeLa (cervical), U2OS (bone) and human induced pluripotent stem cells (iPSC). Flow cytometry plots in FIGS. 4A-4F show BFP expression, which is fused to the protein. Three endogenous genes in HeLa and U2OS cells (i.e., CD29, CD81, and CD151) were targeted. As shown in FIG. 4G, stable silencing, measured at 18 days post-transfection, was detected. Gene silencing in AML12 mouse hepatocyte cell lines was detected when targeting Pcsk9, Npc1, Spcs1 and Cd81. Silencing was detected by qPCR, measured 14 days post transfection, as shown in FIG. 4H. The sgRNA sequences used in this experiment are summarized in Table 3

TABLE 3

| Name | Targeted sequence (5' to 3') | sgRNA sequence (5' to 3') |
|---|---|---|
| Pcsk9 sgRNA-1 | TCCGGAAACGCATTCCTCT (SEQ ID NO: 43) | AGAGGAATGCGTTTCCGGA (SEQ ID NO: 44) |
| Pcsk9 sgRNA-2 | ACCGGCAGCCTGCGCGTCC (SEQ ID NO: 61) | GGACGCGCAGGCTGCCGGT (SEQ ID NO: 62) |
| Pcsk9 sgRNA-3 | CGATGGGCACCCACTGCTC (SEQ ID NO: 63) | GAGCAGTGGGTGCCCATCG (SEQ ID NO: 64) |
| Pcsk9 sgRNA-4 | CCTTCACGTGGACGCGCAG (SEQ ID NO: 65) | CTGCGCGTCCACGTGAAGG (SEQ ID NO: 66) |
| Pcsk9 sgRNA-5 | CGTGAAGGTGGAAGCCTTC (SEQ ID NO: 67) | GAAGGCTTCCACCTTCACG (SEQ ID NO: 68) |

TABLE 3-continued

| Name | Targeted sequence (5' to 3') | sgRNA sequence (5' to 3') |
|---|---|---|
| Npc1 sgRNA-1 | CTCCTTGGTCAGGCGCCGG (SEQ ID NO: 69) | CCGGCGCCTGACCAAGGAG (SEQ ID NO: 70) |
| Npc1 sgRNA-2 | TGGTCAGGCGCCGGTTCCG (SEQ ID NO: 71) | CGGAACCGGCGCCTGACCA (SEQ ID NO: 72) |
| Npc1 sgRNA-3 | TAGAGGTCGCCTTCTCCTC (SEQ ID NO: 73) | GAGGAGAAGGCGACCTCTA (SEQ ID NO: 74) |
| Npc1 sgRNA-4 | CGACGCTCGGGTCGCGGTG (SEQ ID NO: 75) | CACCGCGACCCGAGCGTCG (SEQ ID NO: 76) |
| Npc1 sgRNA-5 | ATGCTGTCGCCGCGCGGGG (SEQ ID NO: 77) | CCCCGCGCGGCGACAGCAT (SEQ ID NO: 78) |
| Spcs1 sgRNA-1 | CTCACCCTCACCGGAGCCA (SEQ ID NO: 79) | TGGCTCCGGTGAGGGTGAG (SEQ ID NO: 80) |
| Spcs1 sgRNA-2 | CCGCAAACTTTACTCCTTA (SEQ ID NO: 81) | TAAGGAGTAAAGTTTGCGG (SEQ ID NO: 82) |
| Spcs1 sgRNA-3 | CTCGGAGACATCCGCTTCC (SEQ ID NO: 60) | GGAAGCGGATGTCTCCGAG (SEQ ID NO: 60) |
| Spcs1 sgRNA-4 | CTCCTAAGATTGGCTTCAC (SEQ ID NO: 83) | GTGAAGCCAATCTTAGGAG (SEQ ID NO: 84) |
| Spcs1 sgRNA-5 | CCGGAGCCACTCCTAAGAT (SEQ ID NO: 85) | ATCTTAGGAGTGGCTCCGG (SEQ ID NO: 86) |
| Cd81 sgRNA-1 | TTCTCTACCCTACGTCTCA (SEQ ID NO: 87) | TGAGACGTAGGGTAGAGAA (SEQ ID NO: 88) |
| Cd81 sgRNA-2 | TACGTCTCATTCTCCGCAA (SEQ ID NO: 89) | TTGCGGAGAATGAGACGTA (SEQ ID NO: 90) |
| Cd81 sgRNA-3 | GCTAGGCCTCCAGCCCTTC (SEQ ID NO: 91) | GAAGGGCTGGAGGCCTAGC (SEQ ID NO: 92) |
| Cd81 sgRNA-4 | ACAGGTGGCGCCGCAACTT (SEQ ID NO: 93) | AAGTTGCGGCGCCACCTGT (SEQ ID NO: 94) |
| Cd81 sgRNA-5 | AGCCGGAGGCGCGAGAGTC (SEQ ID NO: 95) | GACTCTCGCGCCTCCGGCT (SEQ ID NO: 96) |

Example 5

FIG. 5 provides a schematic of the all-in-one protein constructs that were designed and tested for gene silencing. The initial design (p76, V1) of SEQ ID NO:1 was modified to encode XTEN linkers (e.g., 16 amino acids (SEQ ID NO: 31) or 80 amino acids (SEQ ID NO:32)) at either the N or C terminus of dCas9 (SEQ ID NO:29). All vectors contain HA tags (SEQ ID NO:24) at the C-terminus of dCas9. In aspects, CAG promoter is used since it provides good expression, for example, in constructs p'76, and p90-102, p112 (V2). With reference to FIG. 5, the protein constructs of p90 to p102 correspond to SEQ ID NOS:2-14, respectively, and protein construct p112 corresponds to SEQ ID NO:15.

Figure 6A:
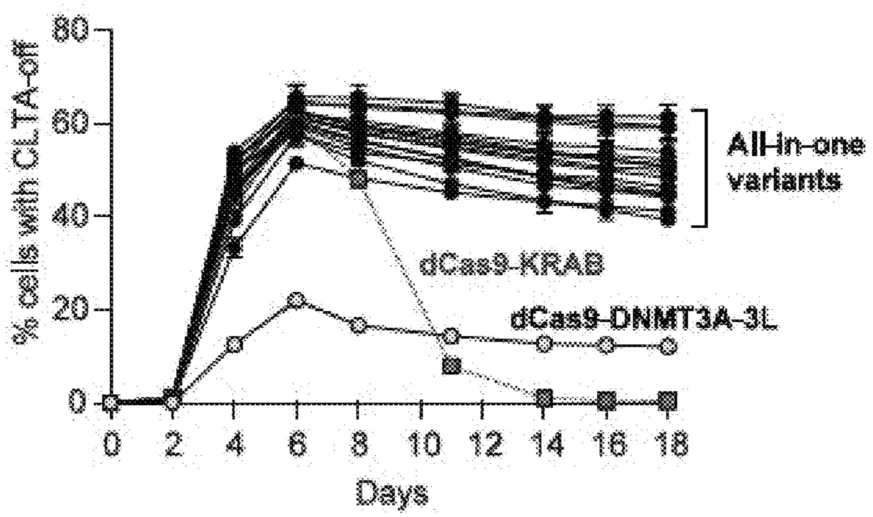
FIGS. 6A-6E describe gene silencing activities of all-in-one protein variants.
Figure 6B:
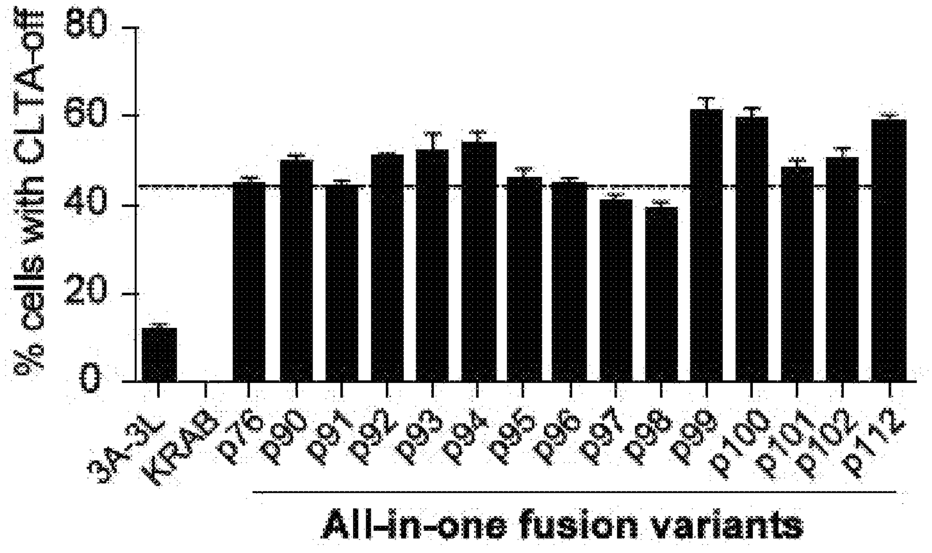
Figure 6C:
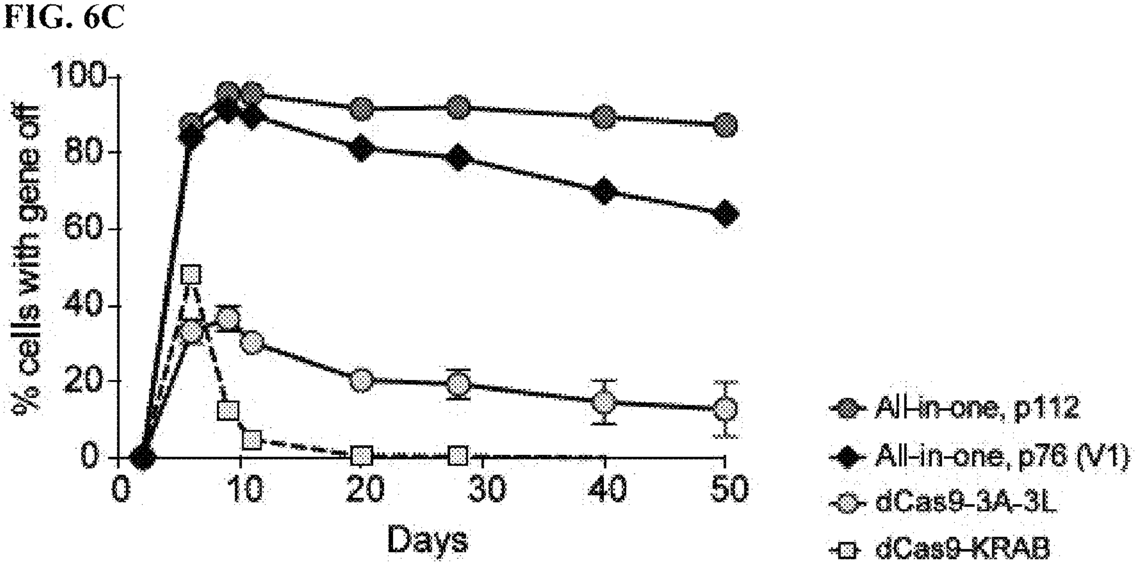
Figure 6D:
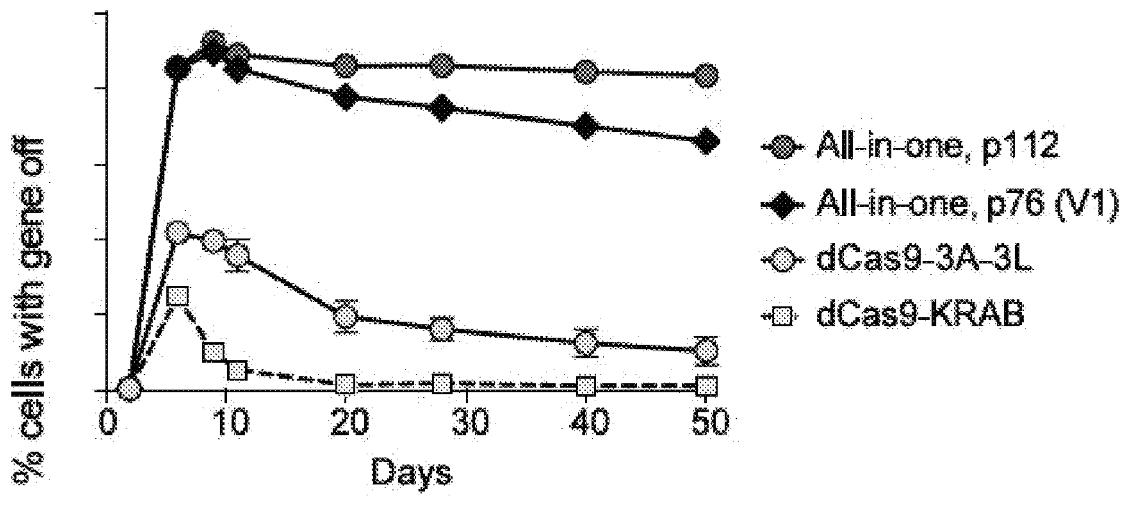
Figure 6E:
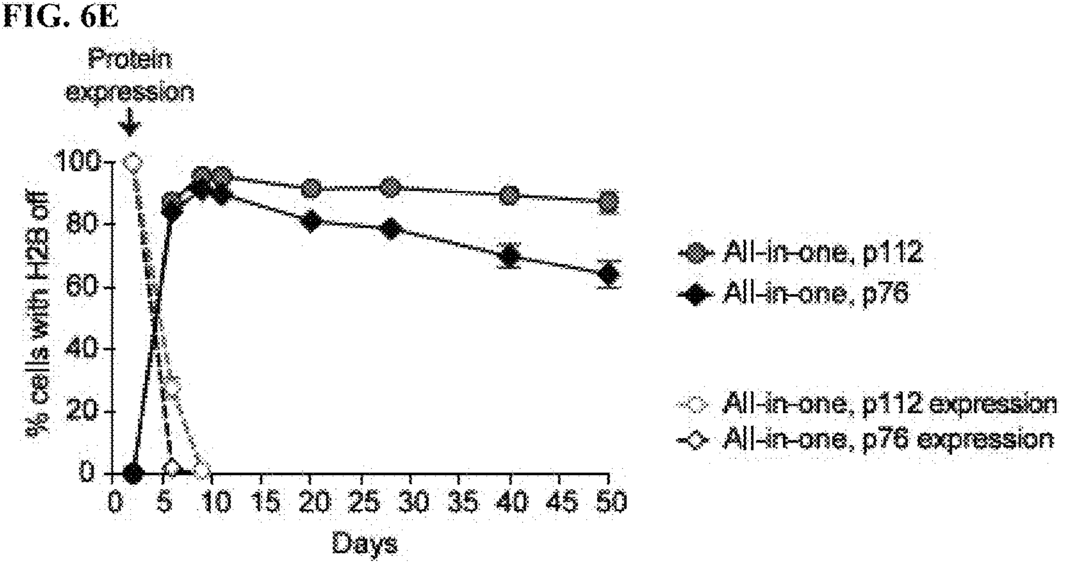

The protein constructs shown in FIG. 5 were tested for silencing of the CLTA gene in HEK293T cells for 18 days post-transfection (FIGS. 6A-6B). Variable levels of gene silencing activities were detected, including a panel of variants with more durable gene silencing compared to the p76 (V1) design such as p99 (SEQ ID NO:11), p100 (SEQ ID NO:12), and p112 (SEQ ID NO:15). FIGS. 6A and 6B show that the dCas9-KRAB and dCAS9-Dnmt3A-Dnmt3L constructs showed transient and lower efficiency of long term silencing.

p76 (SEQ ID NO:1), p112 (SEQ ID NO:15) were tested for silencing the HIST2H2BE (H2B) endogenous gene and a synthetic Snrpn-GFP reporter gene stably expressed in HEK293T cells (FIGS. 6C-6D). Cells were followed for 50 days post-transfection. The p112 variant sustained gene silencing at a higher efficiency than the p76 (V1) design. The dCas9-Dnmt3A-Dnmt3L and dCas9-KRAB fusion proteins have transient and lower efficiency of long term silencing. FIG. 6E provides a plot of protein expression of p76 and p112 over the 50 day time course to turn off the HIST2H2BE (H2B) gene. Protein levels were measured by flow cytometry detection of BFP, which is co-expressed with the all-in-one protein.

Example 7

Figure 7A:
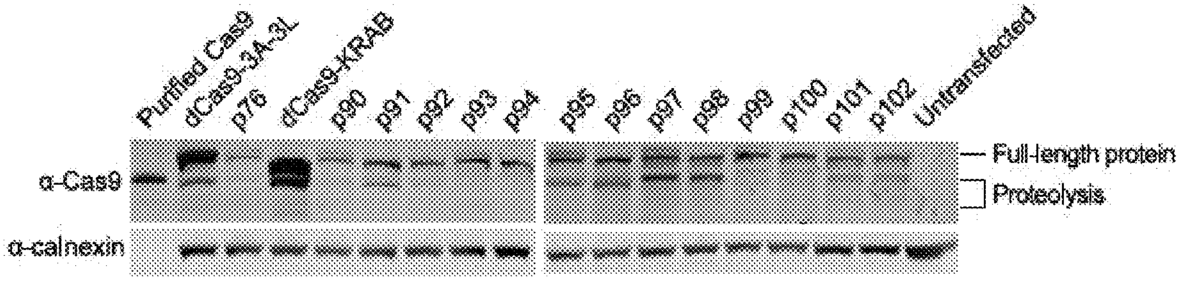
FIGS. 7A-7B provide Western blots of all-in-one-protein variants.

Western blot analysis was performed with the all-in-one protein variants p'76, p90-p102 using an antibody against *Steptococcus pyogenes* Cas9. With reference to FIG. 7A, the top band represents full-length protein and smaller-sized bands represent proteolysis of the all-in-one protein. Variants that show little proteolysis, such as p99 (SEQ ID NO:11), p100 (SEQ ID NO:12), and p102 (SEQ ID NO:14), exhibited higher efficiency of gene silencing. Variants with high levels of proteolysis, such as p96 (SEQ ID NO:8) and p97 (SEQ ID NO:9), led to lower efficiency of sustained gene silencing.

Figure 7B:

Western blot analysis was performed with the all-in-one protein variants to detect free Dnmt3A that is cleaved from the fusion protein. As shown in FIG. 7B, variants that had little or no detectable free Dnmt3, such as p92 (SEQ ID NO:4), p100 (SEQ ID NO:12), p101 (SEQ ID NO:13), and p102 (SEQ ID NO:14), had higher efficiency of sustained gene silencing compared to variants with detectable cleaved Dnmt3A, i.e., p76 (SEQ ID NO:1), p91 (SEQ ID NO:3), p96 (SEQ ID NO:8), p98 (SEQ ID NO:10).

Example 8

Figure 8A:
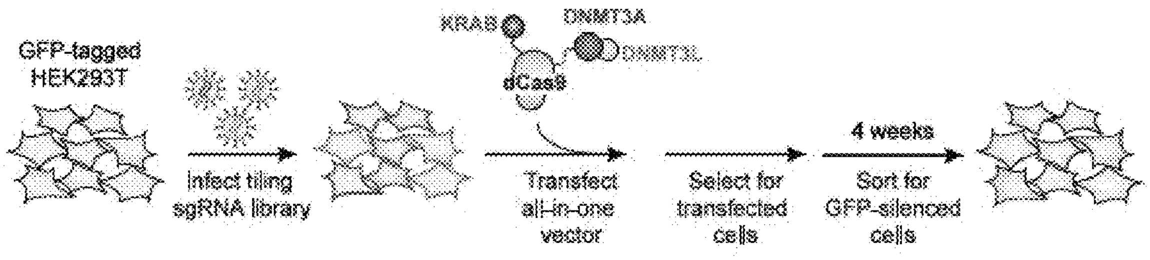
FIGS. 8A-8E describe pooled screen to determine optimal sgRNAs.
Figure 8B:
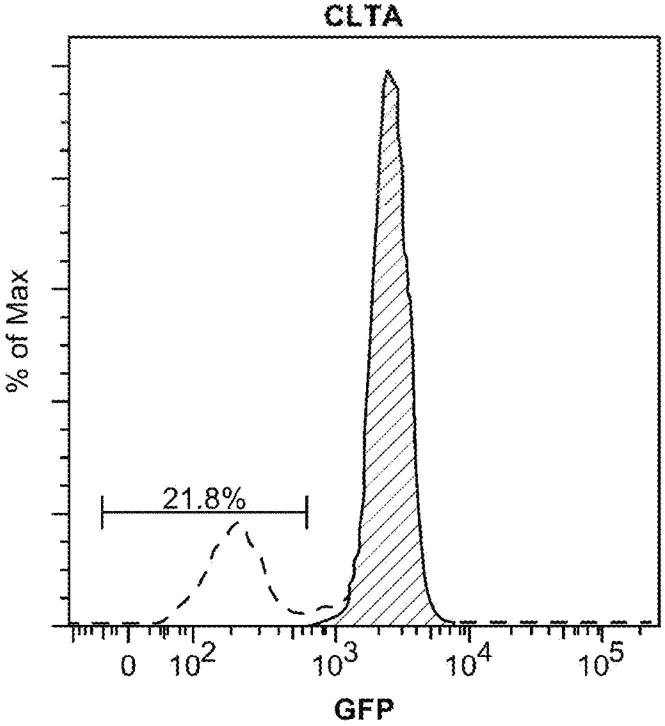
Figure 8C:
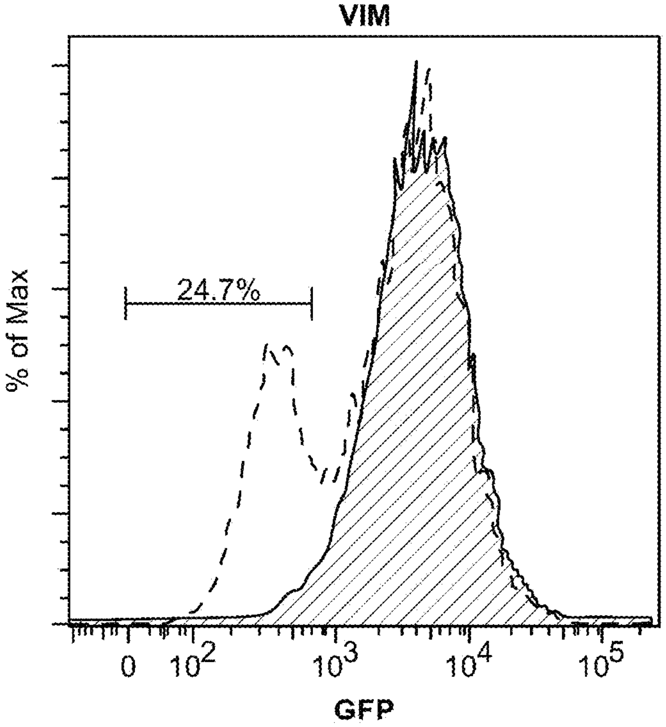
Figure 8D:
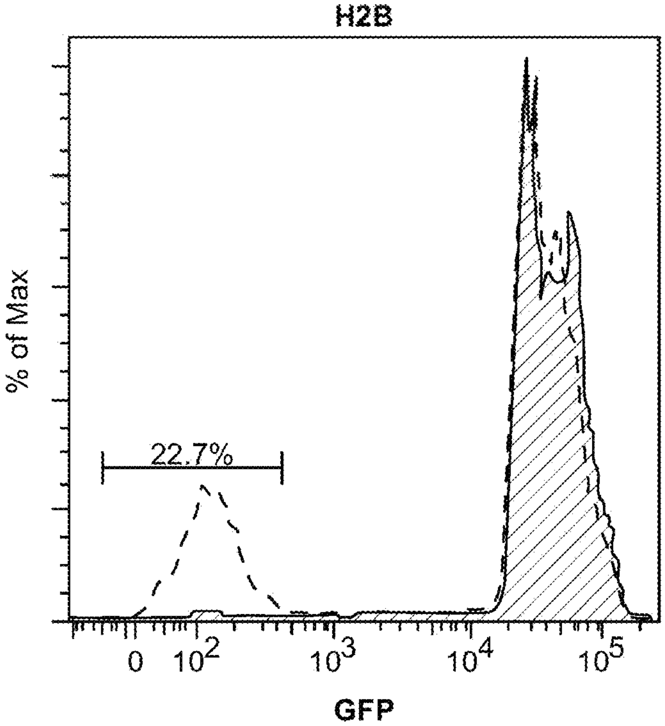
Figure 8E:
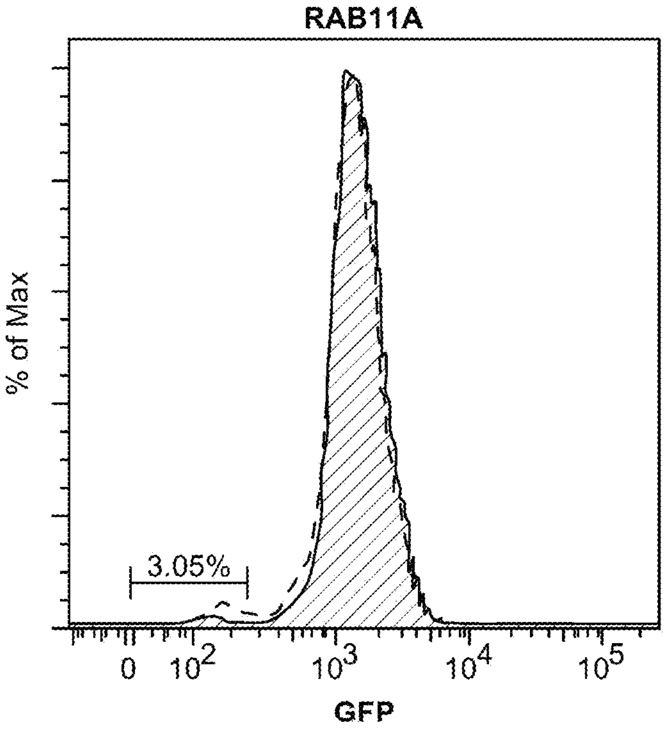
Figure 9A:
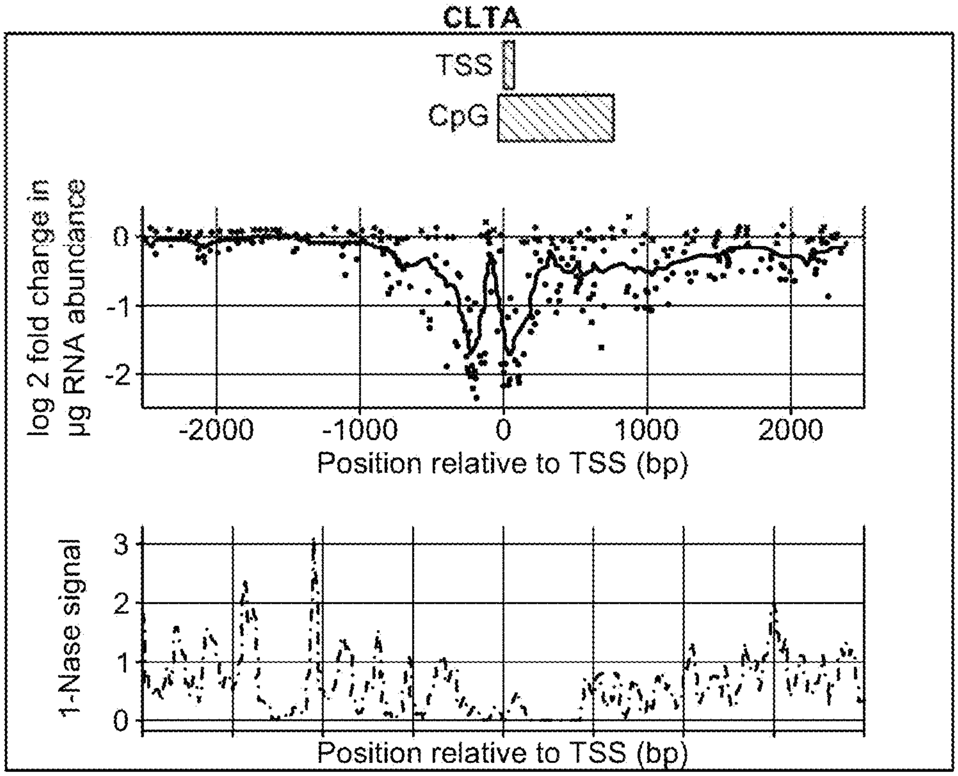
FIGS. 9A-9D are maps of sgRNA functionality across the transcription start site of the targeted gene, including CLTA (FIG. 9A), H2B (FIG. 9B), RAB11 (FIG. 9C), and VIM (FIG. 9D). The transcription start site (TSS) and CpG island are annotated above each plot. Each dot represents one sgRNA and its efficacy in long term gene silencing is plotted as the log 2 fold change in sgRNA abundance. Nucleosome occupancy (bottom plot) is plotted from MNase signal.
Figure 9B:
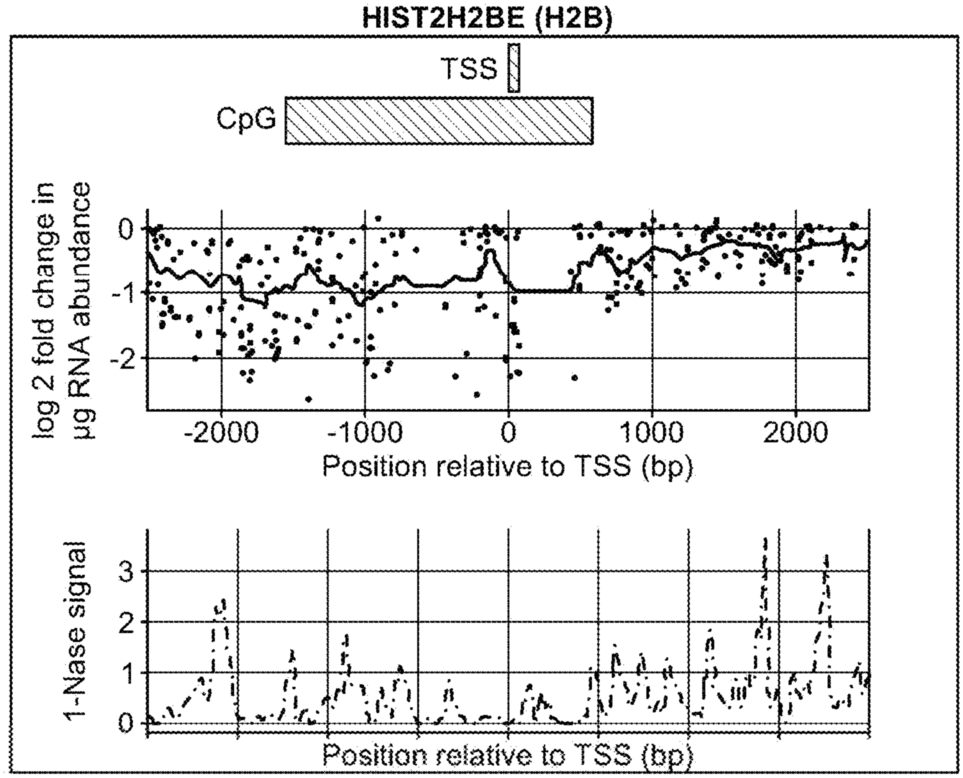
Figure 9C:
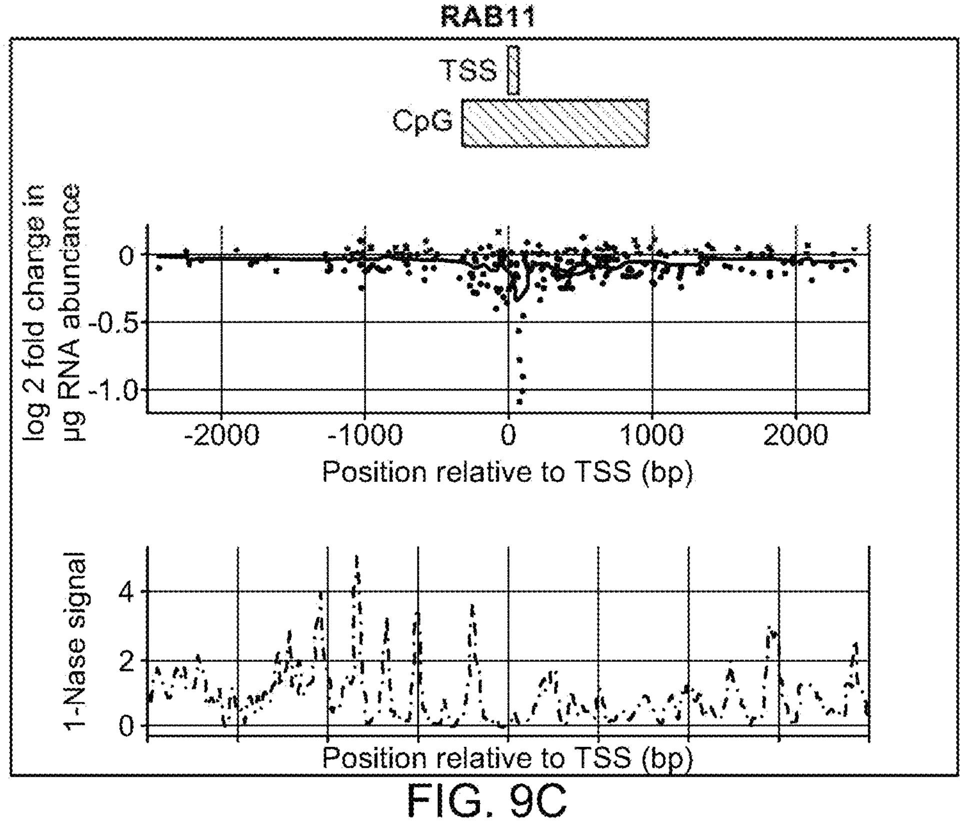
Figure 9D:
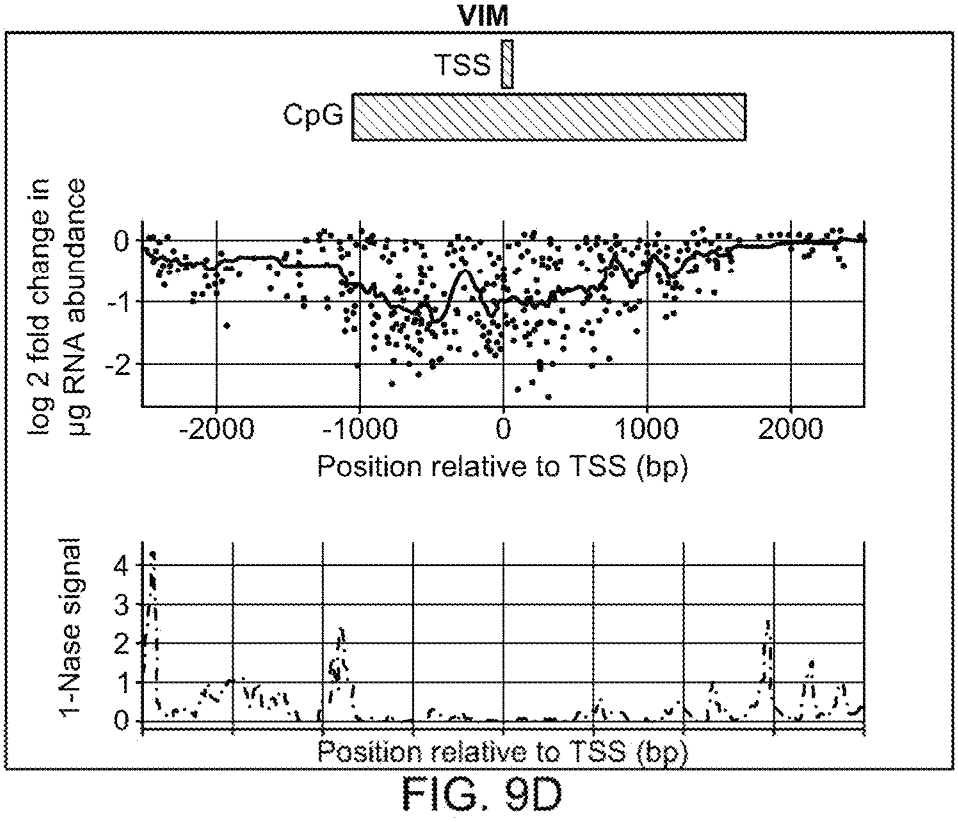

A pooled screen was assayed, as shown in FIG. 8A, to determine the optimal sgRNAs that leads to long term gene silencing. Four HEK293T cell lines were used, each with a different gene with a GFP tag (CLTA, VIM, HIST2H2BE (H2B), and RAB11A). Tiling libraries consisting of sgRNAs that span+/−2.5 kb from the transcription start site (TSS) of each gene were stably expressed in cells by lentiviral delivery, followed by transient expression plasmid DNA expressing the all-in-one protein. Four weeks post-transfection, cells that maintained gene silencing were sorted to determine the sgRNA identity. FIGS. 8B-8E are flow cytometry histograms showing the percent of cells undergoing gene silencing four weeks post-transfection.

FIGS. 9A-9D are maps of sgRNA functionality across the transcription start site of the targeted gene (CLTA, H2B, RAB11, VIM). The transcription start site (TSS) and CpG island are annotated above each plot. Each dot represents one sgRNA and its efficacy in long term gene silencing is plotted as the log 2 fold change in sgRNA abundance. Nucleosome occupancy (bottom plot) is plotted from MNase signal.

Example 9

Figure 10A:
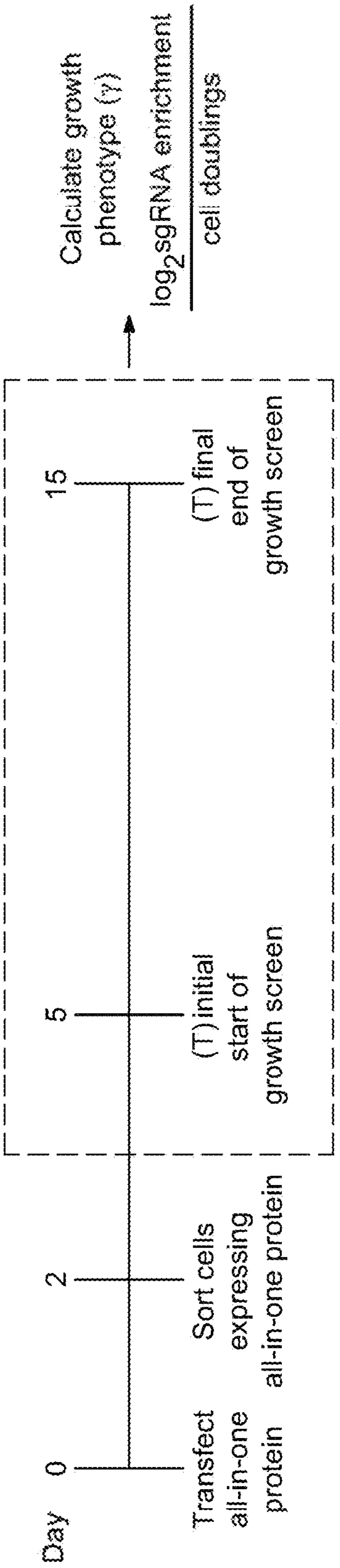
FIGS. 10A-10E describe functional sgRNAs for long term gene silencing.
Figure 10B:
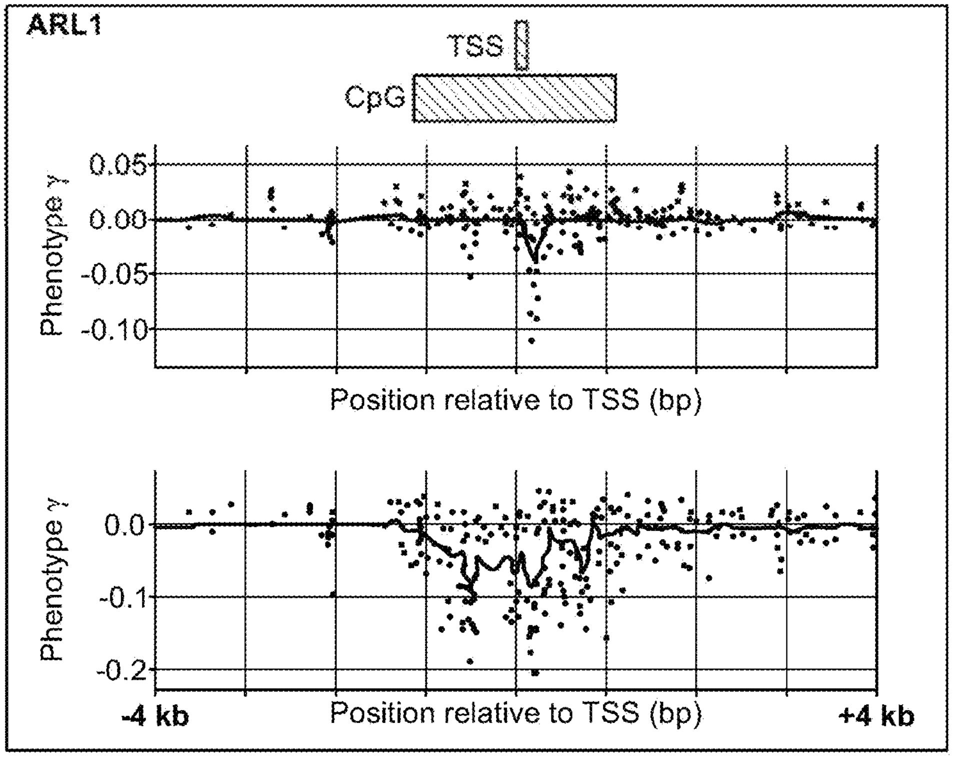
Figure 10C:
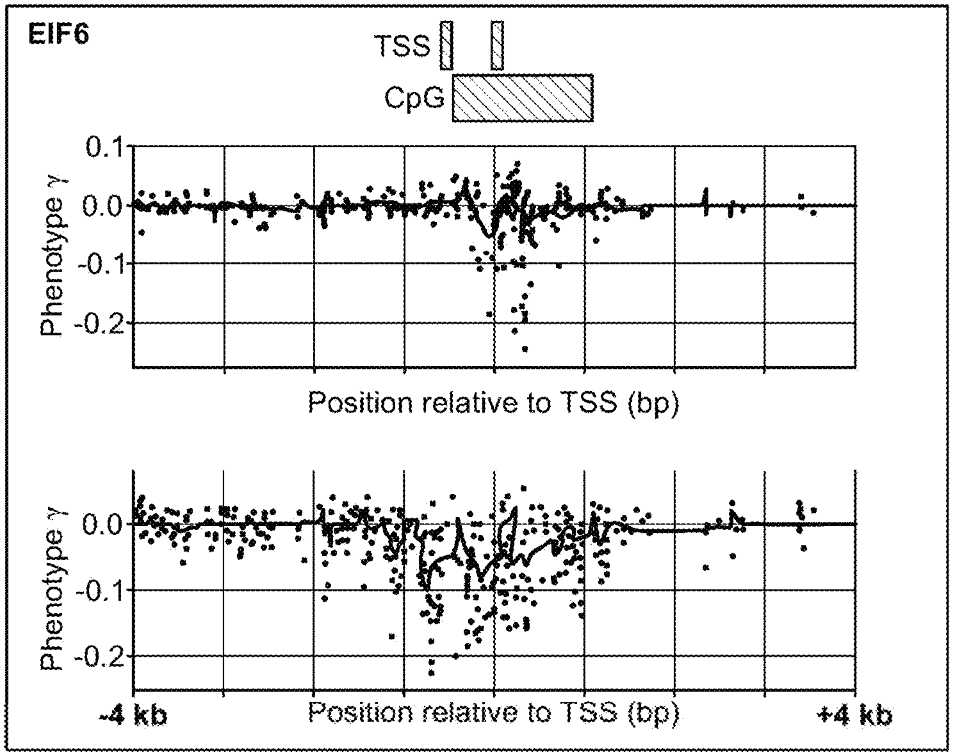
Figure 10D:
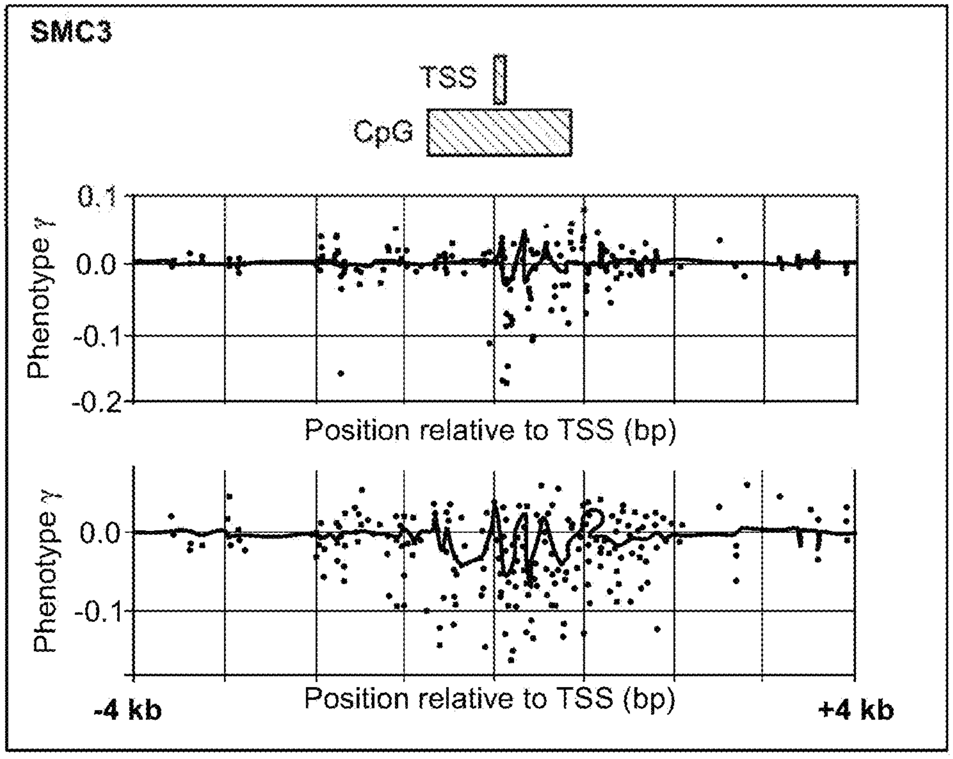
Figure 10E:
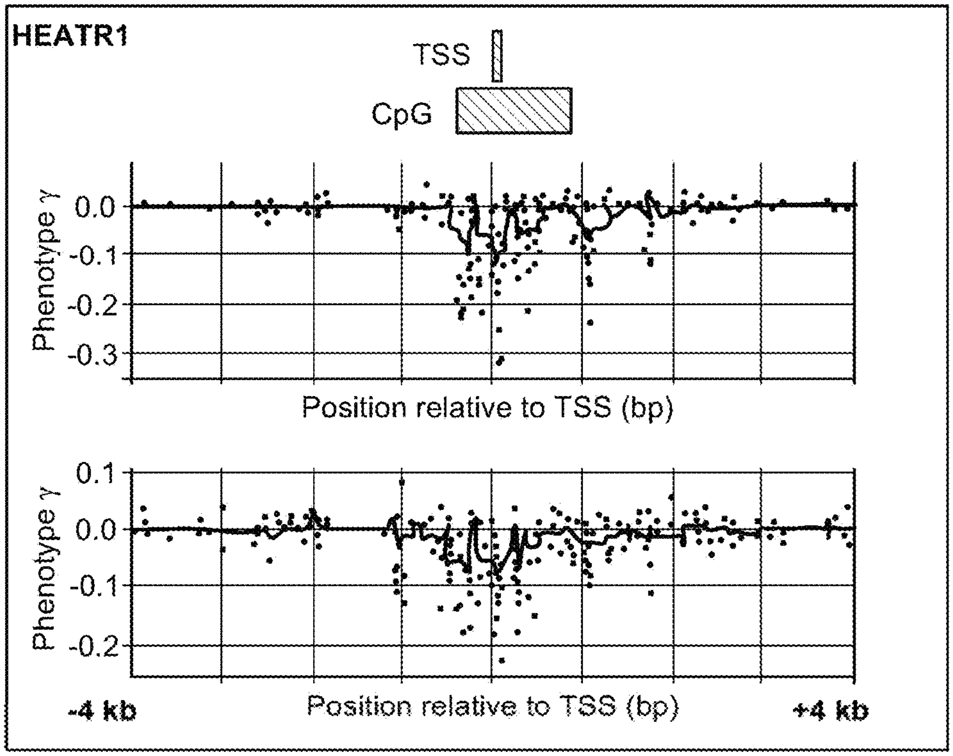

FIG. 10A shows the workflow of a pooled screen in HEK293T cells to determine optimal sgRNA targeting positions for the all-in-one protein, adapted from a previous ricin tiling screen in K562 cells to determine optimal sgRNAs for dCas9-KRAB (Gilbert, Horlbeck et al., Cell 2014). The sgRNAs are first stably expressed in HEK293T cells by lentiviral delivery, followed by transient transfection of a plasmid encoding the all-in-one protein (Day 0). Cells expressing the all-in-one protein are sorted (Day 2) and allowed to grow for three more days. Cells are split on Day 5, from which half are harvested as an initial time point, and the other half are passaged for ten more days (Day 15) for a final time point. The growth phenotype (γ) is calculated as the log 2 sgRNA enrichment divided by the number of cell doublings between T(initial) and T(final).

FIGS. 10B-10E are representative plots showing growth phenotypes for four genes (ARL1, EIF6, SMC3, HEATR1) from existing dCas9-KRAB/CRISPRi datasets in K562 cells (Gilbert, Horlbeck et al., 2014) and with the all-in-one protein (bottom plot). Each dot represents an sgRNA. The TSS and annotated CpG island are shown for each gene. The functional sgRNAs using the all-in-one protein spans a wider range than the functional sgRNAs, signifying a broader range of effective targeting.

Example 10

Figure 11A:
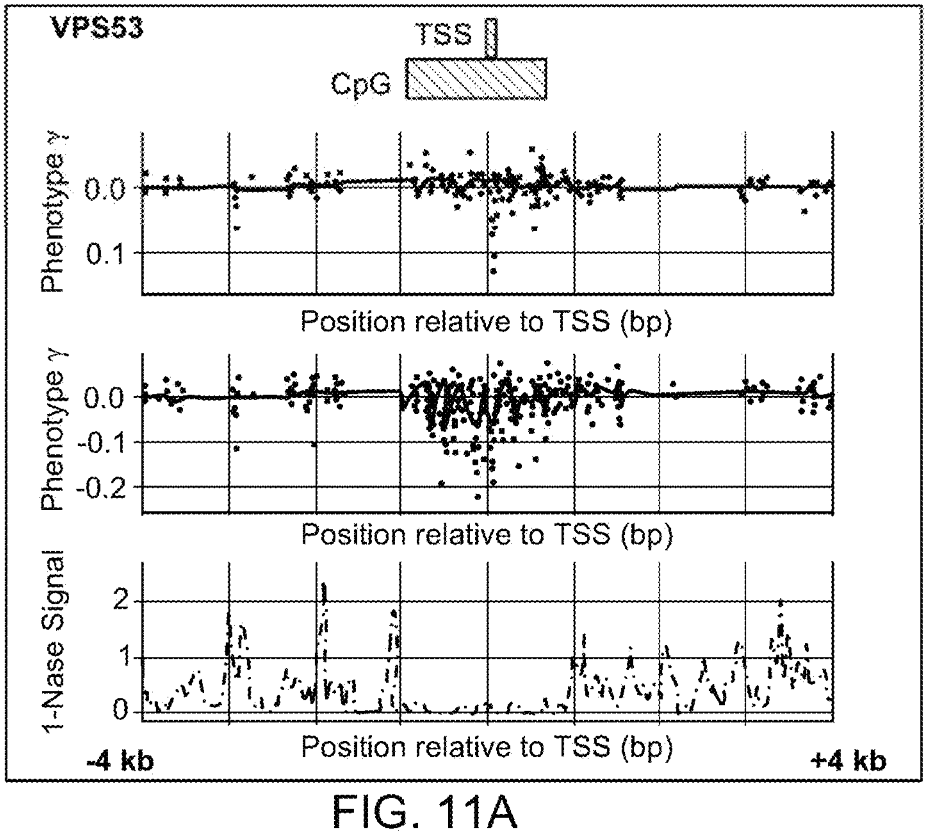
FIGS. 11A-11B provide a comparison of growth phenotypes and nucleosome positioning (from MNase signal) for VPS53 (FIG. 11A) and VPS54 (FIG. 11B) showing the location of functional sgRNAs at nucleosome-depleted regions.
Figure 11B:
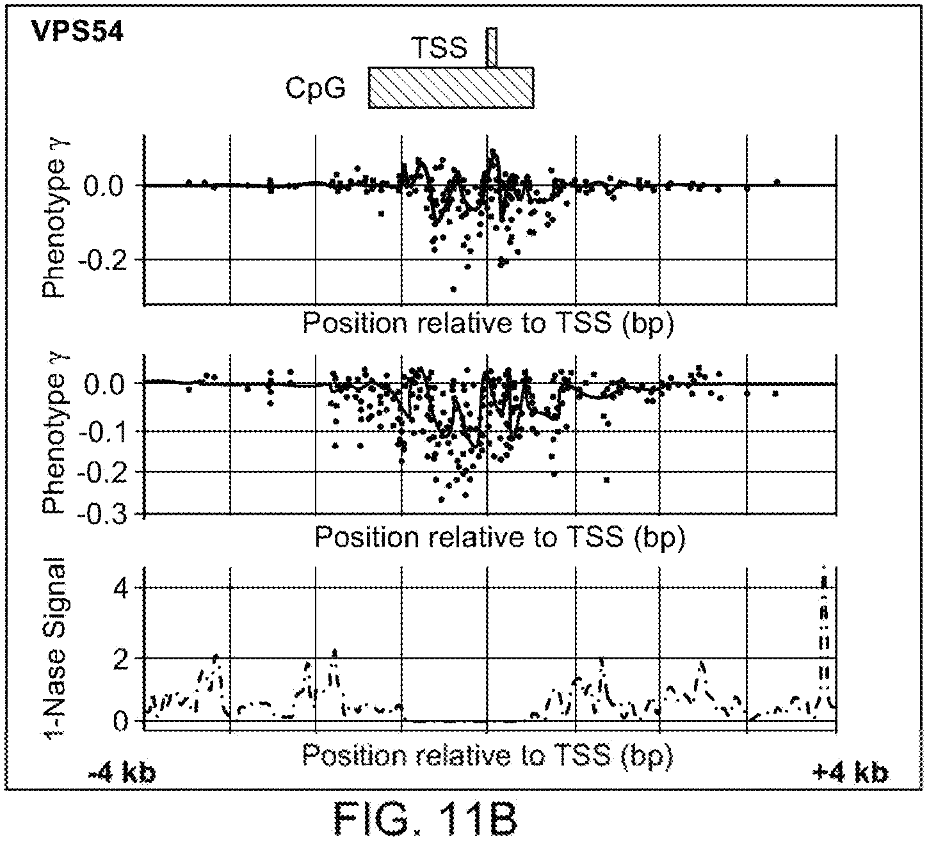

FIGS. 11A-11B provide a comparison of growth phenotypes and nucleosome positioning (from MNase signal) for VPS53 and VPS54 and show the location of functional sgRNAs at nucleosome-depleted regions. Furthermore, the range of functional sgRNAs is broader when using the all-in-one protein compared to dCas9-KRAB/CRISPRi.

Example 11

Figure 12A:
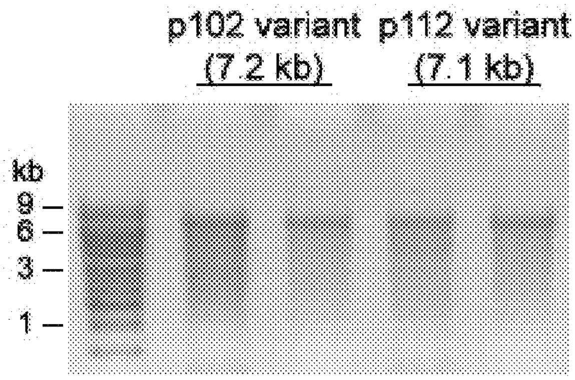
FIGS. 12A-12C show the delivery of the all-in-one protein by mRNA expression
Figure 12B:
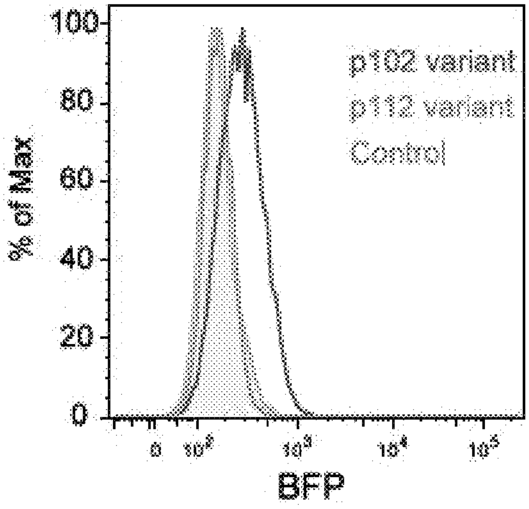
Figure 12C:
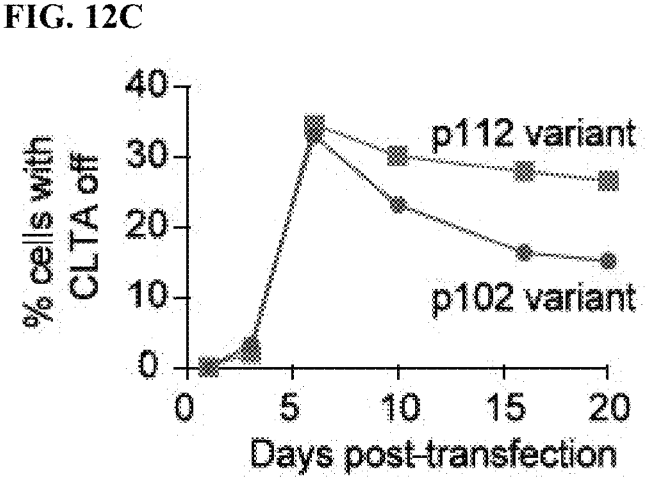

The in vitro transcription of two all-in-one variants (p102 (SEQ ID NO:14) and p112 (SEQ ID NO:15)) show full length synthesis of each design (FIG. 12A). FIG. 12B provides a flow cytometry plot showing expression of p102 and p112 one day post-transfection of mRNA into HEK293T cells. FIG. 12C shows the time course of CLTA endogenous gene silencing in HEK293T cells after transfecting mRNA expressing the p102 and p112 all-in-one variants.

Example 12

Figure 13A:
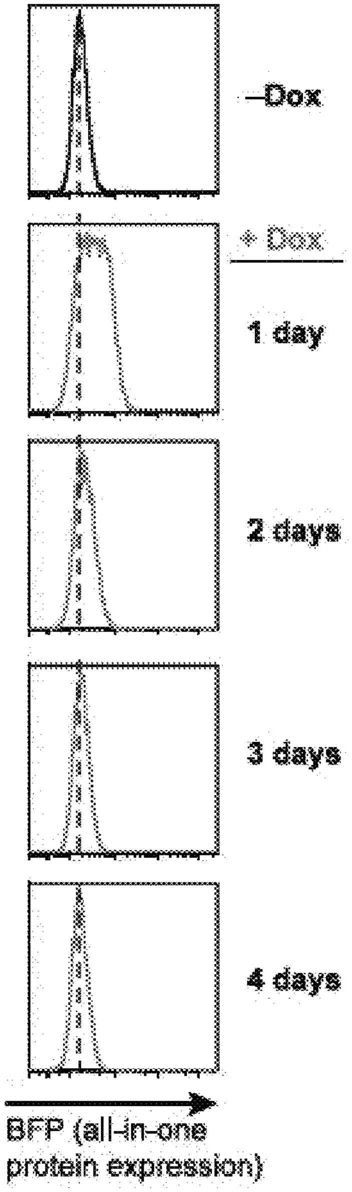

FIG. 13A provides flow cytometry plots showing induced expression of the all-in-one protein by addition of doxycycline in K562 cells that stably encode the all-in-one protein under a doxycycline-inducible promoter. Protein expression was followed for four days after doxycycline induction. The dotted lines in the panels in FIG. 13A represent the baseline median BFP fluorescence without doxycycline administration. Western blots of cells were performed to detect expression of the all-in-one protein before and after doxycycline treatment (FIG. 13B). The presence of the all-in-one protein is not detectable by 96 hours post-induction. Flow cytometry plots of CD81 and CD151 knockdown 14 days post-doxycycline treatment of K562 cells are shown in FIGS. 13C-13F. The percent of cells with the targeted gene knocked down is shown. There is no detectable expression of the all-in-one protein, as no cells are present in the BFP+ quadrants. Quantification of CD81 and CD151 knockdown 14 days post-doxycycline treatment or without doxycycline treatment is shown in FIG. 13G.

REFERENCES

Ecco et al, Development 144, 2017. Lambert et al, Cell 172, 2018. Siddique et al., J. Mol. Biol., 425, 2013. Stepper et al, Nucleic Acids Res., 45, 2017. Shmakov et al., Nat. Rev. Microbiol. 15, 2017. Cebrian-Serrano et al, Mamm. Genome 7-8, 2017. Pulecio et al., Cell Stem Cell 21, 2017.

What is claimed is:

1. A method of silencing a target nucleic acid sequence in a cell, wherein the method comprises delivering a complex to a cell containing the target nucleic acid; wherein the complex comprises: (i) a fusion protein comprising from N-terminus to C-terminus: a DNA methyltransferase domain, a nuclease-deficient RNA-guided DNA endonuclease enzyme, and a Krüppel associated box domain; wherein (1) the nuclease-deficient RNA-guided DNA endonuclease enzyme is dCas9 which comprises an amino acid sequence having at least 90% sequence identity to SEQ ID NO: 23; ddCas12a which comprises an amino acid sequence having at least 90% sequence identity to SEQ ID NO: 34; dLbCpf1 which comprises an amino acid sequence having at least 90% sequence identity to SEQ ID NO: 35; or dFnCpf1 which comprises an amino acid sequence having at least 90% sequence identity to SEQ ID NO: 36;

(2) the Krüppel associated box domain comprises an amino acid sequence having at least 90% sequence identity to SEQ ID NO: 16; and (3) the DNA methyltransferase domain comprises a Dnmt3A protein or a Dnmt3A protein and a Dnmt3L protein; wherein the Dnmt3A protein comprises an amino acid sequence with at least 90% sequence identity to SEQ ID NO: 26, and the Dnmt3L protein comprises an amino acid sequence with at least 90% sequence identity to SEQ ID NO: 28; and (ii) a polynucleotide comprising: (a) a DNA-targeting sequence that is complementary to a target polynucleotide sequence; and (b) a binding sequence for the nuclease-deficient RNA-guided DNA endonuclease enzyme, wherein the nuclease-deficient RNA-guided DNA endonuclease enzyme is bound to the polynucleotide via the binding sequence.

2. The method of claim 1, wherein the Krüppel associated box domain comprises an amino acid sequence having at least 95% sequence identity to SEQ ID NO: 16.

3. The method of claim 2, wherein the Krüppel associated box domain comprises an amino acid sequence having at least 99% sequence identity to SEQ ID NO: 16.

4. The method of claim 1, wherein the Dnmt3A protein comprises an amino acid sequence with at least 95% sequence identity to SEQ ID NO: 4.

5. The method of claim 4, wherein the Dnmt3A protein comprises an amino acid sequence with at least 99% sequence identity to SEQ ID NO: 4.

6. The method of claim 1, wherein the Dnmt3L protein comprises an amino acid sequence with at least 95% sequence identity to SEQ ID NO: 28.

7. The method of claim 6, wherein the Dnmt3L protein comprises an amino acid sequence with at least 99% sequence identity to SEQ ID NO: 28.

8. The method of claim 1, wherein the dCas9 comprises an amino acid sequence having at least 95% sequence identity to SEQ ID NO: 23.

9. The method of claim 8, wherein the dCas9 comprises an amino acid sequence having at least 99% sequence identity to SEQ ID NO: 23.

10. The method of claim 1, wherein the Krüppel associated box domain comprises an amino acid sequence of SEQ ID NO: 16, the Dnmt3A protein comprises an amino acid sequence of SEQ ID NO: 26, the Dnmt3L protein comprises an amino acid sequence of SEQ ID NO: 28 and the dCas9 comprises an amino acid sequence of SEQ ID NO: 23.

11. The method of claim 1, wherein the fusion protein further comprises a nuclear localization sequence.

12. The method of claim 11, wherein the nuclear localization sequence comprises the amino acid sequence of SEQ ID NO: 25.

13. The method of claim 1, wherein the cell is a eukaryotic cell.

14. The method of claim 1, wherein the cell is a mammalian cell.

* * * * *